US010920280B1

(12) United States Patent
Dennis

(10) Patent No.: US 10,920,280 B1
(45) Date of Patent: Feb. 16, 2021

(54) GENOME CAPTURE AND SEQUENCING FOR COMPREHENSIVE CHROMATIN STRUCTURE MAPS IN COMPLEX GENOMES AND CANCER PROGRESSION

(71) Applicant: The Florida State University Research Foundation, Inc., Tallahassee, FL (US)

(72) Inventor: Jonathan H. Dennis, Tallahassee, FL (US)

(73) Assignee: The Florida State University Research Foundation, Inc., Tallahassee, FL (US)

( * ) Notice: Subject to any disclaimer, the term of this patent is extended or adjusted under 35 U.S.C. 154(b) by 0 days.

(21) Appl. No.: 15/840,871

(22) Filed: Dec. 13, 2017

Related U.S. Application Data

(63) Continuation-in-part of application No. 14/600,773, filed on Jan. 20, 2015, now abandoned.

(60) Provisional application No. 61/928,473, filed on Jan. 17, 2014.

(51) Int. Cl.

| | |
|---|---|
| *C12Q 1/68* | (2018.01) |
| *C12Q 1/6886* | (2018.01) |
| *C12N 9/24* | (2006.01) |
| *C12Q 1/48* | (2006.01) |
| *G16B 30/00* | (2019.01) |
| *C12N 9/00* | (2006.01) |
| *C07H 21/04* | (2006.01) |

(52) U.S. Cl.
CPC ............. *C12Q 1/6886* (2013.01); *C12N 9/24* (2013.01); *C12Q 1/48* (2013.01); *G16B 30/00* (2019.02); *C12N 2310/50* (2013.01); *C12Q 2600/106* (2013.01); *C12Q 2600/112* (2013.01); *C12Q 2600/118* (2013.01); *C12Q 2600/158* (2013.01)

(58) Field of Classification Search
None
See application file for complete search history.

(56) References Cited

U.S. PATENT DOCUMENTS

| | | | |
|---|---|---|---|
| 8,725,423 B2 | 5/2014 | Gilbert et al. | |
| 8,728,979 B2 | 5/2014 | Gilbert et al. | |
| 9,245,090 B2 | 1/2016 | Gilbert et al. | |
| 2012/0322675 A1 | 12/2012 | Gilbert et al. | |
| 2013/0109584 A1* | 5/2013 | Guerrero-Preston | ........................ C12Q 1/6869 506/9 |
| 2013/0325360 A1* | 12/2013 | Deciu | .................. C12Q 1/6883 702/20 |
| 2014/0011196 A1* | 1/2014 | Rimseliene | ............ C12Q 1/683 435/6.11 |

OTHER PUBLICATIONS

Druliner et al., "Chromatin patterns associated with lung adenocarcinoma progression", Cell Cycle, 12:10, 1536, May 15, 2013. ( Year: 2013).*
Agalioti, T. et al. Ordered recruitment of chromatin modifying and general transcription factors to the IFN-beta promoter. Cell 103, 667-678 (2000).
Bakhoum, S. F., Thompson, S. L., Manning, A. L. & Compton, D. A. Genome stability is ensured by temporal control of kinetochore-microtubule dynamics. Nat Cell Biol 11, 27-35 (2009).
Bolshoy, A., McNamara, P., Harrington, R. E. & Trifonov, E. N. Curved DNA without A-A: experimental estimation of all 16 DNA wedge angles. Proc Natl Acad Sci U S A 88, 2312-2316 (1991).
Boyle, A. P. et al. High-resolution mapping and characterization of open chromatin across the genome. Cell 132, 311-322 (2008).
Dennis, J. H. et al. Independent and complementary methods for large-scale structural analysis of mammalian chromatin. Genome Res 17, 928-939 (2007).
Ding, L. et al. Somatic mutations affect key pathways in lung adenocarcinoma. Nature 455, 1069-1075 (2008).
Drew, H. R. & Travers, A. A. Structural junctions in DNA: the influence of flanking sequence on nuclease digestion specificities. Nucleic Acids Res 13, 4445-4467 (1985).
Druliner, B. R. et al. Chromatin patterns associated with lung adenocarcinoma progression. Cell Cycle 12, 1536-1543 (2013).
Eden, E., et al. Discovering motifs in ranked lists of DNA sequences. PLoS Comput Biol 3, e39 (2007).
Encode Project Consortium. "A user's guide to the encyclopedia of DNA elements (ENCODE)." PLoS biology 9.4 (2011): e1001046.
Feinberg, A. P. Epigenetic stochasticity, nuclear structure and cancer: the implications for medicine. J Intern Med (2014), 5-11.
Fenouil, R. et al. CpG islands and GC content dictate nucleosome depletion in a transcription-independent manner at mammalian promoters. Genome Res 22, 2399-2408 (2012).
Gaffney, D. J. et al. Controls of nucleosome positioning in the human genome. PLoS Genet 8, e1003036 (2012).
Goldberg, A. D., Allis, C. D. & Bernstein, E. Epigenetics: a landscape takes shape. Cell 128, 635-638 (2007).
Gupta, S. et al. Predicting human nucleosome occupancy from primary sequence. PLoS Comput Biol 4, e1000134 (2008).

(Continued)

*Primary Examiner* — Bradley L. Sisson
(74) *Attorney, Agent, or Firm* — Meunier Carlin & Curfman LLC

(57) ABSTRACT

A MNase-Sequence Capture method, mTSS-seq, was developed herein to map genome-wide nucleosome distribution in cancer, for example primary human lung and colon adenocarcinoma tissue. Here, it was confirmed that nucleosome redistribution is an early, widespread event in lung adenocarcinoma (LAC) and colon adenocarcinoma (CRC). These altered nucleosome architectures are consistent between LAC and CRC patient samples indicating that they can serve as important early adenocarcinoma markers. As such, this consistency would be expected in other adenocarcinomas, as well as other carcinomas. It was demonstrated that the nucleosome alterations are driven by the underlying DNA sequence and potentiate transcription factor binding. DNA-directed nucleosome redistributions are widespread early in cancer progression, thus providing a methodology for early detection of cancer in grade one patients.

16 Claims, 43 Drawing Sheets
(3 of 43 Drawing Sheet(s) Filed in Color)
Specification includes a Sequence Listing.

(56) References Cited

OTHER PUBLICATIONS

Henikoff, J. G., et al. Epigenome characterization at single base-pair resolution. Proc Natl Acad Sci U S A 108, 18318-18323 (2011).
Hill, V. K. et al. Genome-wide DNA methylation profiling of CpG islands in breast cancer identifies novel genes associated with tumorigenicity. Cancer Res 71, 2988-2999 (2011).
Jiang, C. & Pugh, B. F. Nucleosome positioning and gene regulation: advances through genomics. Nat Rev Genet 10, 161-172 (2009).
Kaplan, N. et al. The DNA-encoded nucleosome organization of a eukaryotic genome. Nature 458, 362-366 (2009).
Kent, N. A., et al. Chromatin particle spectrum analysis: a method for comparative chromatin structure analysis using paired-end mode next-generation DNA sequencing. Nucleic Acids Res 39, e26 (2011).
Kent, W. J. et al. The human genome browser at UCSC. Genome Res 12, 996-1006 (2002).
Kent, W. J., Zweig, A. S., Barber, G., Hinrichs, A. S. & Karolchik, D. BigWig and BigBed: enabling browsing of large distributed datasets. Bioinformatics 26, 2204-2207 (2010).
Kim, T. M. et al. Genome-wide screening of genomic alterations and their clinicopathologic implications in non-small cell lung cancers. Clin Cancer Res 11, 8235-8242 (2005).
Kohno, T. et al. Association of KRAS polymorphisms with risk for lung adenocarcinoma accompanied by atypical adenomatous hyperplasias. Carcinogenesis 29, 957-963 (2008).
Kornberg, R. D. & Lorch, Y. Twenty-five years of the nucleosome, fundamental particle of the eukaryote chromosome. Cell 98, 285-294 (1999).
Kundaje, A. et al. Ubiquitous heterogeneity and asymmetry of the chromatin environment at regulatory elements. Genome Res 22, 1735-1747 (2012).
Kundel, D. W. et al. Molecular characterizations of Nop16 in murine mammary tumors with varying levels of c-Myc. Transgenic Res 21, 393-406 (2012).
Langmead, B. & Salzberg, S. L. Fast gapped-read alignment with Bowtie 2. Nat Methods 9, 357-359 (2012).
Lee, W. et al. A high-resolution atlas of nucleosome occupancy in yeast. Nat Genet 39, 1235-1244 (2007).
Li, H. et al. The Sequence Alignment/Map format and SAMtools. Bioinformatics 25, 2078-2079 (2009).
Liu, P. et al. Candidate lung tumor susceptibility genes identified through whole-genome association analyses in inbred mice. Nat Genet 38, 888-895 (2006).
Neely, K. E. & Workman, J. L. The complexity of chromatin remodeling and its links to cancer. Biochim Biophys Acta 1603, 19-29 (2002).
Ng, S. B. et al. Targeted capture and massively parallel sequencing of 12 human exomes. Nature 461, 272-276 (2009).
Quinlan, A. R. & Hall, I. M. BEDTools: a flexible suite of utilities for comparing genomic features. Bioinformatics 26, 841-842 (2010).
Reisman, D. N., Sciarrotta, J., Wang, W., Funkhouser, W. K. & Weissman, B. E. Loss of BRG1/BRM in human lung cancer cell lines and primary lung cancers: correlation with poor prognosis. Cancer Res 63, 560-566 (2003).
Sarvaiya, P. J., Guo, D., Ulasov, I., Gabikian, P. & Lesniak, M. S. Chemokines in tumor progression and metastasis. Oncotarget 4, 2171-2185 (2013).
Schellman, J. A. Flexibility of DNA. Biopolymers 13, 217-226 (1974).
Schones, D. E. et al. Dynamic regulation of nucleosome positioning in the human genome. Cell 132, 887-898 (2008).
Segal, E. et al. A genomic code for nucleosome positioning. Nature 442, 772-778 (2006).
Sexton, B. S. et al. The spring-loaded genome: nucleosome redistributions are widespread, transient, and DNA-directed. Genome Res 24, 251-259 (2014).
Timp, W. & Feinberg, A. P. Cancer as a dysregulated epigenome allowing cellular growth advantage at the expense of the host. Nat Rev Cancer 13, 497-510 (2013).
Trifonov, E. N. & Sussman, J. L. The pitch of chromatin DNA is reflected in its nucleotide sequence. Proc Natl Acad Sci U S A 77, 3816-3820 (1980).
Valouev, A. et al. Determinants of nucleosome organization in primary human cells. Nature 474, 516-520 (2011).
Varela, I. et al. Exome sequencing identifies frequent mutation of the SWI/SNF complex gene PBRM1 in renal carcinoma. Nature 469, 539-542 (2011).
Webb, E. L. et al. Search for low penetrance alleles for colorectal cancer through a scan of 1467 non-synonymous SNPs in 2575 cases and 2707 controls with validation by kin-cohort analysis of 14 704 first-degree relatives. Hum Mol Genet 15, 3263-3271 (2006).
Yang, H. et al. ATM sequence variants associate with susceptibility to non-small cell lung cancer. Int J Cancer 121, 2254-2259 (2007).
Yigit, E. et al. High-resolution nucleosome mapping of targeted regions using BAC-based enrichment. Nucleic Acids Res 41, e87 (2013).
Yuan, G. C. et al. Genome-scale identification of nucleosome positions in S. cerevisiae. Science 309, 626-630 (2005).
Zang, Z. J. et al. Exome sequencing of gastric adenocarcinoma identifies recurrent somatic mutations in cell adhesion and chromatin remodeling genes. Nat Genet 44, 570-574 (2012).
Zhang, Y., Shin, H., Song, J. S., Lei, Y. & Liu, X. S. Identifying positioned nucleosomes with epigenetic marks in human from ChIP-Seq. BMC Genomics 9, 537 (2008).
Zhurkin, V. B., Lysov, Y. P. & Ivanov, V. I. Anisotropic flexibility of DNA and the nucleosomal structure. Nucleic Acids Res 6, 1081-1096 (1979).

* cited by examiner

| Cluster | GO Process | P-Value |
|---|---|---|
| 1 | – response to other organism<br>– nucleosome assembly<br>– mRNA metabolic process<br>– RNA processing<br>– G-protein couple receptor activity* | $9.91 \times 10^{-6}$<br>$1.78 \times 10^{-4}$<br>$5.34 \times 10^{-4}$<br>$6.32 \times 10^{-4}$<br>$1.51 \times 10^{-19}$ |
| 2 | – regulation of cellular process<br>– biological regulation<br>– regulation of metabolic process<br>– regulation of cell morphogenesis involved in differentiation | $3.12 \times 10^{-27}$<br>$6.05 \times 10^{-25}$<br>$3.13 \times 10^{-17}$<br>$6.72 \times 10^{-16}$ |
| 3 | – regulation of cellular process<br>– biological process<br>– carbohydrate transport<br>– lipid modification | $1.66 \times 10^{-4}$<br>$5.17 \times 10^{-4}$<br>$6.21 \times 10^{-4}$<br>$7.19 \times 10^{-4}$ |
| 4 | – nuclear-transcribed mRNA catabolic process<br>– cell process involved in reprod.<br>– mRNA catabolic process<br>– mitotic G2 DNA damage chkpnt.<br>– G-protein coupled receptor activity* | $3.47 \times 10^{-4}$<br>$7.34 \times 10^{-4}$<br>$7.40 \times 10^{-4}$<br>$8.93 \times 10^{-4}$<br>$1.51 \times 10^{-19}$ |

*GO function, rather than process

FIG. 3E

SEQUENCE LISTING

```
<160> NUMBER OF SEQ ID NOS: 15

<210> SEQ ID NO 1
<211> LENGTH: 22
<212> TYPE: DNA
<213> ORGANISM: Homo sapiens

<400> SEQUENCE: 1
aatgatacgg cgaccaccga ga                                              22

<210> SEQ ID NO 2
<211> LENGTH: 22
<212> TYPE: DNA
<213> ORGANISM: Homo sapiens

<400> SEQUENCE: 2
caagcagaag acggcatacg ag                                              22

<210> SEQ ID NO 3
<211> LENGTH: 20
<212> TYPE: DNA
<213> ORGANISM: Homo sapiens

<400> SEQUENCE: 3
ctgggaaatt cagtcgtgtg                                                 20

<210> SEQ ID NO 4
<211> LENGTH: 20
<212> TYPE: DNA
<213> ORGANISM: Homo sapiens

<400> SEQUENCE: 4
tattggccaa gtccgctaag                                                 20
```

-continued

```
<210> SEQ ID NO 5
<211> LENGTH: 21
<212> TYPE: DNA
<213> ORGANISM: Homo sapiens

<400> SEQUENCE: 5
aatttaagcg cctgattcga g                                     21

<210> SEQ ID NO 6
<211> LENGTH: 21
<212> TYPE: DNA
<213> ORGANISM: Homo sapiens

<400> SEQUENCE: 6
ccttgtttgg aatctgaatg c                                     21

<210> SEQ ID NO 7
<211> LENGTH: 21
<212> TYPE: DNA
<213> ORGANISM: Homo sapiens

<400> SEQUENCE: 7
agatgtccac cctcttgttc c                                     21

<210> SEQ ID NO 8
<211> LENGTH: 20
<212> TYPE: DNA
<213> ORGANISM: Homo sapiens

<400> SEQUENCE: 8
ccagggaaga aagcgaattg                                       20

<210> SEQ ID NO 9
<211> LENGTH: 20
<212> TYPE: DNA
<213> ORGANISM: Homo sapiens

<400> SEQUENCE: 9
ttgctgaaga cgatgaggag                                       20

<210> SEQ ID NO 10
<211> LENGTH: 20
<212> TYPE: DNA
<213> ORGANISM: Homo sapiens

<400> SEQUENCE: 10
caatccgaaa gaagctggtg                                       20

<210> SEQ ID NO 11
<211> LENGTH: 21
<212> TYPE: DNA
<213> ORGANISM: Homo sapiens

<400> SEQUENCE: 11
tatggctgtc tctctggttg c                                     21

<210> SEQ ID NO 12
<211> LENGTH: 20
<212> TYPE: DNA
<213> ORGANISM: Homo sapiens

<400> SEQUENCE: 12
aacgcaacac acctgaactg                                       20
```

```
<210> SEQ ID NO 13
<211> LENGTH: 21
<212> TYPE: DNA
<213> ORGANISM: Homo sapiens

<400> SEQUENCE: 13
caacgcttca gtgatcaatc c                                               21

<210> SEQ ID NO 14
<211> LENGTH: 18
<212> TYPE: DNA
<213> ORGANISM: Homo sapiens

<400> SEQUENCE: 14
gagctgttcg cacgtctg                                                   18

<210> SEQ ID NO 15
<211> LENGTH: 27065
<212> TYPE: DNA
<213> ORGANISM: Homo sapiens
<220> FEATURE:
<221> NAME/KEY: misc_feature
<222> LOCATION: (2923)..(2932)
<223> OTHER INFORMATION: N can be A, C, T, or G.
<220> FEATURE:
<221> NAME/KEY: misc_feature
<222> LOCATION: (13127)..(13588)
<223> OTHER INFORMATION: N can be A, C, T, or G.

<400> SEQUENCE: 15
ccgaagagtt gctgagcaca tgaccaccaa aaaaggtttc ggcacctgtg gacctgtggg        60
taggggaggc aggggcaaat gtcactttac gtcaggggga ggataaaatc gaacgtttat       120
taacattgat tttgtgccag aggtggctac ccagacccat ccactgtagc cgtgaggttg       180
gaagggagag gggaggcatg aactggtttg tccaaggtcg ttggcagagc gcggctgtga       240
actgggttag cccccaggcc cctcctgccc atccgtcctc caagcactga tgtgcgagtg       300
gcacagtggt cccccttggcc ctgccagccc ctcgggctgt ggccctatag cctttgaagg      360
acggcctcac ttccccagca gaggcagcct ggccttccag tacctcgatg gtgtagggct       420
ctggggccac agtctggtgt tttcaggact aggttgtggg ttacttcctc ctcttctctc       480
aattcccaag gtttgttaag cggccctgta gctccggtca tggcaatatg gatttactgg      540
cggtgctttc tgaagctgtg gatgcaattc tcacaagtgg ccacatggtg tcaggctcgg       600
gccagattag gaaatctccg ctttacaggt ggagccgggt ggggctgggg aagcgagtta      660
agaacgaaat tcagcccatc tgggctcatc ctagggacgc tgtctctgaa aggggggtctc     720 aacgttctgc cccgggcctc tcagtaatag atctcatttt atgttcatgc taatgtggtg      780
gtttcctctc ttagaacaaa acggatgctt cagaaaggtg ttccagacct atcctgtggc      840
ttaggcccta agctttagga tgctcaccag gccacagccc cctcgggtta ggagacaccc      900
gaagggagga attccctcag cgccccctct cagtcctgta atgccgggac agaagcagat      960
aagagccccg gttccaaaca caaaggtgca ggacccatgg caccctgaca ctgtagggag      1020
gcgtcctgac tttgccccca gagtcccect ccagagtgcc ccaaattgcg gcgcccaaga     1080
cctttgggtt atgccactgt aattctagaa atggccgcca ggtgtcagca gaaggccact     1140
taagaagcta aatggcgaaa gcttggtgta gcagatttct gggggttccc aagactctca     1200
tgcatgaaca ggggtgggct gagcctctcc caggcctaag aggcagtgga gcaaggaggt     1260
ttttctatgt cgtgtccctc aatcctgcac cccagttttt gtccatttg cggtccctct       1320
```

```
cacctgtctc cataaagcat gtgtccccca gacccttgcg tggaaaatct gtggaatgta    1380
gtgctgtggg gccacagccc tcacacccca actcactgat ccccaatgcc tctagtcctg    1440
cctcggtggc accatggctt agctgctccc cgggggccct ttctatcctg accgcttctc    1500
cctgctctcc ttctcctgtt tacacaccct gggttccaag atcctgatgg gataaaatag    1560
ccttggagac tagagtgagc tcctcctggg cccatccaga gatggaattc cagtccaggg    1620
cagagtttgg attcaagaca ccattgtggg cctgggaggc tccaggtttc caggagtttg    1680
acctgtgggc tgcttccctt tcagccccat agctgcccac ctcctcaacc tggggactgt    1740
tcatttgggg gggcatccca tggaatcact tcatctggct gggtgtcagc ccgtcactct    1800
ctctaggtcc atctgcagct tggaaagtcc cagccaagtg tctccagagg gctctggcag    1860
tcgctgtttg caacatttgg gcatcttgca gcagacactg ggaccagcac atgctacggg    1920
gtctctaagc catagagccc cggagcaagg gctgcttcat gctgacctcc ttgtatcttt    1980
gttttgtttc tttccctgag tctttgtttt gtgccttctc ttcctgcagg cttgaggaag    2040
aggtgtcaaa ttcccagtaa gacttgatct aatccaatgg gtgattctat ctgagccctc    2100
cctgagctgc tgccagctct gagtctgtgc tttagctgga aagactgtga acccattcag    2160
tgctctggac ctgacagggc cattaacatc cctccccacc caaaagccga gtgaaaaatc    2220
ccattttccc tcctcccatg ggagggcatg gctctgggc atctacgtct tatttgagac    2280 atccccaac acatgccaga tttgaatccc cttcaagtct aactctcttc cctgctgaaa    2340
tccttgttgt ccccactaga tgtcctattc ctccagctaa tgaagggatt taagacgagg    2400
gcttgaaaga aaaagggaga ggggacaatt aaatcccaac acaggctagt aaaactaatc    2460
acactgaagg tggttggggt gcgtgggtgt tggaggggg gactggtggc tctctggaaa    2520
gtacacgtct ttgcctcttc ctgagtcttt gctagcttgg ggaagaggtt agaaatttcc    2580
agtgtgattt agtccaatct ggtggatgct tctatatgaa ccctcaccca gctgctgtca    2640
gctttgagtc tgtgctttaa ttagaaaggc tgcgaacctg tccaatcgcc caatccagaa    2700
atgcctgcaa gtgcccctg cagcagtgtc attagagctt agtaccacac agggagtgtc    2760
tgaggtcaga tcagacgtga ccagtgaagt gaaaaacccc ccagctgagt accttgctca    2820
tggaagatgg aaggacataa ctgcacagta cataactgta ccgggagcac ctaaaatcca    2880 attttctgc tgattcttga accctgcttt gtccccctta ttnnnnnnnn nnattttacc    2940
agtgccacgt ccaccaacat tccagggtgt caagtaactg ccaagtgtca ctctaagtaa    3000
agctacaccc actccccacc acctccacat agccccacc tcctagctgg cagggagctt    3060
ctggcttatg cccacgccca caggcgcctt tctgccaggt caggggtggg ccaaacctcc    3120
acccgctaat gtaccatgcc ctggtgctgg aaagtgcctg agccagctgc ccagcggcc    3180 tcggcactac caagttggca caaagctccc caaattcgga ggggctcagg gaaacgagtg    3240
gaggggatga ggaggtgagg ggtaaaccca tcatttcagt tggcatttga gcaggtgcca    3300
tgctcagcgg agatgaggct ctcccatctg taggggccgt attaacatgc acactctaaa    3360
agtgcccttc gtttctccag cctcagcttt gtccctctcc tcctccacgt caacctggcc    3420
agagggtctg gacgccacag ccagggcacc ccctgctttg tggtgactg ctaatattgg    3480 ccaggccggc ggatcatcgt ccaggcagtt tcggcagaga gccttgggca ccagtgactc    3540
cccggtcctc tttatccact gtccaggagc tgcggggact gcgcagggac tagagtacag    3600
gtaactgggc tcccatccct tgagtgtgag agaaaagctg cactttaagt gttcaggcgt    3660
gggtgggccg ggagcttggg gcagctgcca ggatcctggt ttctgaagga ggggaagaac    3720
```

```
ttctgctgct ggagggtgca gggaagcctc ctgagagcag cctcaacttc agggatgggg     3780
tgtgcaggaa aggccattgt ggagagggtt cttctttagg gctgcacaaa gccactgagg     3840
cttttgcaag gaaaataggt tttccttgac taattcacca agcaaaatgg gaggggtagg     3900
ggaggagggc taggccgctc ttcccagcgg gaacacacag ctgtcttcac aagtgtgaaa     3960
ggaagagtct ttctgtgtga aaagtttcct cccgttgcat cccccatccc attcccagag     4020
acaaacagga gactttgcag aggagccggg ggcccgagat tctggcgcag atattttatt     4080
tatacatata tacaccattt tacaggtaaa gcttccttcc ctcctgcctc cctatgcctg     4140
ctgaccacca gcaagaaatt ggacaggaga ctgaggagaa acgccgggag aggcaacaac     4200
ggccctccat gtccccccta ggtttagctt ctctcctcct gatggcgcac ctggtccccc     4260
ttgctgctct cccagcctcc ctggcacaga gaggcgccct ggggccaagg cagtttccct     4320
gggaatgctc attcatgcat gaagtttttc tctgttgcac cctggaccca gactcctcaa     4380
tccacccagg gtggtgtctg tggggagggg gttcatttcc ccaggaagca cagccacgcc     4440
gtccctcact ggcctcgtca agcagagctg tgtgtccagt ggcttttgct ggggccccct     4500
ccttatctcc ttccaaggtg ggggtgtttg gaggtggagg aggctttcat attccgtgcc     4560
atgacccctc aaggcgggcc attcgtgtgc accctccacc cccagtgcca ggcagaagcc     4620
catcctcacc caggaacagg gcagcctgtc caacagaagg gtctcggcct ctccatcagc     4680
accgggaagc cctttctagg caaacttctc accacttctt ccctccctta tactttgaaa     4740
gagggagctc taggcagggg aggggctaga gggggaagcc gctgcccaga tcctgacaag     4800
gtgacctgaa ggaacccggg gagggggatg ggacagggct caggcctggg gtgtatgggg     4860
aggggggctt tgcttttaaa agaggtcatc tcagcaatat cttttgtttt ttccccaggg     4920
gccgaagagt caccaccgag cttgtgtggg aggaggtgga ttccagcccc cagccccagg     4980
gctctgaatc gctgccagct cagcccctg cccagcctgc ccacagcct gagccccagc     5040 aggccagaga gcccagtcct gaggtgagct gctgtggcct gtggcccagg cgaccccagc     5100
gctcccagaa ctgaggctgg cagccagccc cagcctcagc cccaactgcg aggcagagag     5160
gtgagtgtct caggcaccct gaggcctggc agagagggcc acaggctctg cgcgggagtc     5220
ttcgaactgg gatctccccc ttctgcaagc agctttggct cagagaggct ggcgtggatt     5280
cagtcacaca gctgggatct ggagttccgt ggttggctcc aggtgcttcc gtctaggggc     5340
cagagcaggt gtgggcagag caggttcccc gcagtctcca cggcaccgag gtcctggcag     5400
gggagctcct gggagacgaa agagggcaaa gaagggggaga ggggcaggga gagagcgggc     5460
agccaaaggg gagaagatgg ggggcagaaa gtgggtagag agggaaaaag ggaaaatatc     5520
attggggaag aacctaaaaa cccaaggaaa gctgggctct gctgggggct gtgagacccc     5580
ggggttctcc ccgccccagg ctgctggcca tggggtcttg caccaatggc ctgacctttc     5640
tgtcggtctg tatttatcaa agtgggtgac agtctcaggc ctcctggctg ttcagaattg     5700
aggtaataac cagaggcctt ctgagcaaag ggcctaaggg gctccggcgt caggatccca     5760
ttgtggtcag gagcctgcgg ggcttcccgt gtgcaagagg ggtgaaaggt ggctagaaag     5820
gcccagccag tggcctctgc ctcagccaga gggagctctg tagtggggc agcacccatt     5880 cactggtcag gcactggggt gacagggggag gctccaggac ttggggagcg ttggagctgg     5940
aggcacatgg attggagtcc ctgtacctgc cccacgacag ggcctgcagg gagggatcca     6000
gcaggtgact cttcaggctg atttgcccat cccagataga agccgggagt gttctttcaa     6060
aggtgtcttt accttagaca ctcaataaaa tggtaacaca gtggcgccgc ctcagtcctt     6120
```

```
tggagtgtgc accgtctgaa cccctctccc agggccctct cccaagcacc ccaacctgga    6180
cccatatccc ccacgtactt ttggctttgg gcagattgag cagccttggg gtggtctgtg    6240
ctgtctggtg tggagggttg cagttcgggt ccttagtcct acttcccagg ccggccgggc    6300
tgacgccagc gagtgtgtcc ttccccagcg aggggagcga gcgcaaggtc agcgcctcgt    6360
ctgcggcgcc ctgcaggggg tgacggaggg gcgctctgag gacccttgga gaaaggagct    6420
gggtttgtaa aatgctgggc ttggtcccac ggacggcgga gcggtgagct cagagccaga    6480
gctggggagg aaatgggaat gagaaaggcc cacttcaggg ctggtgagcg aggggatggg    6540
gagcagccac aggccgaggc tggggcatgg gccaggctcc atggggtgag tctgagtcct    6600 tgagggatg ttcatcctct gtggaatgtg ggtttgccag tggagaggag actagcgttg    6660
ccctggtgag gtgctggttc agggctgggg ggcggacgct gcttgggct aaagttcctg    6720 ccggccaagc tctgggtggg aggagaccct ggccccctcc caacaccctt ggactgctgg    6780 cgggacccttt cctacctccg ggggctggaa gtagtggggg aggagccagt cttgaggaag    6840
aaccccgatg ctggtcttga ctagagggga gccggtgtgc ttttcgagcc tcagggtgac    6900
ccgcgtctgc cccagcctcc agcctgccct ggtcacttct gactaaataa ggagagcact    6960
cagcaggcag ccccacgagg gaggggggaac atgtgtgcac ccccactccc ccacctgctc    7020
ctccctccct acagggccac tacaccctgc tgtgggcacc ccaaggtgac cctcagcctt    7080
cttcctacct taaaaagtcc aggcatgcgt tttcaagcat gagcggtggc ccctggggg    7140 aaggcacctc ggcagggcag aacaagggga agggaccccc aaacaggtca ctggtgtaat    7200
tgtccccagc accccaaag aggaggagaa cccacaactc ggaactgggg ctcaccccg    7260 atgcccaacc tgtccccagc ctgggaagca ggcgtggagg agaaggtggg gggagcctag    7320
agctggccct gggggccctg gttttgtcca tgacggagc ctcggcaacc tagtccgctc    7380
tcccggggac caggtttgca gacaggcacc tttcaaatgc tcctcacccc caaatttaca    7440
agtcaccctg cagaggaaaa catcaacaca gccagggggt tctgctggat ggctccccct    7500
tctataggca cagccggaga ggccagagag ctggggacac ggggaggctg cagaaggctg    7560
gtgggaaggg gggcagtgat gggtggggag agatgggcca gatgttcttg gaatgggaca    7620
tgggggtgat tgatgcagac agaaatttga agggacatt cccacgtgtc ttgttctgtg    7680 ggtgaaaat gggctgtttt tcatggtggg ggcgggttct ccctgtcttg ccaagctaat    7740
gtgaaagaga tgcctcatcc tgcccagctc cccacacctg tccaaggcca ttaacttctg    7800 cctcccagt gtcaggcttt gagatgcccc ccttctagcc ggggtcctcc tatgggtga    7860 caatggggac aagcaatgcc cactgtagtt gccccaggat ccccccacat tctgctggtc    7920
cccagcggtg cccctctct ggcagtaccc cacccacccc cacaggtccc cttagggcca    7980
ctgccccatc gcccgacatt gcccaacgcc aagggtgac cttgttcctg ccgacagggc    8040
cgttgggcgc ctgcatgcgg gtttaatatt tgcctataag gaactgggct ttcccccagcc    8100 ggagtggaca gactttccct gaaaattcgc ttggagagaa cgaaaagaga cccctggcac    8160
cccagcggcg tgcagccctg cacccccctc ctcccgggcc ccgtgttttct cattttcctc    8220 cccacttcct ctgctcttca gtgttaccca aacaaaactg gtttcaccct tgtttggtgc    8280
tggcgaaggc ccgaacggcg cgcgcaaagc tccggggcag gccggaggtg gccaccgggg    8340
gtgctccggg cccccaagcc aagccgggga ctagcctgct cccggtggcg gctcggccgc    8400
ggcttcgcct aggctcgcag cgcggaggcg agtgggcgc agtggcgagg gggagcctgc    8460
ggacctccca cgcggggacc gagcaggtat ctgggagtcc cgggagcgcc cgggaagcag    8520
```

-continued

```
cgtcctggtc gctccctcgc ggcccttggg tttcttcctt acacccggac gcccgctaag    8580
ctcgggctgc cgccacaaac gcgctctccg tgtggagaag gcaaagaaaa aaaaaataaa    8640
agcaaaagga agaaaaaccc caaagaacga aaagcagaat tcagccggc cgtgcgcgcc     8700 agggcgctcc gcgctacctg cccgcgccgc ccgcgctcgg gttccggggg agggcgccag    8760
tgctccgcgc gcgcccagc caaggtgaat ccccggcagc gccttccttc cgctgcccgg     8820
gaagcttgag ctcaacaatt agcccttgat cctcggggga ttccaatcca cggaacaact    8880
tccctgcttt ccccgaactc ggacatttta cttttctgg gatcctctaa atttaagcat     8940
tgcttcccaa gtcttctaaa tatattcacc atttcgacgg gtcacaataa ttttcttgga    9000
cgttaatttc cggggacgtc aaaacacatc agtcccggcg ggcttttcca gacttacact    9060
atgtggcctg ggcccccaga tgtgctttct cccaggctct ggacagtttt atacacccc    9120 tccaggtccc acagatttac aggccactaa cccgggttcc ctaattttaa agacgaagcc    9180
cttggtccgt ggtggtcgcg ctgaccaatt tgcctggctc cccaggatgt ggacagtgcc    9240
ttttccacat ttaggcattg tttccaaaac aagtggaact ttcccgcata attttgaata    9300
ttaactccag ggtctcctaa gcttactgtt tccgcacac gtccgcccca ttccgcgccc     9360
ccccacccca ccccgcgcc ccttcccgtt cacctcagca tgggacattt gctgttgggt     9420
cccgcaaatc tattcacact aacctggggtt ccctaaactt tacacgttga atcccaagtc    9480
cctcatgaca ctcagcaggg ctggaaggtt ggaaccctca gagtatgaaa attgcttccc    9540
ataccttccc ccaaattcgg tcattacacc cagagcatgt tgaatccttt tctgaatcat    9600
aaacgacctg ccctctgatt gtctgagttt cataaaatgg agggatttcc ccagtgattc    9660
cccaaagcta ttgagaatgt tgtgggtgtg tgagtcacaa gctttgggg cattaacgtc     9720 tatgctctta tatgctgcct ggccacgaat caggtcccttt aagatgtaga cagtgccacc   9780
caggtccctg gagcacactg agcagttacc aggaggtgct caagtgtgac ccaggattct    9840
ccaggtcccc ccaaatcaca cagggtctcc cgggtccctc tgggctacac caagcacaaa    9900
aggacccctt gggcagagcc tactttatt tctgttatgc caggtgttgc taacggcccc     9960
agttcccaaa cattccgagc actttctctg catcacaaca tattgactat aaacaattc    10020 tctgggtccc aggagcttca taacaagaat cttgcttttc taaaattcag gcattggtct   10080
gaaaccccaa cggccaggat cacactggac ccttttcctg gtcccccata cttggatgtt   10140
ctggacgctg ccctccaggc cctctaggaa cattcagcat tgccctcgga tcacaggaca   10200
gcactgattt cttgggctcc aaacaaccca ctgagtcatc tcaaagttaa gcaatatttc   10260
cttcaaacac actgcacact ccctatcaca aaatctgaaa attcctaagt cctaagacct    10320
aggaattctg aatccccttt cttttaaaatg tacatatgga ccccccaagtc ctccaaggac  10380 tctgagcaac ttccctagat ctttagattc aaaaacgatt ttcctggagc ccccaaattg    10440
cggtattgtc tcccagcctt ccaaagcaaa ttgagatttt tttcccttca caaaacaatt    10500
gaggtttttt ttttttttaa tactgattta tgagtctcct gacttatgg tccctgccct     10560 gggtccccct acatttagaa aatgttccat ggaccccccaa agcacactaa aaaatgtccc   10620
tgggtcccaa gaaatcccag gcatggaaaa acctgcgacc tataagtttc ctagctacta    10680
actaggtttc cagaaattta gatatcaaat ctccattggg taatttccat gtgtcccaaa    10740
aacttgaaat gtgtttcact ggggctcccc caaatgcaga cgacatccag gaaaatatat   10800 agtcttttc ttatttacca aaaataagct aatggaaatc atttaaaaat tagcatagaa    10860
aaataatact gattttttat tttttatttt tttatttgc ttccccaaa tgtactgatc     10920
```

```
acactccagg ctcccccaaa atctagacag tgctttcttc catctctgaa gggtgttaaa    10980
acctttccct gaagccacag taattatgaa ggttattttt tccccggctg ctgccagcgt    11040
ccaggccact aacttatatt cttaagatgt gaaaattaat ctcagcttcc ccctaacaca    11100
ccaagaatgt gtttggatcc ccaaaatgtg ttccttgctt tcatctgcca attttacgta    11160
atatggctct acggcaaaat tcccaatttc atatggagaa ttttctttaa ctacccctcc    11220
tcacaaattg gtcccccaag ctagctggcc cctatttgag acctctttct ctatgttccc    11280
aattgcatgg agcaacttct ctcatccccc aaacctgtaa tctatttttc tggagtctcg    11340
agtttagtca ttaatcacgg ttcccacatt aacggagtcc ccggggtccc ctcctccagg    11400
acacccattc gctaagcccg caaggcagaa agaactctgc cttgcgttcc ccaaaatttg    11460
ggcattgttc ccggctcgcc ggccacccac tgcagcttcc ccaaccccgc gcacagcggg    11520
cactggtttc gggcctctct gtctcctacg aagtccccag agcaactcgg atttgggaaa    11580
tttctctcta gcgttgccca aacacacttg ggtcggccgc gcgccctcag gacgtggaca    11640
gggagggctt cccgtgtcc aggaaagcga ccgggcattg cccccagtct cccccaaatt    11700
tgggcattgt cccgggtct tccaacggac tgggcgttgc tcccggacac tgaggactgg    11760 ccccgggtc tcgctcacct tcagcagcgt ccaccgcctg ccacagagcg ttcgatcgct    11820
cgctgcctga gctcctggtg cgcccgcgga cgcagcctcc agcttcgcgg tgagctcccc    11880
gccgcgccga tcccctccgc ctctgcgccc ctgaccggct ctcggcccgc atctgctgct    11940
gtcccgccgg tgctggcgct cgtctccggc tgccgccggg gaggccggcg tggggcgcgg    12000
gacacgcctg cggacttgcg gctggcggct gcgctcgctc ctgctgggcg ccccgaaatc    12060
cgcgccactt tcgtttgctc attgcaaaga tctcattcgt ggggaaagcg gctggagggt    12120
cccaaagtgg ggcgggcagg gggctgggc gaggacgcg gaggagaggc gctcccgccg    12180
ggcggtaaag tgcctctagc ccgcgggcct aggactccgc cgggaggcgc gcgcggagcg    12240
cgggcgaagt gattgatggc ggagcgaggg gggcgagggg ggccaggggg gcgcgagatt    12300
ccgccggcgg cccttcccc ttggctaggc ttaggcggcg gggggctggc ggggtgcggg    12360
attttgtgcg tggttttga cttggtaaaa atcacagtgc tttcttacat cgttcaaact    12420
ctccaggaga tggtttcccc agaccccaa attatcgtgg tggcccccga gaccgaactc    12480
gcgtctatgc aagtccaacg cactgaggac ggggtaacca ttatccagat attttgggtg    12540
ggccgcaaag gcgagctact tagacgcacc ccggtgagct cggccatgca ggtaggattt    12600
gagctgtgtt tcccgccctg atcctctctc tctggcggc cggagcctcc gtaggctcca    12660
agcctggccc agattcggcc cggcgcagcc ggccttccgc gcgtcccgca cctggcgggg    12720
gctccggggc tccggcgcgg caccgggggg cgctcgggat ctggctgagg ctccaagcgc    12780
cgcgtggccg gctccttctg ctgggcagg tggcggctgc gcgccccgcc cgagcccagg    12840 ggcccctca gccgcaacaa ccagcaagga ccccccgact cagcccccaag ccacctgcat    12900 ctgcactcag acgggcgca cccgcagtgc agcctcctgg tggggcgctg ggagcccgcc    12960 tgccctgcc tgccccggaga ccccagctca cgagcacagg ccgcccgggc accccagaaa    13020
cccgggatgg ggccctgaa ttctctagaa cgggcattca gcatggcctt ggcgctctgc    13080
ggctccctgc ccccacccca gcctcgcccc cgcgcacccc ccagccnnnn nnnnnnnnnn    13140
nnnnnnnnnn nnnnnnnnnn nnnnnnnnnn nnnnnnnnnn nnnnnnnnnn nnnnnnnnnn    13200
nnnnnnnnnn nnnnnnnnnn nnnnnnnnnn nnnnnnnnnn nnnnnnnnnn nnnnnnnnnn    13260
nnnnnnnnnn nnnnnnnnnn nnnnnnnnnn nnnnnnnnnn nnnnnnnnnn nnnnnnnnnn    13320
```

```
nnnnnnnnnn nnnnnnnnnn nnnnnnnnnn nnnnnnnnnn nnnnnnnnnn nnnnnnnnnn    13380
nnnnnnnnnn nnnnnnnnnn nnnnnnnnnn nnnnnnnnnn nnnnnnnnnn nnnnnnnnnn    13440
nnnnnnnnnn nnnnnnnnnn nnnnnnnnnn nnnnnnnnnn nnnnnnnnnn nnnnnnnnnn    13500
nnnnnnnnnn nnnnnnnnnn nnnnnnnnnn nnnnnnnnnn nnnnnnnnnn nnnnnnnnnn    13560
nnnnnnnnnn nnnnnnnnnn nnnnnnnnga ggccagcgag gcccgcgcgg gccctgggcc    13620
gcgggctggc gcgactataa gagccgggcg tgggcgcccg cagttcgcct gctctccggc    13680
ggagctgcgt gaggcccggc cggccccggc ccccccttc cggccgcccc cgcctcctgg     13740
cccacgcctg cccgcgctct gcccaccagc gcctccatcg ggcaaggcgg ccccgcgtcg    13800
acgccgcccg ctgcctcgct gctgactccc gtcccgggcg ccgtccgcgg ggtcgcgctc    13860
cgccgggcct gcggattccc cgccgcctcc tcttcatcta cctcaactcc ccccatcccc    13920
gcttcgcccg aggaggcggt tccccccgca ggcagtccgg ctcgcaggcc gccggcgttg    13980
tcaccccccc cgcgctcccc ctccagccct cccccccggcg cgcagcctcg ggccgctccc   14040 cctttccgcgc tgcgtcccgg agcggccccg gtgccgccac cgcctgtccc cctcccgagg   14100
cccgggctcg cgacggcaga gggctccgtc ggcccaaacc gagctgggcg cccgcggtcc    14160
gggtgcagcc tccactccgc cccccagtca ccgcctcccc cggcccctcg acgtggcgcc    14220
cttccctccg cttctctgtg ctccccgcgc ccctcttggc gtctggcccc ggcccccgct    14280 cttttctcccg caaccttccc ttcgctccct cccgtccccc ccagctccta gcctccgact   14340
ccctcccccc ctcacgcccg ccctctcgcc ttcgccgaac caaagtggat taattacacg    14400 cttttctgttt ctctccgtgc tgttctctcc cgctgtgcgc ctgcccgcct ctcgctgtcc   14460 tctctcccccc tcgccctctc ttcggccccc cccttcacg ttcactctgt ctctcccact    14520
atctctgccc ccctctatcc ttgatacaac agctgacctc atttcccgat accttttccc   14580
ccccgaaaag tacaacatct ggcccgcccc agcccgaaga cagcccgtcc tccctggaca   14640
atcagacgaa ttctcccccc cccccaaaa aaaagccatc ccccgctct gccccgtcgc     14700 acattcggcc cccgcgactc ggccagagcg gcgctggcag aggagtgtcc ggcaggaggg    14760
ccaacgcccg ctgttcggtt tgcgacacgc agcaggagg tgggcggcag cgtcgccggc     14820
ttccaggtaa gcggcgtgtg cgggccgggc cggggccggg gctggggcgg cgcgggcttg    14880
cgccggacgc ccggcccttc ctccgcccgc tccggcccg gggcctgcgg ggctcggcgg     14940
ggcggctgag cccgggggg aggaggagga ggaggaggag gacggacggc tgcgggtccc    15000
gttccctgcg cggagccccg cgctcaccct ggcggcggag ctgggggtgg ggtggggggcg   15060 tcgggaaggg ccgagggagg tgtgaggtgt ctgcagggggc gacttcccgg tcggtctgtg    15120
ggtgcagggg gtgccgcctc acatgtgtga ttcgtgcctt gcgggccctg gcctccgggg    15180
tgctgggtaa cgaggagggg cgcggagccg cagaagccca ccctggtatg ttgacgcggt   15240
gccagcgaga ccgcgagagg aagacgggggg tgggcggggc caggatggag aggggccgag   15300
ttggcaggag tcatggcaga cgccacattc gcgacatctc ccccacaccc cctctggctc    15360
tgtccgcaac atttccaaac aggagtcccg ggagaggggg agaggggctg ctggtctgag    15420
gctaagaagg gcagagcctt cgacccggag agaggccgcg gccctgccc agtgggcagc     15480 gtggaagttt ccatacaagg aggtgggaag agaccccccc ccccccttcac tgccctgtgc   15540 agagatgagc cggggggtgca ggatgggagc ccatggcact tcgctacggg atggtccagg   15600
gctcccggtt ggggggtgcag gagagaagag actggctggg aggaggggaga gggcgggagc   15660 aaaggcgcgg gggagtggtc agcagggaga ggggtgggggg gtagggtgga gcccgggctg   15720
```

```
ggaggagtcg gctcacacat aaaagctgag gcactgacca gcctgcaaac tggacattag   15780
cttctcctgt gaaagagact tccagcttcc tcctcctcct cttcctcctc ctcctcctgc   15840
cccagcgagc cttctgctga gctgtaggta accagggctg tggagtgagg accccgctg    15900 ccatcccact ccagcctgag gcagggcagc aggggggcacg gcccacgcct gggcctcggg  15960
ccctgcagcc gccagcccgc tgcctctcgg acagcacccc cctcccctct tttcctctgc   16020
ccctgccccc acctggtctc tgctccctca cctgctcctt cccttctgt tccttccctt    16080 cggccccctc cttcccagc tcagggcttt tcctgggccc tcacctgctc cgcaccgctg    16140
catgcttcct gtcctgcttt ctgccggtcc cctgacccgg acctccaagt tcagagtggt   16200
ggggcttgtt gcggaagcgc ggcgagggct agagtggcca gctggcggag tgtgctctta   16260
gaatttggaa gggggtggca gagggggcgg tgagaggact ggccagggtc cagtcaagga   16320
gatgaccaag gaggctttca gatcctcggc gcagctgccc actagtcttt agagagggca   16380
tgcaaagttg tgcttctgtc ccactgcctg ctcagtcgct cacataattt attgcatcaa   16440 aaactccct gggtctgcgg agcgaaggct ggggctgccc gcctggaggg ttccaccttc    16500
tgcaggggca gggccaactt gctgtggtgg ctccccggcct cccacccccg agtgggttaa   16560 cccgccctg tggccctgca gcctgtggag ggggtgtgtc ctaagactgg cctcccttc     16620 cagattgtag tctggggaac ctggtgtcgg acttcccagg tggcctgagc tggtctctcc   16680
agctcccacg gggagagttt ggtagcgcaa atagggagat gttctggagg ccctggcct    16740 tactggttcg atttgaggcc tggaaaggag gctctgggcg tgtgtgtgtg tgtttggggg   16800
tacccaaggc agactggagt tggagaactg ggtgactggg aaaacaaggt ttctagagca   16860
tgggtggcgt ggttgtgtta accattggag tccttgaccc aggcctggct cagctgcaga   16920
ctggaaaggt ggaaaagcca gggggagggg cgggctggc ccagcaggac tggcctgctg    16980 cttttgagggc gatggtcctc ctggaccccc cctgctcagc tgggggttgt gggaggaag   17040 ggactggtcc tcctggatgc acatgctctg taggggtggg gctgtctgcc atcttggctg   17100
gcgctggagg cctgagaagt ggcgatgtga cgctgggctg gccctgcccc catggtgtca   17160
taggacggag gccaggtcgg gtgtccagcc tgggcccctg cagctgtgga tgccgctgag   17220
ctcctgcaat aatgaccgtg gagatggtca cccctcgtgt aaaattacta gtgcttcttg   17280
caaatggaag gaactgggcc ttttctgtgt gcttctggac gcttcattct gcacatggcc   17340
ctgcgccctc acctcggcat tatgacctgt gtgttacttt tgtaataaaa ataatgttta   17400
taggaaagcc gtgcttttcaa ttttcaactg aatttgtagg ttggcaaatt tggtttggga   17460
ggggcacctc tggcctgggg cttggcctgg ctgccccgct cacgccactt ctctcccgcc   17520
cccagacacc aatgggaatc ccaatgggga agtcgatgct ggtgcttctc accttcttgg   17580
ccttcgcctc gtgctgcatt gctgcttacc gccccagtga ccctgtgc ggcggggagc     17640 tggtggacac cctccagttc gtctgtgggg accgcggctt ctacttcagt aagtagctgg   17700 gagggggcttc ctcagacctg gtcaggcccc tagagtgacc ggtgaggacg cccaacctca   17760
agccagggga gcacactcct aggtcagcag cccagccgct tgctctgaga ctttgacctt   17820
cccgccgcgt ttctgagcac gtgcggtgtc cagggcatc cacaccagct gccttttccca   17880 tcacacgcct ccttcgaagg gtgggccaga ggtgccccct agacgtcagg ggcactcaca   17940
ggggtctccc tgggcatcag aatttctgtt ggggccgtg aggctcctgc tcctgaggca   18000
ccgcacgcct agtgcagggc ttcaggctct ggaggaagag cctgcctttc ttcctgcacc   18060
ttttggacat tctgacaagg gacgtgcgtt cggtgaatga tcagaattaa aatcaataaa   18120
```

```
gtgatttata taattaaaat caataagaca agtgcagttg gtgggtggca ggggtgagcg    18180
gtgcatgcgc ctccttgggc cccaaggctg ccgtgggggg tgcccacctg ctgacctcaa    18240
ggacgcttca gcctttcctc atgtttctct cttggttctc cagcctgggg gctggcaggt    18300
gggtgcatgg cccattgtcc ttgagacccc accccagat aggggggctg ggtggatgca     18360
gaggcaggca tggtgcctgg gcatgcctga tggggcaggg gaggggccgc tccttactgg    18420
cagaggccgc acggcttatt ccacctgaca ctcaccacgt gacatcttta ccaccactgc    18480
ttactcacgc tgtgaaatgg gctcacagga tgcaaatgca cttcaaagct tctctctgaa    18540
aagttcctgc tgcttgactc tggaagcccc tgcccgccct ggcctctcct gtgccctctc    18600
tcttgcctgc cccatttggg ggtaggaagt ggcactgcag ggcctggtgc cagccagtcc    18660
ttgcccaggg agaagcttcc ctgcaccagg cttttcctgag aggaggggag gccaagccc    18720 ccacttgggg gaccccgtg atggggctcc tgctccctcc tccggctgat ggcacctgcc     18780
ctttggcacc ccaaggtgga gccccagccg accttcccct tccagctgag cattgctgtg    18840
ggggagaggg ggaagacggg aggaaagaag ggagtggttc catcacgcct cctcactcct    18900
ctcctcccgt cttctcctct cctgcccttg tctccctgtc tcagcagctc caggggtggt    18960
gtgggcccct ccagcctcct aggtggtgcc aggccagagt ccaagctcag ggacagcagt    19020
ccctcctgtg ggggcccctg aactgggctc acatcccaca cattttccaa accactccca    19080
ttgtgagcct ttggtcctgg tggtgtccct ctggttgtgg gaccaagagc ttgtgcccat    19140
ttttcatctg aggaaggagg cagcagaggc cacgggctgg tctgggtccc actcacctcc    19200
cctctcacct ctcttcttcc tgggacgcct ctgcctgcca gctctcactt ccctcccctg    19260
acccgcaggg tggctgcgtc cttccagggc ctggcctgag ggcaggggtg gtttgctccc    19320
ccttcagcct ccgggggctg gggtcagtgc ggtgctaaca cggctctctc tgtgctgtgg    19380
gacttccagg caggcccgca agccgtgtga gccgtcgcag ccgtggcatc gttgaggagt    19440
gctgtttccg cagctgtgac ctggccctcc tggagacgta ctgtgctacc cccgccaagt    19500
ccgagaggga cgtgtcgacc cctccgaccg tgcttccggt gagggtcctg ggccccttc     19560 ccactctcta gagacagaga aatagggctt cgggcgccca gcgtttcctg tggcctctgg    19620
gacctcttgg ccagggacaa ggaccctgtga cttccttgct tgctgtgtgg cccgggagca    19680
gctcagacgc tggctccttc tgtccctctg cccgtggaca ttagctcaag tcactgatca    19740
gtcacagggg tggcctgtca ggtcaggcgg gcggctcagg cggaagagcg tggagagcag    19800
gcacctgctg accagcccct tcccctccca ggacaacttc cccagatacc ccgtgggcaa    19860
gttcttccaa tatgacacct ggaagcagtc cacccagcgc ctgcgcaggg gcctgcctgc    19920
cctcctgcgt gcccgccggg gtcacgtgct cgccaaggag ctcgaggcgt tcagggaggc    19980
caaacgtcac cgtcccctga ttgctctacc cacccaagac cccgcccacg ggggcgcccc    20040
cccagagatg gccagcaatc ggaagtgagc aaaactgccg caagtctgca gcccggcgcc    20100
accatcctgc agcctcctcc tgaccacgga cgtttccatc aggttccatc ccgaaaatct    20160
ctcggttcca cgtcccctg gggcttctcc tgacccagtc ccgtgcccc gcctccccga      20220 aacaggctac tctcctcggc cccctccatc gggctgagga agcacagcag catcttcaaa    20280
catgtacaaa atcgattggc tttaaacacc cttcacgtac cctccccca aattatcccc     20340 aattatcccc acacataaaa aatcaaaaca ttaaactaac cccttcccc ccccacaac      20400 aaccctctta aaactaattg ctttttaga aacaccccac aaaagctcag aaattggctt     20460
taaaaaaaac aaccaccaaa aaaaatcaat tggctaaaaa aaaaaagtat taaaaacgaa    20520
```

```
ttggctgaga aacaattggc aaaataaagg aatttggcac tccccacccc cctctttctc   20580
ttctcccttg gactttgagt caaattggcc tggacttgag tccctgaacc agcaaagaga   20640
aaagaaggac cccagaaatc acaggtgggc acgtcgctgc taccgccatc tcccttctca   20700
cgggaatttt cagggtaaac tggccatccg aaaatagcaa caacccagac tggctcctca   20760
ctcccttttc catcactaaa aatcacagag cagtcagagg gacccagtaa gaccaaagga   20820
ggggaggaca gagcatgaaa accaaaatcc atgcaaatga aatgtaattg gcacgaccct   20880
cacccccaaa tcttacatct caattcccat cctaaaaagc actcatactt tatgcatccc   20940
cgcagctaca cacacacaac acacagcaca cgcatgaaca cagcacacac acgagcacag   21000
cacacacaca aacgcacagc acacacagca cacagatgag cacacagcac acacacaaac   21060
gcacagcaca cacgcacaca cacatgcaca cacagcacac aaacgcacgg cacacacacg   21120
cacacacatg cacacacagc acacacacaa acgcacagca cacacaaacg cacagcacac   21180
acgcacacac agcacacaca cgagcacaca gcacacaaac gcacagcaca cgcacacaca   21240
tgcacacaca gcacacacac tagcacacag cacacacaca aagacacagc acacacatgc   21300
acacacagca cacacgcgca aacagcacac acacgaacac agcacacaca gcacacacac   21360
aaacacagca cacacatgca cacagcacac gcacacacag cacacacatg aacacagcac   21420
acagcacaca catgcacaca cagcacacac gcatgcacag cacacatgaa cacagcacac   21480
acacaaacac acagcacaca catgcacaca cagcacacac actcatgcgc agcacataca   21540
tgaacacagc tcacagcaca caaacacgca gcacacacgt tgcacacgca agcacccacc   21600
tgcacacaca catgcgcaca cacacgcaca cccccacaaa attggatgaa aacaataagc   21660
atatctaagc aactacgata tctgtatgga tcaggccaaa gtcccgctaa gattctccaa   21720
tgttttcatg gtctgagccc cgctcctgtt cccatctcca ctgcccctcg gccctgtctg   21780
tgccctgcct ctcagaggag ggggctcaga tggtgcggcc tgagtgtgcg gccggcggca   21840
tttgggatac acccgtaggg tgggcggggt gtgtcccagg cctaattcca tctttccacc   21900
atgacagaga tgcccttgtg aggctggcct ccttggcgcc tgtccccacg gcccccgcag   21960
cgtgagccac gatgctcccc ataccccacc cattcccgat acaccttact tactgtgtgt   22020
tggcccagcc agagtgagga aggagtttgg ccacattgga gatggcggta gctgagcaga   22080
catgccccca cgagtagcct gactccctgg tgtgctcctg gaaggaagat cttggggacc   22140
cccccaccgg agcacaccta gggatcatct ttgcccgtct cctggggacc ccccaagaaa   22200
tgtggagtcc tcgggggccg tgcactgatg cggggagtgt gggaagtctg gcggttggag   22260
gggtgggtgg ggggcagtgg gggctgggcg gggggagttc tggggtagga agtggtcccg   22320
ggagattttg gatggaaaag tcaggaggat tgacagcaga cttgcagaat tacatagaga   22380
aattaggaac ccccaaattt catgtcaatt gatctattcc ccctctttgt ttcttgggc   22440 atttttcctt tttttttttt ttttgttttt ttttaccccc tccttagctt tatgcgctca   22500
gaaaccaaat taaaccccccc ccccatgtaa caggggggca gtgacaaaag caagaacgca   22560
cgaagccagc ctggagacca ccacgtcctg ccccccgcca tttatcgccc tgattggatt   22620 ttgttttttca tctgtccctg ttgcttgggt tgagttgagg gtggagcctc ctgggggca   22680 ctggccactg agccccttg gagaagtcag aggggagtgg agaaggccac tgtccggcct   22740
ggcttctggg gacagtggct ggtccccaga agtcctgagg gcggaggggg gggttgggca   22800
gggtctcctc agtgtcagg agggtgctcg gaggccacag gaggggggctc ctggctggcc   22860 tgaggctggc cggaggggaa ggggctagca ggtgtgtaaa cagagggttc catcaggctg   22920
```

```
gggcagggtg gccgccttcc gcacacttga ggaaccctcc cctctccctc ggtgacatct   22980
tgcccgcccc tcagcaccct gccttgtctc caggaggtcc gaagctctgt gggacctctt   23040
gggggcaagg tggggtgagg ccggggagta ggaggtcag gcgggtctga gcccacagag    23100
caggagagct gccaggtctg cccatcgacc aggttgcttg gccccggag cccacgggtc    23160 tggtgatgcc atagcagcca ccaccgcggc gcctagggct gcggcaggga ctcggcctct   23220
gggaggttta cctcgccccc acttgtgccc ccagctcagc cccctgcac gcagcccgac    23280 tagcagtcta gaggcctgag gcttctgggt cctggtgacg gggctggcat gaccccgggg   23340
gtcgtccatg ccagtccgcc tcagtcgcag agggtccctc ggcaagcgcc ctgtgagtgg   23400
gccattcgga acattggaca gaagcccaaa gagccaaatt gtcacaattg tggaacccac   23460
attggcctga gatccaaaac gcttcgaggc accccaaatt acctgcccat tcgtcaggac   23520
acccacccac ccagtgttat attctgcctc gccggagtgg gtgttccgg gggcacttgc    23580 cgaccagccc cttgcgtccc caggtttgca gctctcccct gggccactaa ccatcctggc   23640
ccgggctgcc tgtctgacct ccgtgcctag tcgtggctct ccatcttgtc tcctcccgt    23700 gtccccaatg tcttcagtgg ggggcccct cttgggtccc ctcctctgcc atcacctgaa    23760 gaccccacg ccaaacactg aatgtcacct gtgcctgccg cctcggtcca ccttgcggcc    23820
cgtgtttgac tcaactcaac tcctttaacg ctaatatttc cggcaaaatc ccatgcttgg   23880
gttttgtctt taaccttgta acgcttgcaa tcccaataaa gcattaaaag tcatgatctt   23940
ctgagtgttc cactctctga cttgggtact ggactgccag agggagggaa ggggctgagc   24000
acctggaagc aggcagaggg ggatagaaga gggaagggga aggaaggcct tagggggtgtg  24060 gacacctctc tccgtcccct gatcacatac atggagaaat gagagagctg gaagccagac   24120
tctcagactc actgtcgtgc acctgaagcc aggggggtctg gacagtgtc aggcaccaag   24180 ttctcaaaga tggggggtgcc acgaagggta ggagcctggg gggcttttc agagaaaaag    24240 caaagtacca tcagtaccaa ctccagggaa tgcctccccc accaacagcc ttagaggact   24300
ggggctgggc aacctctaaa aggttctgga aaccgtatct gtggctggag atgggggctc   24360
agggccactc tcacccaggg actcagcccc cttccaaggt tgaggctgcc cagatgtcat   24420
tagtaccact gcctcctgcc agggctcagc ctgtacccac ctgtcccaag ggtgctggcc   24480
tctagctttc aagggtccct gagcatggga ggaggggtag gctgggctgc tgggagcctg   24540
gcccagcctc ttctctccat cccctccag gaactttcca gcagccttgg gcagtggatc    24600
tgcctgtgcc ccgcctgctg tggggatgga gggacagggg cgccacagaa ggagcccaga   24660
agtgtgccca gggccctgca gccttcagtg ctgggcaggc ggtggggagg ggcctgactg   24720 ggttggggc gtgcttgcat cctggccccc agggtctgcc cctggtcaag ccctgtccct    24780
tgatggctgc ctctgtccct agcatttctc ctgtgccggg cactggaggg tgctgggctg   24840
tcacccaagc ctctgaggcc tggggacacg tctacacgga cagtgtcact gcccacacca   24900
tctgagaacc actccaaggg aagggagagg gtgggcggtg gtttggggag ttgcctggag   24960
gaggagggat tagccttgaa gatgaggagg gctgggggtt ggagaagagc agattggata   25020 tgggggggcac catgcccttc ctgagctggt ccctggctct gcacctcagt gctaggtcta   25080
agctggaggg tccagggccc aggtggcatt gctgaccccc agggggtcgg ggctgctctg   25140
aggcccttct gtagatgtag atggaagcct agtcctgtcc accttcctga ggccaggtgg   25200
agttgctttc cctgcaagcc caggcagctc tgccctgtgc cctccccca gccctgcagt    25260 cccccaggcc cacgcagggc cggcctcatg gtctcgcttc ctctctgggt ctgcttcagg   25320
```

```
gcccagcctc cagccccatg agcctgggcc ctcctgctcc tgtccccact ggccccaggt    25380
cacttccaca ctggctctcc ccgcaccctg ggcctgctca gccactcttg cccacagcca    25440
ggagcttctg tgcagcttct ttcctttcac ttgcagcctg cctgccctct gcttccccgg    25500 acccttgtg accttccctg acctctctgc agaactgggc aaagccactc accctggttc      25560
ccccgggttt agcctggtct cttgacaccc actcagggct gcccagcctt catcctgctt    25620
cactgggccc agcctcattc cagggcttct gagactgcag ggccctctct tctcccctct    25680
ccctgctttg caaattctca gttcatcctg gcagctccaa ctctccatcc ctccacccat    25740
ccatccaacc atccctccac ccatccctcc actcatccat ccactcatcc ctccacccat    25800
cccctaccca tccagccacc catccatcca cccatccctc cacccatcca tccacccatc    25860
cctccaccca tccatccaac catccaacca cccatccctc cacccatcca tccacccatc    25920
cctccaccca tccacttacc cactcattca ccaactcatc catccactgg tccatctgcc    25980
caccaaacca tccactcacc atccacccat tcacctattt atccatccca tccacccact    26040
taccactcac tcacccactc atccatccat ttactcaccc ctccatccac ccacccactc    26100
atccatctat tcttccaccc actcacccac tcactcaccc acgcacccat tcacccatct    26160
attcatccac ccacccaacc atccactcac ccacccatcc acctattcat ccatcccatc    26220
cacaaacacc ccacctacta ctcactcacc cactcattca tccatttact taccccctcca   26280 cccatccacc cattcatcca tctattcatc catcccatct acccactcac ccacttaccc    26340
agtctcaccc actcatccat ccacccatct attcgtccac ccaacagtcc acccacccac    26400
ccatccactc acccatccat ccacctattc atccatccca cccacccact cacccactta    26460
tccactcact cacgcactca tccatccatc cactcaccct cccatctacc catccactca    26520
tctatccatc tacccactcg cccactcatc atccacccac tcacccactt acccacaaac    26580
tcacccactc atccatccat ccactcaccc tcccatccac ccacccagtc atctatccat    26640
ctacccattc acccacttac ccactcactc acccactcat ccatccatcc acgcaccctc    26700
catccaccca cccactcatc tatctactca cctgtccatc cacccactta actctcactc    26760
acccactcat ccatccatcc actcaccctc catccactca cccagtcatc tatctattca    26820
tctgtccatc cacccactca cccacttacc tctcactcgc ccactcatcc atccatccac    26880
tcaccctcca tccacccacc cactcatcta tctattcatc tatccatcta cccactcacc    26940
cacttaccca ctcacccact catccatcca tccactcacc ctccatccac ccacccagtc    27000
atctatctat tcatctatcc atctatccac tcacccactt acctctcact cgcccactca    27060
tccat                                                                 27065
```

GENOME CAPTURE AND SEQUENCING FOR COMPREHENSIVE CHROMATIN STRUCTURE MAPS IN COMPLEX GENOMES AND CANCER PROGRESSION

CROSS-REFERENCE TO RELATED APPLICATIONS

This nonprovisional application is a continuation-in-part of and claims priority to U.S. Nonprovisional patent application Ser. No. 14/600,773, entitled "Genome Capture and Sequencing for Comprehensive Chromatin Structure Maps in Complex Genomes and Cancer Progression," filed Jan. 20, 2015 by the same inventor, which claims priority to U.S. Provisional Patent Application No. 61/928,473, entitled "Genome Capture and Sequencing to Determine Genome-Wide Copy Number Variation," filed Jan. 17, 2014 by the same inventor, both of which are incorporated herein by reference in their entireties.

RELATED PATENTS/APPLICATIONS

This nonprovisional application is related to U.S. Pat. No. 8,728,979, entitled "Method for Identifying Cells Based on DNA Replication Domain Timing Profiles," filed Aug. 28, 2008; U.S. Nonprovisional patent application Ser. No. 13/479,686, entitled "Genome-Scale Analysis of Replication Timing," filed May 24, 2012; U.S. Pat. No. 9,245,090, entitled "Fingerprint for Cell Identity and Pluripotency," filed Aug. 27, 2012; and U.S. Nonprovisional Pat. No. 8,725,423, entitled "Replication Timing Profiles for Leukemia and Other Cancers," filed Dec. 26, 2012, all of which are incorporated by reference in their entireties.

BACKGROUND OF THE INVENTION

1. Field of the Invention

This invention relates, generally, to genome capture and sequencing. More specifically, it relates to chromatin structure maps in complex genomes and cancer progression.

2. Brief Description of the Prior Art

Despite the central role of chromatin as the ultimate substrate for all nuclear events, the structure of chromatin remains poorly characterized. The human genome is packaged into chromatin, whose fundamental subunit is ~147 bp of DNA wrapped around a histone octamer to form the nucleosome [Kornberg, R. D. & Lorch, Y. Twenty-five years of the nucleosome, fundamental particle of the eukaryote chromosome. Cell 98, 285-294 (1999)]. The location and density of nucleosomes with respect to the underlying DNA sequence is an important factor in determining access to the genome for DNA-templated processes [Agalioti, T. et al. Ordered recruitment of chromatin modifying and general transcription factors to the IFN-beta promoter. Cell 103, 667-678 (2000); Jiang, C. & Pugh, B. F. Nucleosome positioning and gene regulation: advances through genomics. Nat Rev Genet 10, 161-172 (2009); Stedman, E. Cell specificity of histones. Nature 166, 780-781 (1950)]. Little is known regarding the precise role of nucleosome distribution in these processes, because there have been relatively few studies measuring the distribution of nucleosomes across the genome in multiple cell types and physiological contexts.

Genome-wide nucleosome distribution information is critically important for understanding genomic processes, yet this information is lacking for a variety of human cell states. Genome-wide measurements of the locations of genome binding factors by Chromatin immunoprecipitation (ChIP), polymorphisms by exome sequencing, or DNA methylation by bisulfite conversion, have become routine and robust assays of genomic structure and organization. A literature search on any of these assays returns thousands of results, while searches on "nucleosome distribution" returns an order of magnitude fewer results. Only a handful of seminal papers have measured genome wide human nucleosome positions in a limited number (1-2) of cell states [Gaffney, D. J. et al. Controls of nucleosome positioning in the human genome. PLoS Genet 8, e1003036 (2012); Schones, D. E. et al. Dynamic regulation of nucleosome positioning in the human genome. Cell 132, 887-898 (2008); Valouev, A. et al. Determinants of nucleosome organization in primary human cells. Nature 474, 516-520 (2011); Yuan, G. C. et al. Genome-scale identification of nucleosome positions in *S. cerevisiae*. Science 309, 626-630 (2005)]. Indeed, there has been no study of nucleosome distribution in primary patient tumor samples representing multiple stages and grades of both lung adenocarcinoma (LAC) and colorectal cancer (CRC).

A complete understanding of the distribution of nucleosomes across the genome in cancer is currently lacking, yet it is critically important for understanding cancer etiology in basic biological and clinical contexts. It was previously shown that extensive nucleosome distribution changes at a subset of genes in patients with low-grade LAC [Druliner, B. R. et al. Chromatin patterns associated with lung adenocarcinoma progression. Cell Cycle 12, 1536-1543 (2013)]. Mononucleosomally protected DNA was isolated from patient derived primary LAC tissue and used to query high-resolution tiling microarrays. These microarrays were custom-designed to measure nucleosome distribution changes at the 2000 bp surrounding the transcription start site (TSS) of ~900 cancer- and immunity-related genes. However, those studies were limited in the breadth of loci studied by the number and density of probes that it was possible to print on the microarray.

Accordingly, what is needed is a robust, cost-effective, paired-end targeted sequencing-based nucleosome distribution mapping platform to analyze chromatin structure at the TSSs of every open reading frame in the human genome. However, in view of the art considered as a whole at the time the present invention was made, it was not obvious to those of ordinary skill in the field of this invention how the shortcomings of the prior art could be overcome.

While certain aspects of conventional technologies have been discussed to facilitate disclosure of the invention, Applicants in no way disclaim these technical aspects, and it is contemplated that the claimed invention may encompass one or more of the conventional technical aspects discussed herein.

The present invention may address one or more of the problems and deficiencies of the prior art discussed above. However, it is contemplated that the invention may prove useful in addressing other problems and deficiencies in a number of technical areas. Therefore, the claimed invention should not necessarily be construed as limited to addressing any of the particular problems or deficiencies discussed herein.

In this specification, where a document, act or item of knowledge is referred to or discussed, this reference or discussion is not an admission that the document, act or item of knowledge or any combination thereof was at the priority date, publicly available, known to the public, part of common general knowledge, or otherwise constitutes prior art under the applicable statutory provisions; or is known to be relevant to an attempt to solve any problem with which this specification is concerned.

BRIEF SUMMARY OF THE INVENTION

The long-standing but heretofore unfulfilled need for early detection of cancer based on nucleosome distribution and mapping is now met by a new, useful, and nonobvious invention.

In an embodiment, the current invention is a method of early detection of cancer (e.g., lung adenocarcinoma, colorectal cancer, etc.) in a grade one subject via analysis of chromatin structure, and dysregulation thereof, in a genome of the grade one subject. A biological sample is collected from a normal tissue of the subject, where the tissue is not suspected of being carcinogenic. Another biological sample is collected from a tissue of the subject, where the tissue is suspected of being carcinogenic. The normal tissue and the suspected tissue may correspond to each other via biological similarities to each other. Nucleosome distribution is quantitatively measured in each sample within a range of base pairs (e.g., about 2,000 base pairs) flanking each transcription start site in the entirety of the genome of the sample. The levels of nucleosome distribution are compared to or otherwise evaluated against each other. A difference of nucleosome distribution of about 10% or higher between the samples indicates that the suspected sample is carcinogenic. This difference cannot be seen as prevalently in later grade subjects.

The step of collecting the samples may be performed by targeting and capturing less than an approximately 5% region of the genome in each sample, such that the transcription start sites are contained in the captured region. This region may be analyzed via MNase digestion. By targeting transcription sites and capturing less than approximately 5% of the genome, the method provides an efficient and cost-effective way to measure nucleosome distribution. Accordingly, the method allows for the efficient and effective early detection of cancer by focusing on particular sections of the genome, the transcription sites, that improves upon analyzing the entirety of the genome.

In a separate embodiment, the current invention is a method of early detection of cancer (e.g., lung adenocarcinoma, colorectal cancer, etc.) in a grade one subject via analysis of chromatin structure, and dysregulation thereof, in a genome of the grade one subject. A biological sample is collected from a tissue of the subject, where the tissue is suspected of being carcinogenic. Nucleosome distribution is quantitatively measured in the sample within a range of base pairs (e.g., about 2,000 base pairs) flanking each transcription start site in the entirety of the genome of the sample. The measured level of nucleosome distribution is compared to or otherwise evaluated against a control level in a control. The suspected tissue and the control may correspond to each other via biological similarities to each other. A difference of nucleosome distribution of about 10% or higher between the samples indicates that the suspected sample is carcinogenic. This difference cannot be seen as prevalently in later grade subjects.

Prior to comparing or evaluating the measured level of nucleosome distribution to said control level, nucleosome distribution may be quantitatively measured in the control sample within a range of base pairs (e.g., about 2,000 base pairs) flanking each transcription start site in the entirety of the genome of the control sample. In this case, the control is a biological sample from an additional tissue of the subject, where the additional tissue of the grade one subject is not suspected of being carcinogenic.

The step of collecting the samples may be performed by targeting and capturing less than an approximately 5% region of the genome in each sample, such that the transcription start sites are contained in the captured region. This region may be captured via MNase digestion.

In a separate embodiment, the current invention can include any one or more, or all, of the foregoing limitations.

These and other important objects, advantages, and features of the invention will become clear as this disclosure proceeds.

The invention accordingly comprises the features of construction, combination of elements, and arrangement of parts that will be exemplified in the disclosure set forth hereinafter and the scope of the invention will be indicated in the claims.

BRIEF DESCRIPTION OF THE DRAWINGS

The patent or application file contains at least one drawing executed in color. Copies of this patent or patent application publication with color drawings will be provided by the Office upon request and payment of the necessary fee.

For a fuller understanding of the invention, reference should be made to the following detailed description, taken in connection with the accompanying drawings, in which:

FIG. 1A shows workflow of the mTSS-seq method. Following MNase digestion using a titration of MNase, populations of mononucleosomally protected DNA and subnucleosomal fragments are isolated, and prepared as libraries for ILLUMINA sequencing. Solution-based sequence capture is performed using biotinylated oligos, enabling the enrichment of fragments within 2 kb of each transcription start site in the human genome. Paired-end 50 bp sequencing was then performed on each index. In FIG. 1B, qPCR following mTSS-seq shows ~1:500 enrichment for the target regions (2 kb surrounding TSS) compared to or otherwise evaluated against the off-target regions (outside the 2 kb surrounding the TSS). Selected genes; ATM (an example of which is depicted as SEQ ID NO:15 in the sequence listing), RHOC and ITGA4 for both the pre-capture pooled total library and the sequence captured pooled library are shown, Ct values are on the y-axis. FIG. 1C shows distribution of mTSS-seq fragment sizes following sequencing, determined after mapping to the human genome. The fragments for all samples (n=8 genomes: 4 patients, matched normal-tumor) peak at ~150 bp, as expected for MNase protected DNA. Fragment sizes were inferred from the separation of adaptors after paired-end sequencing. FIG. 1D depicts alignment of the mTSS-seq midpoints to the human genome using the UCSC genome browser for LAC patient #4137. Normal tissue is shown for chr11, hg19 (UCSC Genome Browser). Zooming in twice at 100× allows for further visualization of the sequence capture oligos surrounding the TSS in a 500 kb and a 5 kb region showing the ATM locus.

FIG. 2A shows averaged, normalized reads per million (y-axis) from mTSS-seq plotted as fragments (gray) and midpoints (black), centered on and surrounding 2 kb of the TSS for all open reading frames in hg19 (x-axis). DNase I-hypersensitivity (GSM736580; green) and RNA polymerase II from ChIP-seq (GSM935299; blue) data from A549 cells. FIG. 2B shows nucleosomal dinucleotide composition shown for LAC patient #4137 Normal for fragments of sizes 151-152 bp, with a 130 bp window. The x-axis is the distance from the nucleosome midpoint (center indicated by solid black vertical line). The blue line is the A/T containing dinucleotide frequency and the red line is the G/C containing dinucleotide frequency. FIG. 2C shows an LAC patient 4137 Normal nucleosomal midpoints (blue track) plotted in the UCSC genome browser against the published human lymphocyte nucleosome distribution maps by Gaffney et. al. (green track) for the ZNF451 and CCDC197 loci. Sequence capture oligos and corresponding RefSeq gene models are shown for each locus. Correlations are shown for ZNF451 and CCDC187, respectively. FIG. 2D depicts nucleosome distribution maps from a previously published (by the current applicant) microarray analysis in these patients showing identical regions of change to those determined by mTSS-seq. Frequency distributions of midpoint data for LAC patient #4137 Normal (top panel in microarray section; and black line in mTSS-seq section) and Tumor (bottom panel in microarray section; and red line in mTSS-seq section) were plotted in the UCSC genome browser with respect to the 2 kb surrounding the transcription start site of the ATM gene (USC Genome Bioinformatics). The y-axis indicates the number of aligned reads. The track marked 'Microarray' shows intensity values for MNase digested mononucleosome DNA compared to bare genomic DNA, hybridized to a tiling array taken from the data set described in Druliner et al., 2013. Positive peaks in the array track are indicate the presence of positioned nucleosomes and are co-incident with 150-bp midpoints. The region of change is highlighted by a shaded red box is similar between microarray and sequencing data.

FIGS. 3A-3E show widespread nucleosome distribution changes being common among grade one patients and having specific nucleosome architectures that are enriched for specific GO processes. FIG. 3A shows heatmaps representing Normal minus Tumor differences for each patient at each TSS in the human genome (~22,000 genes). Loci are sorted on the mean difference value across 2000 bp surrounding the TSS (white line) for all genes, ordered on the basis of each patient's corresponding normal data. The two grade one patients are on the left and the two grade three patients are on the right. Black represents areas with few differences between normal and tumor, yellow (positive values) indicates higher nucleosome occupancy in the normal and blue (negative values) indicates higher nucleosome occupancy in the tumor. FIG. 3B depicts correlation values calculated between normal and tumor for each grade one patient, and the genes in the lowest 20% (indicating change between normal and tumor) were selected (~4,300 genes each). The overlap of genes determined as changed for each grade one patients is shown, 1, 804 genes. FIG. 3C depicts correlation values for each of the common 1,804 genes plotted as boxplots for each patient, showing a range of lower correlation values in the grade one patients (left two boxplots) as compared to the range of higher correlation values in the grade three patients (right two boxplots). FIG. 3D depicts the average nucleosome occupancy and corresponding heatmaps for the Normal (black) and Tumor (red) data for grade one patient #4137, generated using k-means clustering with k=4 centered on the 1000 bp surrounding the TSS for every human gene. The four clusters contain 3,460, 7,665, 4,246 and 6,486 genes, respectively. In the average plots, the y-axis is the mean score for both normal (black) and tumor (red) data, for each cluster. The x-axis is the genomic position for both the average plots and heatmaps. In the heatmaps, white represents nucleosome depletion and black (normal) or red (tumor) represents nucleosome occupancy. It was determined that the majority of the 1,804 genes identified FIG. 3B belonged to clusters 1 and 4. FIG. 3E shows the enrichment of genes in each cluster for an ontologic process. The four processes most overrepresented by genes are shown for each cluster with corresponding P-value.

FIG. 4A shows average nucleosome distribution of normal tissue (black) and tumor tissue (red) for grade one patients (#4137 and #1357) and grade three patients (#873 and #386) for 1,804 genes shared between grade one patients. Five additional genes implicated in cancer are shown: ATM (FIG. 4B), CASC1 (FIG. 4C), CDKL2 (FIG. 4D), CCR10 (FIG. 4E), and HKR1 (FIG. 4F). The x-axis represents a 2 kb range of genomic position centered on the TSS, and the y-axis is fragments per million. Regions with most significant change in the grade one patients are highlighted in a shaded red for emphasis, while corresponding regions of no change in grade three patients are shaded in grey.

FIG. 5A shows the correlation values for the normal patient data (black) and grade one tumor patient data (red) versus the computationally predicted DNA encoded nucleosome occupancy model. The x-axis is the 1,804 genes in common between grade one patients, sorted on the correlation of the tumor data with the DNA encoded nucleosome occupancy model, and the y-axis is the Pearson's correlation coefficient from the comparison of each data set versus the computational model values. FIG. 5B shows the correlation values for the average data from the normal tissue (black) and grade three tumor tissue (red) versus the DNA encoded nucleosome occupancy. Axes are similar to those in FIG. 5A. The nucleosome distribution data for normal tissue (Normal, black lines) and grade one tumor tissue (red lines) are shown compared to DNA encoded nucleosome occupancy model scores (blue-DNA encoded, four genes) from FIGS. 4A-4F: ATM (FIG. 5C), CASC1 (FIG. 5D), CDKL2 (FIG. 5E), and CCR10 (FIG. 5F). The x-axis represents a 2 kb range of genomic position centered on TSS. The y-axis is the normalized fragments per million. Regions with most significant difference in the normal compared to the model are highlighted in a shaded red for emphasis, while corresponding regions of no change in the grade one tumor compared to the model are shaded in grey. Correlation values between the data and model are included for each gene; in all cases, the model is more highly correlated with the grade one tumors than the normal tissue or grade three tumors.

FIG. 6A shows regions of difference in grade one patients (17,565) and grade three patients (5,916), obtained by thresholding regions with a difference greater than 5. The threshold applied to determine regions of change was the most stringent cut-off that discriminated between the samples, while revealing a substantial enough number of regions to perform downstream analyses in the grade three patients since there were far less regions of change than in the grade one patients. Regions common between patients were merged so that duplicated regions were removed. 17,565 regions of difference were identified in the grade one patients and 5,916 regions in the grade three patients. FIG. 6B depicts the number of transcription factor binding sites for each region of difference in the grade one and the grade three patients, and the ratio between the observed/shuffled was calculated. The black vertical line is drawn at 1, and values above 1 represent enrichment and below 1 represent depletion of transcription factor binding sites in the regions. This analysis was performed for nine transcription factors: Ctcf (GSM803456), Bcl3 (GSM1010775), Yy1 (GSM1010794), Sin3a (GSM1010882), Taf1 (GSM1010812), P300 (GSM1010827), Creb1 (GSM1010719), Ets1 (GSM1010829) and Atf3 (GSM1010789). FIG. 6C is a Venn diagram of overlap between regions corresponding to genes between the grade one patients and grade three patients: regions unique to grade one patients, shared regions, and regions unique to grade three patients. In FIG. 6D, for each of the categories from panel C, the enrichment of transcription factor binding sites at the regions of difference was determined through the same procedure and for the same nine transcription factors from panel B. The colored boxes correspond to the categories determined from the Venn diagram in panel C. Subnucleosomal fragment data (<125 bp) for normal (black lines) and tumor (red lines) for each grade one patient #1357 and grade three patient #873 were aligned and centered on representative transcription factor data Ctcf (GSM803456) (FIG. 6E) and Creb1 (GSM1010719) (FIG. 6F) peaks from ChIP-seq in A549 cells. Additionally, nucleosome size fragment scores (130-175 bp) for normal (shaded, dashed black lines) and tumor (shaded, dashed red lines) for each patient were also aligned and centered on Ctcf and Creb1 peaks.

FIG. 7A shows nucleosome distribution plots at the ATM gene for normal (black lines) compared to matched grade one LAC tumor (as seen in FIG. 4B; red lines), and for the normal compared with matched S2, S3 and S4 CRC tumors (red lines). The x-axis represents the TSS+/−1 kb, and the y-axis is fragments per million. Regions with most significant change in the grade one patients are shaded in red for emphasis, while corresponding regions in grade three, which are unchanged between normal and tumor samples, are shaded in grey. Three other cancer-related genes are shown to illustrate the widespread nucleosome distribution changes in the progression of CRC, and concordance with LAC changes: HKR1 (FIG. 7B), NOP16 (FIG. 7C), and KIF2B (FIG. 7D). The nucleosome distribution data for normal tissue (black lines) and S3 CRC tumor tissue (red lines) are shown compared to predicted nucleosome occupancy based on DNA sequence (blue lines), for two genes from FIG. 5C and FIG. 5D: (E) ATM, and (F) HKR1. The x-axis represents the TSS+/−1 kb, and the y-axis is the normalized fragments per million. Regions with most significant difference in the normal compared to the model are shaded red for emphasis, while corresponding regions in the S3 tumor are shaded in grey. Additionally, correlation values between the data and model are included for each gene; in all cases, the model is more highly correlated with the S3 tumors than the normal tissue. In FIG. 7G, subnucleosomal fragment data (<125 bp) for normal (black lines) and tumor (red lines) for each CRC patient were aligned and as a representative centered on transcription factor data for Ctcf (GSM803456) peaks from ChIP-seq in A549 cells. Additionally, nucleosome size fragment scores (130-175 bp) for normal (shaded, dashed black lines) and tumor (shaded, dashed red lines) for each patient were also aligned and centered on Ctcf peaks.

FIG. 8A is a model describing chromatin-based hierarchical genome regulation. In this model, a superset of genomic loci is made available for licensing through transient DNA-directed nucleosome redistributions: a genomic intermediate. Loci in a physiology with the appropriate regulatory machinery will be licensed for a genomic response. Those without the regulatory machinery will not be affected. This model maximizes the potential for multiple concerted responses with a limited number of genomic architectures. However, if any point of this hierarchy is disrupted oncogenic transformation can occur. FIG. 8B shows an interpretation of these results is that regulatory factors are initially unable to bind basal nucleosome architecture (as in the normal). Inappropriate widespread nucleosome redistributions to DNA-directed positions in early tumors potentiate the binding of regulatory factors (such as transcription factors) outside of their physiological context. Nucleosomes return to their basal architecture in advanced tumors, possibly through redundant and compensatory remodeling machinery. However, the regulatory mark remains, which further contributes to the progression of cancer.

In FIG. 9A, the threshold applied to determine regions of difference was the most stringent cut-off that discriminated between the samples, while revealing a substantial enough number of regions to perform downstream analyses in the grade three patients since there were far less regions of change than in the grade one patients. Boxplots for all the difference values for grade one and grade three patients above and below the −5-5 threshold are shown. Overall, the total difference values for the grade one patients have a higher range than the values for grade three patients, showing that the grade one patients are more different overall than the grade three patients. The average nucleosome distribution averages for normal (black lines) and tumor (red lines) were plotted for genes in all categories shown. It was confirmed that for all the genes in each category—unique to grade one as in FIG. 9B, shared as in FIG. 9C, and unique to grade three as in FIG. 9D— (corresponding to 9,864, 2,008, and 2,825 genes, respectively), the average nucleosome distribution plots showed more change in the grade one patients than in the grade three patients. It was found that in all cases, the grade one patients showed a greater degree of difference than the grade three patients.

DETAILED DESCRIPTION OF THE PREFERRED EMBODIMENT

Figure 1A:
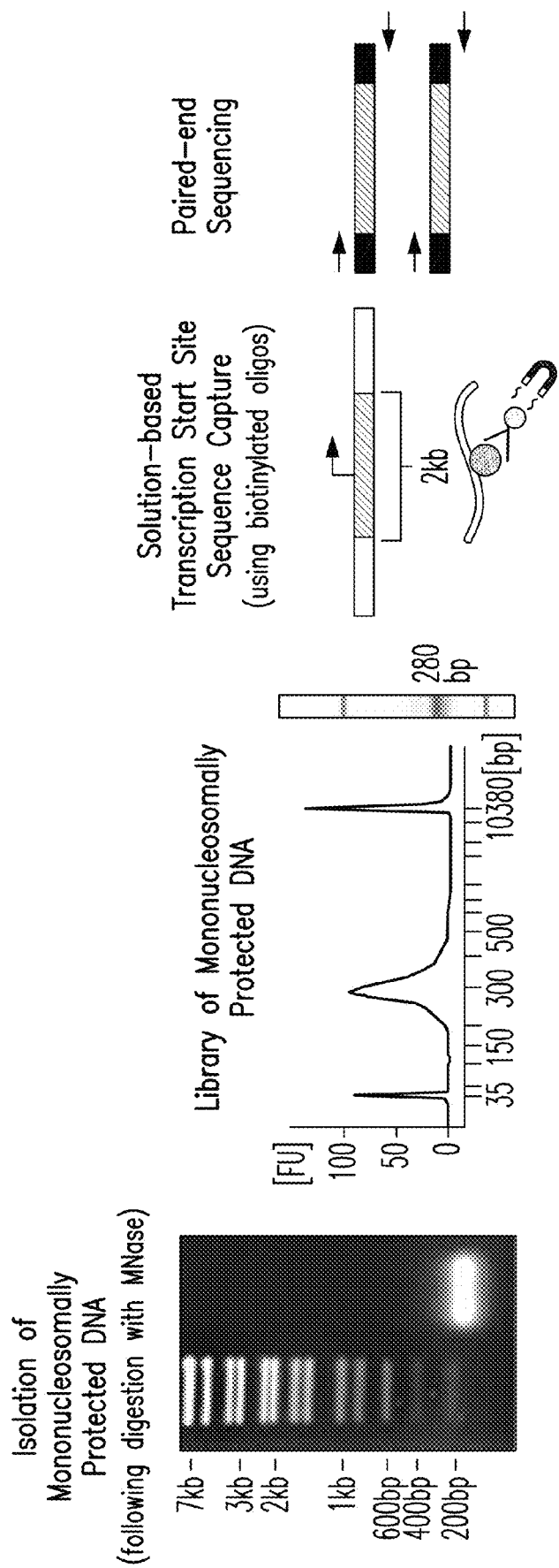
FIGS. 1A-1D depict the mTSS-capture method combined with paired-end sequencing maps genome-wide nucleosome mapping in primary patient samples.

In the following detailed description of the preferred embodiments, reference is made to the accompanying drawings, which form a part thereof, and within which are shown by way of illustration specific embodiments by which the invention may be practiced. It is to be understood that other embodiments may be utilized and structural changes may be made without departing from the scope of the invention.

As used in this specification and the appended claims, the singular forms "a", "an", and "the" include plural referents unless the content clearly dictates otherwise. As used in this specification and the appended claims, the term "or" is generally employed in its sense including "and/or" unless the context clearly dictates otherwise.

Altered chromatin structure is a strong indication of cancer, and inappropriate regulation of chromatin structure may represent the origin of transformation. Several important studies have mapped human nucleosome distributions genome-wide, but the genome-wide role of chromatin structure in cancer progression has not been addressed. A MNase-Sequence Capture method, mTSS-seq, was developed herein to map genome-wide nucleosome distribution in cancer, for example primary human lung and colon adenocarcinoma tissue. Here, it was confirmed that nucleosome redistribution is an early, widespread event in lung adenocarcinoma (LAC) and colon adenocarcinoma (CRC). These altered nucleosome architectures are consistent between LAC and CRC patient samples indicating that they can serve as important early adenocarcinoma markers. As such, this consistency would be expected in other adenocarcinomas, as well as other carcinomas. It was demonstrated that the nucleosome alterations are driven by the underlying DNA sequence and potentiate transcription factor binding. DNA-directed nucleosome redistributions are widespread early in cancer progression. A methodology was developed herein as a hierarchical model for chromatin-mediated genome regulation. Moreover, since it was demonstrated that nucleosome alterations potentiate transcription factor binding, a methodology was developed herein to target TSS, thereby eliminating the need to analyze the entire genome, representing an improvement over prior art methods. In particular, prior art methods of analyzing the genome require an analysis of 100% of the human genome, which is both costly and time-consuming. Further, in the case of cancer detection, an analysis of 100% of the human genome invariable leads to inadequate patient care due to the time and money costs associated with such an extensive analysis. However, the methodology developed herein eliminates the need to analyze 100% of the genome, and instead targets a fraction of the genome, representing a distinct improvement over prior art methods of analyzing the human genome or detecting cancer. According to the developed method, an accurate analysis may be performed by targeting and capturing less than 5% of the human genome, drastically reducing the time and money spent on analyzing nucleosome distribution. As a result of the improvements presented by the methodology, more patients may be examined to detect cancer than under prior art methods, since the method provides a targeted approach to cancer detection by analyzing 2,000 base pair regions surrounding the TSS of genes in the human genome, or less than 5% of the human genome.

In an embodiment, a solution-based sequence capture method was developed, enabling the enrichment of the 2000 bp surrounding the TSS of all open reading frames in the human genome. Due to the importance of promoter composition in gene regulation, the method was designed to map nucleosomes at the regions surrounding the TSS. This capture method reduces the sequence space of the human genome from 3.4 Gb in total to ~50 Mb of TSSs, a 98.5% reduction. Moreover, the method analyzes substantially the entirety of the genome by mapping nucleosome distribution for each gene, without the need to map 100% of the genome. This enrichment is analogous to that achieved for exome sequencing experiments [Ng, S. B. et al. Targeted capture and massively parallel sequencing of 12 human exomes. Nature 461, 272-276 (2009)]. Using this targeted enrichment of mononucleosomally-protected DNA, herein called mTSS-seq (MNase-protected DNA, transcription start site capture-sequencing), sufficiently high sequencing coverage could be achieved to determine individual nucleosome positions, at an average of ~100 reads per nucleosome, exceeding the necessary coverage for high-resolution nucleosome position mapping [Gaffney, D. J. et al. Controls of nucleosome positioning in the human genome. PLoS Genet 8, e1003036 (2012); Valouev, A. et al. Determinants of nucleosome organization in primary human cells. Nature 474, 516-520 (2011); Kent, N. A., et al. Chromatin particle spectrum analysis: a method for comparative chromatin structure analysis using paired-end mode next-generation DNA sequencing. Nucleic Acids Res 39, e26 (2011); Lee, W. et al. A high-resolution atlas of nucleosome occupancy in yeast. Nat Genet 39, 1235-1244 (2007)].

This technique represents a unique source of nucleosome distribution information at the TSS, and has not been previously executed on a genome-wide scale. The relative enrichment or reduction of sequences from this assay allows a determination of changes in nucleosome distribution among a variety of sample types. In certain embodiments, the current invention offers several advantages. It measures nucleosome distribution at all TSS in the human genome. The targeted enrichment is a cost-effective approach to whole genome studies and allows for comprehensive nucleosome distribution mapping to be completed on several samples. This nuclease protection assay is highly relevant to diffusible molecules such as transcription factors, and the paired end sequencing approach provides information on protected fragment size. This assay can therefore be used to analyze subnucleosomal-sized fragments for an additional layer of genomic regulatory information [Kent, N. A., et al. Chromatin particle spectrum analysis: a method for comparative chromatin structure analysis using paired-end mode next-generation DNA sequencing. Nucleic Acids Res 39, e26 (2011); Henikoff, J. G., et al. Epigenome characterization at single base-pair resolution. Proc Natl Acad Sci USA 108, 18318-18323 (2011)]. Using the mTSS-seq approach, nucleosome distribution was mapped with unprecedented breadth and depth in human cancer patient samples.

In an embodiment, the current invention relates to genome capture and sequencing to comprehensively map chromatin structure in complex genomes. It brings significant improvement to the ability to query the chromatin structure of select important regions of the entire human genome. This was accomplished by developing and implementing a particular sequencing strategy. A solution-based sequence capture method was developed to enable the enrichment of the 2000 bp surrounding the transcription start site of 25,464 human open reading frames. This enrichment reduces the sequence space of the human the sequence space of the human genome from 3.4 Gb in total to 50 Mb of transcription start sites, a 98.5% reduction. This enrichment is analogous to that achieved in previous exome sequencing experiments. This sequence capture approach allows for multiplexing of the chromatin structure analyses in ILLUMINA HiSeq2500 lanes, thereby opening this strategy for a wide range of diagnostic and prognostic indicators in human disease. In application, certain embodiments of the current invention have been used to identify stages in the progression of cancer, to identify host response in viral infection (HIV and KSHV), and to define cryptic effects of drugs of abuse (amphetamines, cocaine, and nicotine).

The current invention allows for the targeted analysis of specific areas of interest in complex genomes, provides a cost-effective strategy for querying multiple patient samples in a single reaction, provides a cost-effective manner of screening patient samples (conventional technology is more costly by at least two orders of magnitude), and opens a new field of biomarker development-nucleosome distribution, independent of genotype and gene expression.

Example

A full comprehension of the relationship between chromatin structure and genome function in cancer necessitates genome-wide chromatin structural measurements at multiple points in time throughout cancer progression. Although there have recently been a handful of extremely important studies measuring nucleosome distribution in a variety of organisms [Gaffney, D. J. et al. Controls of nucleosome positioning in the human genome. PLoS Genet 8, e1003036 (2012); Schones, D. E. et al. Dynamic regulation of nucleosome positioning in the human genome. Cell 132, 887-898 (2008); Valouev, A. et al. Determinants of nucleosome organization in primary human cells. Nature 474, 516-520 (2011); Druliner, B. R. et al. Chromatin patterns associated with lung adenocarcinoma progression. Cell Cycle 12, 1536-1543 (2013); Kent, N. A., et al. Chromatin particle spectrum analysis: a method for comparative chromatin structure analysis using paired-end mode next-generation DNA sequencing. Nucleic Acids Res 39, e26 (2011); Lee, W. et al. A high-resolution atlas of nucleosome occupancy in yeast. Nat Genet 39, 1235-1244 (2007); Yigit, E. et al. High-resolution nucleosome mapping of targeted regions using BAC-based enrichment. Nucleic Acids Res 41, e87 (2013); Sexton, B. S. et al. The spring-loaded genome: nucleosome redistributions are widespread, transient, and DNA-directed. Genome Res 24, 251-259 (2014); Dennis, J. H. et al. Independent and complementary methods for large-scale structural analysis of mammalian chromatin. Genome Res 17, 928-939 (2007)], there have been no genome-wide nucleosome distribution maps in primary patient tumors compared to their matched normal tissue. To meet this need, an approach named mTSS-seq was developed to comprehensively measure genome wide nucleosome distribution changes in the progression of cancer. In this study, the approach was validated for high resolution, genome-wide nucleosome distribution mapping utilizing data from a very high-quality human MNase-seq nucleosome mapping study and previous microarray based nucleosome maps from LAC patients. It is contemplated that this comprehensive analysis of the relationship between chromatin structure and genome regulation in the progression of cancer can be studied by persons of ordinary skill in the art and applied to other diseases and uses. Alternate applications include, but are not limited to, tracking damage by drugs of abuse, testing response to therapeutic drugs, monitoring cellular activity, and monitoring viral reactivation [Sexton, B. S. et al. The spring-loaded genome: nucleosome redistributions are widespread, transient, and DNA-directed. Genome Res 24, 251-259 (2014)].

In previous work by the current applicant, a model was introduced in which widespread changes in nucleosome distribution were identified as a feature specific to low grade cancer. That model was derived from the study of ~900 cell cycle- and immunity-related genes [Druliner, B. R. et al. Chromatin patterns associated with lung adenocarcinoma progression. Cell Cycle 12, 1536-1543 (2013)]. Because the original model was based on a limited set of genes, it was desired to determine whether the changes in nucleosome distribution were a widespread feature across all genes in the human genome. Therefore, the mTSS-seq target enrichment platform was developed to test and expand the original model across the entire human genome in multiple patient samples. Using mTSS-seq, changes in nucleosome distribution were measured between tumor and normal tissue, for each LAC patient, and three initial unexpected discoveries resulted: (1) nucleosome distribution changes are indeed a widespread feature across the entire genome in the tumor samples from early LAC patients, suggesting global dysregulation of chromatin remodeling as an early transformation event; (2) nucleosome distribution changes are consistent among the early LAC patients, suggesting a common dysregulation among patients; and (3) widespread nucleosome distribution changes are comparatively absent in more advanced tumors, suggesting that the remodeling dysregulation does not persist into advanced tumors. Widespread nucleosome distribution changes that appear in low-grade as opposed to more advanced tumors that are consistent between patients indicates an early, concerted genomic event in the progression of cancer. It can be hypothesized that if changes in nucleosome distribution act as an indicator of impending transcriptional regulation, then the nucleosome distribution measurements could act as predictive indicators of early transformation events. This explanation is manifested in a recent report from the current applicant in which widespread, transient, DNA-directed nucleosome redistributions were observed at immune loci upon reactivation of Kaposi's sarcoma-associated herpesvirus (KSHV), an oncogenic viral system [Sexton, B. S. et al. The spring-loaded genome: nucleosome redistributions are widespread, transient, and DNA-directed. Genome Res 24, 251-259 (2014)]. However, this idea would need to be further tested. What can be said and is shown herein is that nucleosome distributions, and changes thereof, are a marker associated with early cancer and detection of other possible noise of the system. A statistical approach to a determination of the noise of the system is described in [Id.], which is incorporated herein by reference, showing that a nucleosome difference of about 10% and above indicates the presence of noise. It was determined that this approximately 10% and higher threshold can confirm that the effects of the changes in nucleosome distribution are attributed to biological effects rather than technical noise. The statistical tool developed to assess differences in nucleosome distribution is a Wavelet ANOVA. This analysis was used to identify bona fide differences in nucleosome distribution and can be seen in supplementary FIG. 6 of [Id.]. Specifically, in addition to the analysis using correlation coefficient, a wavelet-based statistic was developed to determine differences between the 0-hour timepoint and all timepoints following KSHV reactivation. The statistic is capable of detecting changes of very small magnitudes and has been proven to be effective in comparing functional responses. The statistic demonstrates good power in detecting differences when compared to existing multivariate tests (for example, the Hotelling T2 test). The statistic was implemented as an ANOVA to determine changes simultaneously among multiple multivariate profiles with high power and a good control of the Type-I error. The statistic has a well-defined probability distribution, and p-values are obtained using Central Limit Theorem methods. Using this statistical analysis, the approximately 10% or higher threshold was determined.

In the current study, the original model [Druliner, B. R. et al. Chromatin patterns associated with lung adenocarcinoma progression. Cell Cycle 12, 1536-1543 (2013)] was additionally expanded by demonstrating that the nucleosome distribution changes occur through genetically-encoded regulatory signals: the nucleosomes in the grade one tumors are remodeled to positions encoded by the DNA sequence. Again, this observation is consistent with the work on KSHV, in which it was established that transient nucleosome redistributions, rather than basal architectures, adopt locations favored by the underlying DNA sequence [Sexton, B. S. et al. The spring-loaded genome: nucleosome redistributions are widespread, transient, and DNA-directed. Genome Res 24, 251-259 (2014)]. In the current study, it was demonstrated that the low-grade tumor samples had a higher correlation with the predicted model as compared to normal tissue at over 85% of remodeled genes, indicating that nucleosome distribution alterations are driven by the underlying DNA sequence [Fincher, J. A. & Dennis, J. H. in Epigenetics: a reference manual (ed Craig J, W. N.) 133-142 (Horizon Scientific Press, Norwich, U K, 2011); Gupta, S. et al. Predicting human nucleosome occupancy from primary sequence. PLoS Comput Biol 4, e1000134 (2008); Sexton, B. S. et al. The spring-loaded genome: nucleosome redistributions are widespread, transient, and DNA-directed. Genome Res 24, 251-259 (2014)]. An interpretation that reflects these consistent grade-one nucleosome distribution alterations is that the redistributions result from the misregulation of a chromatin remodeling complex that culminates in nucleosomal redistribution to DNA-directed positions. This is conceivable given the evidence in the literature on genomic dysregulation through mutation of chromatin remodeling complexes in cancer determined by exome sequencing [Neely, K. E. & Workman, J. L. The complexity of chromatin remodeling and its links to cancer. Biochim Biophys Acta 1603, 19-29 (2002); Reisman, D. N., Sciarotta, J., Wang, W., Funkhouser, W. K. & Weissman, B. E. Loss of BRG1/BRM in human lung cancer cell lines and primary lung cancers: correlation with poor prognosis. Cancer Res 63, 560-566 (2003); Varela, I. et al. Exome sequencing identifies frequent mutation of the SWI/SNF complex gene PBRM1 in renal carcinoma. Nature 469, 539-542 (2011); Weintraub, H. & Groudine, M. Chromosomal subunits in active genes have an altered conformation. Science 193, 848-856 (1976); Zang, Z. J. et al. Exome sequencing of gastric adenocarcinoma identifies recurrent somatic mutations in cell adhesion and chromatin remodeling genes. Nat Genet 44, 570-574 (2012)].

A remaining question centers on the apparently ephemeral nature of these grade-one changes, and the degree to which redundant and overlapping chromatin regulatory activities play a role in the complex progression of cancer.

To answer questions regarding the effects of these apparently transient nucleosome redistributions, evidence was provided that nucleosome redistributions likely potentiate transcription factor binding events. Using subnuclesomal sized DNA fragments as an indicator of transcription factor binding, depletion or enrichment of transcription factor sized protections were measured at known transcription factor binding sites identified by ChIP in A549 lung cancer cells. An increase in the presence of subnucleosomal fragments was observed in high grade tumors compared to normal tissue at known transcription factor binding sites identified by ChIP in A549 lung cancer cells, indicating the presence of a sequence-specific DNA-binding protein [A user's guide to the encyclopedia of DNA elements (ENCODE). PLoS Biol 9, e1001046 (2011)]. This increase in transcription factor binding in advanced tumors relative to the normal tissue and grade one tumors suggests that nucleosome redistributions early in the progression of cancer potentiated the licensing of these regulatory factors.

An additional extension of the original study [Druliner, B. R. et al. Chromatin patterns associated with lung adenocarcinoma progression. Cell Cycle 12, 1536-1543 (2013)] is the finding of widespread nucleosome redistributions in the progression of CRC that are concordant with the changes observed in LAC. In LAC, nucleosome distribution alterations are widespread in low grade tumors (grade one, stage one), and these alterations are not seen in high grade tumors (grade three, stage two). These widespread nucleosome distribution alterations were shown to also occur in early CRC (stage two and three), and these changes are relatively absent in more advanced CRC (stage four). There is a high overlap of genes with nucleosome distribution alterations between LAC and CRC. Moreover, it was shown that the redistributions in CRC have a strong agreement with genetically encoded nucleosome distribution signals, indicating that the nucleosome distribution changes are DNA-directed as in LAC. The discovery of increased transcription factor binding events in advanced tumors was also observed in CRC patients. Utilizing a high-resolution, genome-wide technology to identify widespread chromatin structural changes in early tumors across multiple cancer types while defining the functional regulation through analysis of cis- and trans-acting factors validates the power of this approach to study chromatin structure in the progression of multiple cancers and disease states.

Figure 8A:
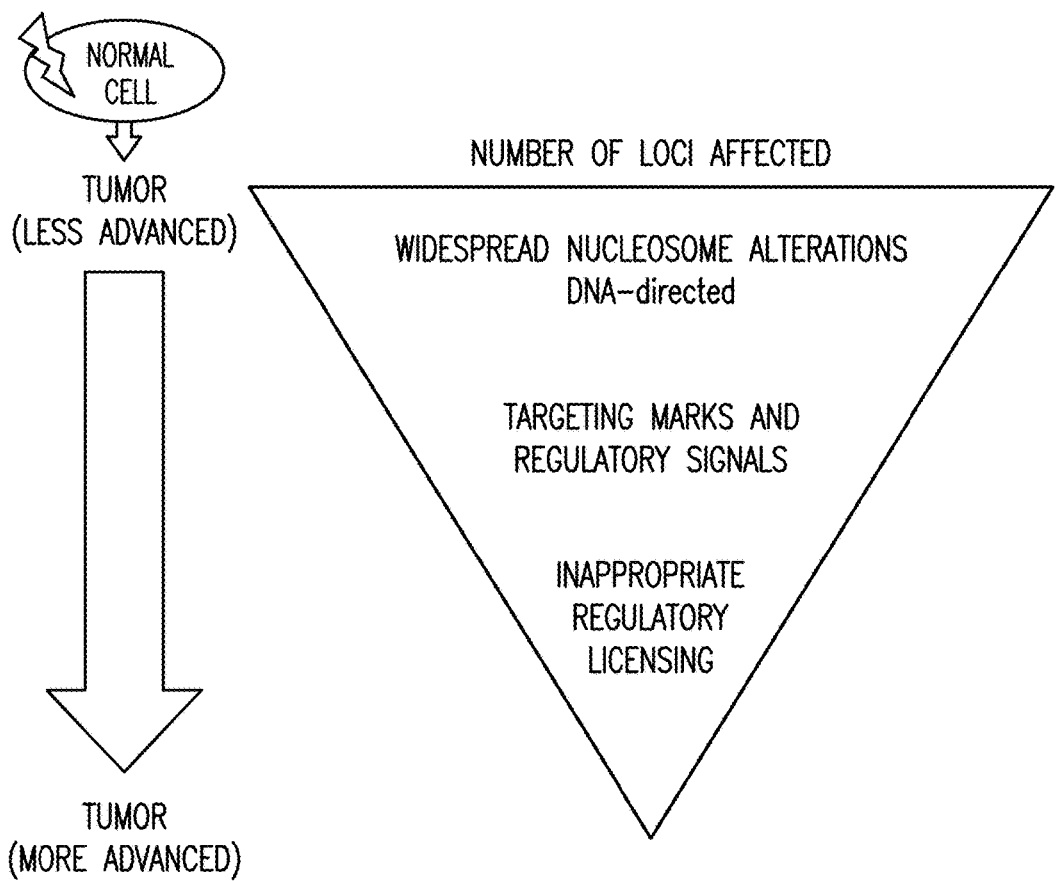
FIGS. 8A-8B depict a model for chromatin based hierarchical genome regulation.
Figure 8B:
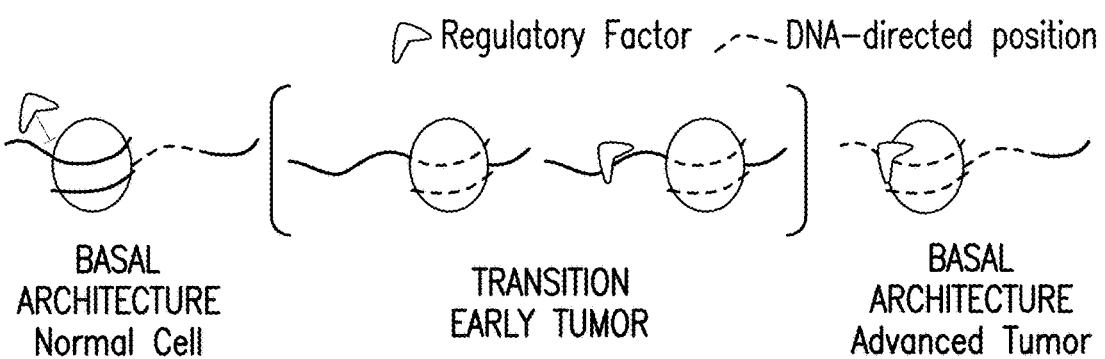

Taken together these results clarify structure-function relationships in the human genome, and support a hierarchical mechanism for chromatin mediated genomic regulation, such that an approximately 10% or greater difference in nucleosome distribution indicates presence of noise of the system [Sexton, B. S. et al. The spring-loaded genome: nucleosome redistributions are widespread, transient, and DNA-directed. Genome Res 24, 251-259 (2014)]. This study demonstrates that widespread, DNA-directed nucleosome redistributions are limited to early tumors in LAC and CRC, though applicable to other carcinogens and diseases. This hierarchical model describes the interpretation that these nucleosome redistributions likely allow for inappropriate regulatory licensing in cancer (FIG. 8A). Indeed, inappropriate genomic licensing is frequently cited as a characteristic of transformed phenotype [Feinberg, A. P. Epigenetic stochasticity, nuclear structure and cancer: the implications for medicine. J Intern Med (2014); Timp, W. & Feinberg, A. P. Cancer as a dysregulated epigenome allowing cellular growth advantage at the expense of the host. Nat Rev Cancer 13, 497-510 (2013)]. It can be interpreted that in the later stage and grade tumors when nucleosomes return to their basal positions, the regulatory machinery is altered, and contributes to the progression of the disease (FIG. 8B). This comprehensive and integrated analysis of the relationship between chromatin structure and the progression of cancer has allowed one to define nucleosome alterations as generally exploited sites of concerted dysregulation in cancer.

Materials and Methods

Patient Samples and Tissue Processing

Primary samples from surgically removed tumors of lung adenocarcinoma patients, and corresponding normal tissue were obtained from the University of Massachusetts Medical School (UMMS) Tissue Bank, and prepared as previously described [Druliner, B. R. et al. Chromatin patterns associated with lung adenocarcinoma progression. Cell Cycle 12, 1536-1543 (2013)]. Corresponding tissue samples can be described generally as contralateral identical or substantially similar tissue. For example, if there is a tumor in the left lunch, then a similar or identical tissue sample from the symmetrical location on the unaffected right lung would be taken. Primary samples from colorectal adenocarcinoma patients with a surgically removed tumor, and corresponding normal tissue, were obtained from the Mayo Clinic. A total of seven (7) tumor specimens were included in this study (LAC: two grade one, two grade three; CRC: one of each stage one, two and three), with matched normal tissue for each tumor specimen, for a total of 14 genomes that were sequenced. The tumor and normal material was snap-frozen in liquid nitrogen within 1 h after surgery. Samples were examined by board-certified pathologists, using hematoxylin and eosin staining. Samples were selected by grade and stage, and only samples with 80% or more tumor cells were included, as assessed by histological examination. Patient samples were anonymized, and patient history was received along with the samples. Harvesting of nuclei, MNase digestion and mononucleosomal isolation were performed on each sample as previously described [Id.]. Table 1 lists preparation information on each patient sample.

TABLE 1

Patient samples, MNase preparation and sequencing processing. Lung and colon adenocarcinoma patients, matched normal and tumor, from whom the samples used in the sequencing study were taken.

| Sample ID | MNase Preparation | Sequencing Processing |
| --- | --- | --- |
| LAC 4137, N and T | identical MNase prep samples from Druliner et. al., 2013; new digestion from remaining nuclei | original prep on HiSeq2000 (1 lane, multiplexed) and MiSeq, new prep on HiSeq2000 (1 lane, multiplexed); all reads combined for analyses |
| LAC 1357, N and T | identical MNase prep samples from Druliner et. al., 2013 | sequenced on MiSeq (4 lanes, multiplexed) |
| LAC 873, N and T | new MNase digestion from remaining nuclei (original nuclei isolation from Druliner et. al., 2013) | sequenced on HiSeq (1 lane, multiplexed) |
| LAC 386, N and T | new MNase digestion from remaining nuclei (original nuclei isolation from Druliner et. al., 2013) | sequenced. on HiSeq (1 lane, multiplexed) |
| CRC 512, N and T | tissue obtained 2013, nuclei isolated. cross-linked, MNase digested as described in Druliner, et, al., 2013 (patients previously unpublished) | sequenced on HiSeq (1 lane, multiplexed) |
| CRC 524, N and T | tissue obtained 2013, nuclei isolated, cross-linked, MNase digested as described in Druliner, et. al., 2013 | sequenced on HiSeq (1 lane, multiplexed) |
| CRC 533, N and T | tissue obtained 2013, nuclei isolated, cross-linked, MNase digested as described in Druliner, et. al., 2013 | sequenced on HiSeq (1 lane, multiplexed) |

Mononucleosome DNA Library Preparation

MNase digested DNA sequencing libraries were prepared using the NEBNEXT® ULTRA™ DNA Library Prep Kit for ILLUMINA® (NEB #E7370S/L), starting with thirty nanograms of input mononucleosomal DNA. Following end prep and adaptor ligation, libraries were cleaned-up with AMPURE® XP Beads (Beckman Coulter, Inc. #A63881) without size selection due to the original input of a size population of ~150 bp. Universal and indexed sequences were added through 8 cycles of PCR, using NEBNEXT® Multiplex Oligos for ILLUMINA® (Index Primers Set 1, NEB #E7335S/L). The NEBNEXT® Multiplex Oligos kit contains indices 1-12 which correspond to the identical product if using ILLUMINA® TruSeq primers. The libraries were quantity and quality checked using the QUBIT Fluorometer High Sensitivity Kit and Agilent High Sensitivity DNA kit on the AGILENT 2100 Bioanalyzer. The average size of material across all libraries was 275 bp, and the average total material in this region was more than 90%; there were no adapter or primer dimers.

Solution-Based Sequence Capture, Enabling TSS-Enrichment

A custom designed ROCHE NIMBLEGEN SeqCap EZ Library SR was used to capture ~2 kb regions flanking the TSS for every gene in the human genome, using the HG19 build. The number of base pairs was chosen because it was found herein that gene regulation occurs within approximately 1,000 base pairs of the TSS. As such, the 2,000 base pairs surrounding the TSS (1,000 base pairs upstream and 1,000 base pairs downstream from the TSS) provided for the accurate identification of gene regulatory elements. In addition, TSS for the human genome are well-documented, facilitating identification of the TSS and the 2 kb immediately surrounding the TSS. The TSS sequences were repeat masked, so only unique probes were included. The sequence capture was performed according to the manufacturer's protocol. Following a 72 hour capture hybridization, a 15 cycle PCR amplification was performed using the TRUSEQ primer 1 (SEQ ID NO:1) and TRUSEQ primer 2 (SEQ ID NO:2). A quantitative real-time PCR was then performed to confirm that regions within the sequence capture were successfully enriched, and that regions excluded from the capture were depleted post-capture. Three regions were selected within the 2 kb TSS of genes, where the regions were known to be in the SeqCap design (on-target), and the same three genes regions outside of the 2 kb TSS were selected, where the regions were known not to be in the SeqCap design (off-target). The on-target and off-target regions and primer sequences can be found in Table 2. For example, the primers SEQ ID NO:3 and SEQ ID NO:4 were used to amplify on-target regions within the 2 kb surrounding the TSS of genes, allowing quantitative measurement of the regions. Dilutions were made in elution buffer to 10 nM stock in 0.05% TWEEN®-20.

TABLE 2

Primers for enrichment qPCR. Primer design for performing qPCR to determine enrichment of on-target and depletion of off-target regions.

| Gene Name | Genome Region | On-target/Off-target | Primer Name (forward) | Primer Sequence (forward) | Primer Name (reverse) | Primer Sequence (reverse) |
| --- | --- | --- | --- | --- | --- | --- |
| ATM | chr11: 10893855-10894255 | On-target | ATM_ONTARGET_F | SEQ ID NO: 3 | ATM_ONTARGET_R | SEQ ID NO: 4 |
| ATM | chr11: 108098504-108098615 | Off-target | ATM_OFFTARGET_F | SEQ ID NO: 5 | ATM_OFFTARGET_R | SEQ ID NO: 6 |
| RHOC | chr1: 113250099-113250499 | On-target | RHOC_ONTARGET_F | SEQ ID NO: 7 | RHOC_ONTARGET_R | SEQ ID NO: 8 |
| RHOC | ch1r: 113246266-113246422 | Off-target | RHOC_OFFTARGET_F | SEQ ID NO: 9 | RHOC_OFFTARGET_R | SEQ ID NO: 10 |
| ITA4 | chr2: 182321015-182321415 | On-target | ITGA4_ONTARGET_F | SEQ ID NO: 11 | ITGA4_ONTARGET_R | SEQ ID NO: 12 |
| ITGA4 | chr2: 182322923-182323044 | Off-target | ITGA4_OFFTARGET_F | SEQ ID NO: 13 | ITGA4_OFFTARGET_R | SEQ ID NO: 14 |

Illumina Flowcell Hybridization and Sequencing

The multiplexed samples were loaded at 12 pM on two lanes of an ILLUMINA HiSeq 2500 system, HiSeq Flow Cell v3. For the HiSeq, the suggested range is 10-20 pM. Kits used were the TRUSEQ PE Cluster Kit v3-cBot-HS and the TRUSEQ SBS Kit v3.

There are two measures for data quality: (1) clusters that pass filter (PF), and (2) quality score, which is given as a percentage of reads >Q30. The reads are based on the reads that pass the chastity filter not the Q30 filter. In addition, each lane was spiked with 1% PhiX as the control. The software performs real-time reporting of error rates for the PhiX spike-in lanes. The sequencing was a paired-end 50 bp run on the HiSeq, using HiSeq Control Software (HCS) version 2.0. The LAC lane had cluster density of 695K/mm[2], a PF of 94%, and 96.6% of the reads having a quality score >Q30. The CRC lane had cluster density of 736K/mm[2], a PF of 94%, and 96.1% of the reads having a quality score >Q30. The samples that were sequenced by on the MiSeq were run on 3 lanes, and was paired-end 150 bp sequenced (Table 1—sequencing processing). The first lane was loaded at 8 pM and generated 1468 clusters k/mm2. The other two lanes were loaded at 4 pM and obtained 681 k/mm2 and 658 k/mm2 clusters, respectively. MiSeq V2 reagents were used and the MiSeq default settings were applied to generate fastq files that contain only PF reads (pass filter). The reads were demultiplexed on the MiSeq using the default settings.

Alignment and Data Processing Bioinformatics

CASAVA software was used to demultiplex the indices in each lane. ILLUMINA adapters were clipped from reads with cutadapt [Martin, M. Cutadapt removes adapter sequences from high-throughput sequencing reads. EMBnet.journal [Online] 17.1, 10-12 (2011)] and aligned to the hg19 human genome assembly with bowtie2 2.1.0 with default parameters [Langmead, B. & Salzberg, S. L. Fast gapped-read alignment with Bowtie 2. Nat Methods 9, 357-359 (2012)]. Unpaired and non-uniquely-mapped reads were discarded with samtools [Li, H. et al. The Sequence Alignment/Map format and SAMtools. Bioinformatics 25, 2078-2079 (2009)]. Individual nucleosome footprints were extracted from BAM files with bedtools 2.17 [Quinlan, A. R. & Hall, I. M. BEDTools: a flexible suite of utilities for comparing genomic features. Bioinformatics 26, 841-842 (2010)]. Nucleosome occupancy profiles were obtained by calculating the fragments per million that mapped at each base-pair in the probed regions with bedtools.

Nucleosome dyad frequencies (midpoints) were obtained by calculating the sum of nucleosome dyads (fragment centers) in 100-bp windows at a 10-bp step-size with bedtools. Data were subsequently processed in R 2.15.1 55. Data was uploaded to the UCSC Genome Browser for further analysis [Kent, W. J. et al. The human genome browser at UCSC. Genome Res 12, 996-1006 (2002); Kent, W. J., Zweig, A. S., Barber, G., Hinrichs, A. S. & Karolchik, D. BigWig and BigBed: enabling browsing of large distributed datasets. Bioinformatics 26, 2204-2207 (2010)].

Results

Development of a Solution-Based TSS-Enrichment Sequence Capture Method for Mononucleosome DNA from Primary Patient Tissue In this study, genome-wide chromatin structure was measured in primary patient tumors. At the outset, matched tumor and normal tissue were used from grade one and three LAC patients, on which the current applicant previously reported [Druliner, B. R. et al. Chromatin patterns associated with lung adenocarcinoma progression. Cell Cycle 12, 1536-1543 (2013)]. The workflow is shown in FIG. 1A, where, following digestion with MNase, mononucleosomal DNA was isolated (all material below ~150 bp was excised from a 2% agarose gel). In many cases, the exact mononucleosomally protected DNA sample prepared for the original report on these patients was used (Table 1—MNase preparation column). This MNase digested, mononucleosome DNA material was used to prepare multiplexed libraries. Notably, selection of material from the nucleosomal ladder that was ~150 bp and lower allowed for analyses of subnucleosomal fragments derived from other non-histone DNA-binding proteins, such as transcription factors. The addition of adaptor and barcode ligated material was efficiently tracked at every step of the library preparation and accurately quantified the exact number of molecules (adjusted for size) to be sequenced. This ensured that the majority of the reads obtained would strictly provide nucleosome and subnucleosome information.

Figure 1B:
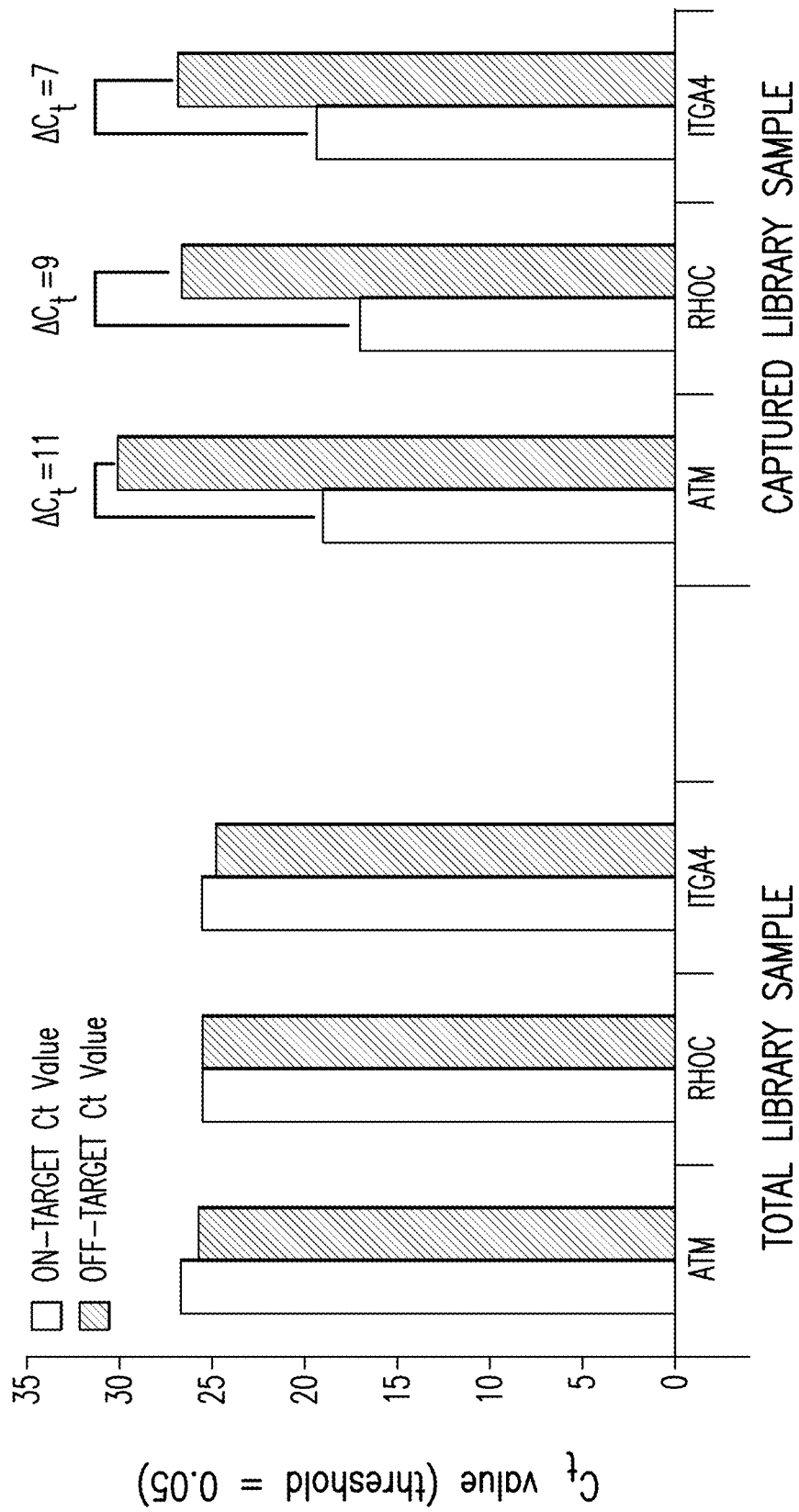
Figure 1C:
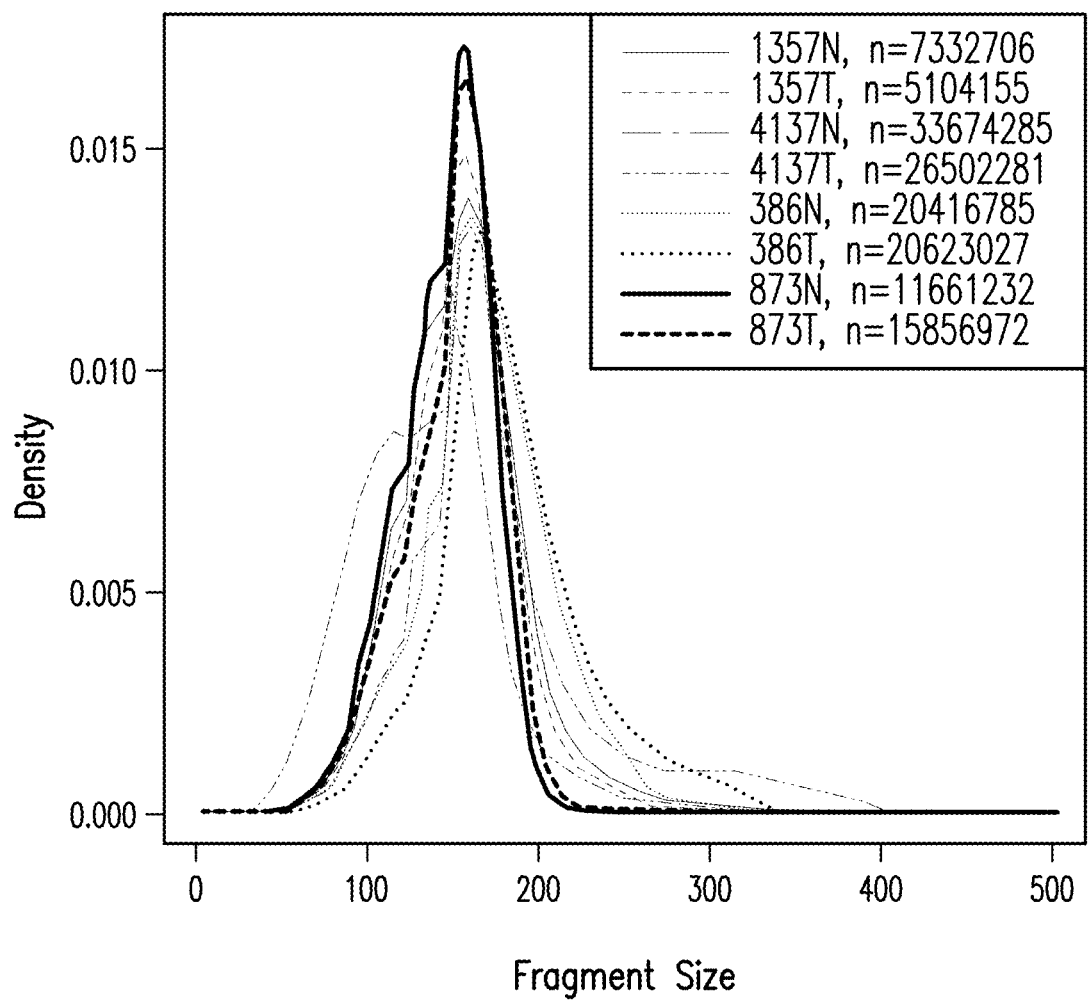
Figure 1D:
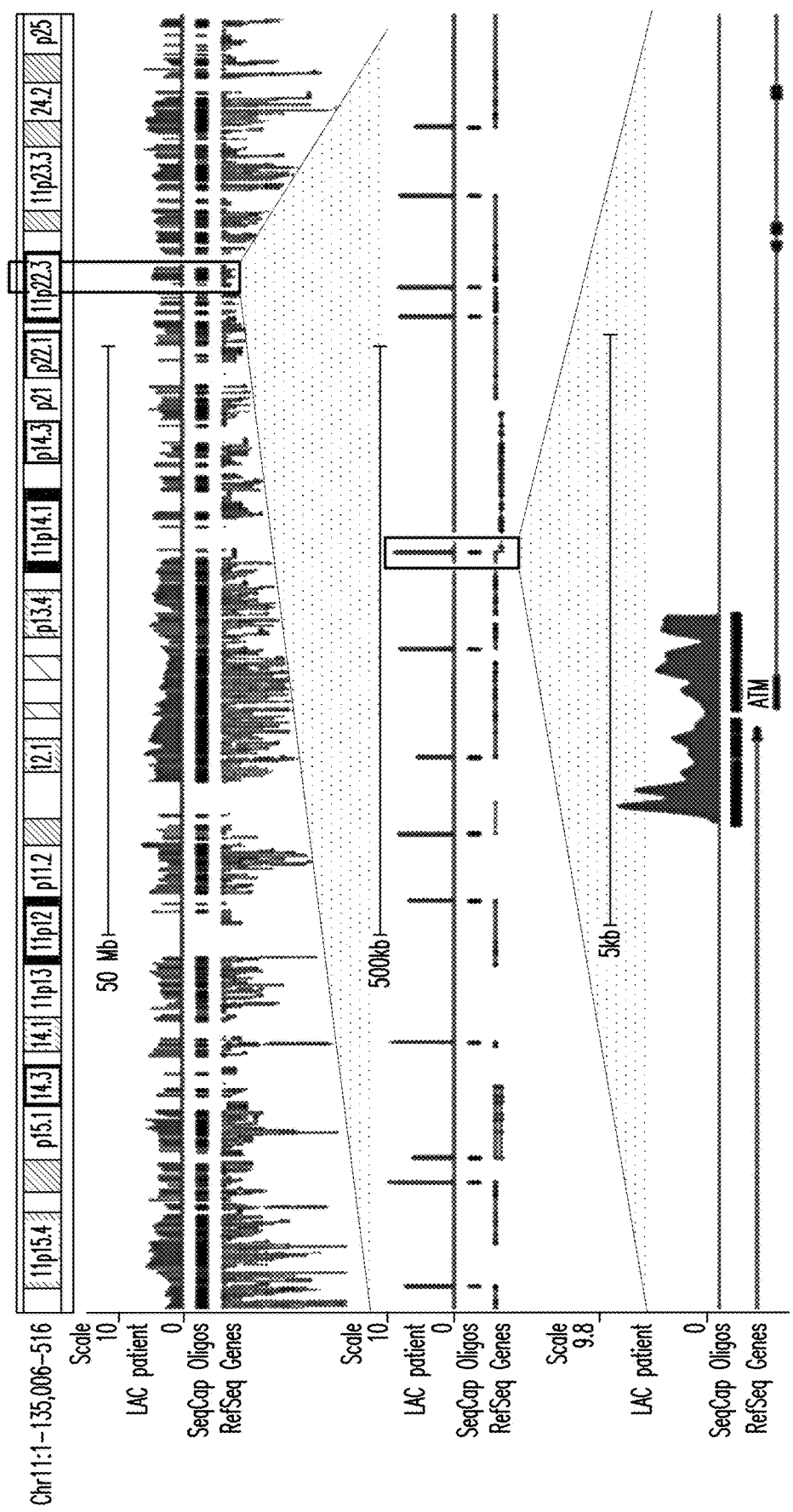

Following preparation of the libraries, the solution-based sequence capture was used to select the 2000 bp surrounding the TSS of all human open reading frames, allowing capture of nucleosomes covering ~48 Mb of the human genome. Prior to performing paired-end sequencing on the captured material, the enrichment of the sequence capture was quantified by qPCR using specific primers to regions on-target and off-target from the capture (FIG. 1B). In the captured libraries, the difference between the on-target (enriched) and off-target (depleted) CT values differed at an average of 9 cycles (minimum of 100-fold enrichment). Following sequencing, the paired-end reads were aligned to the human genome, and the size of each fragment was determined from the separation of the paired ends (FIG. 1C). The majority of the sequenced fragments were within the ~75-200 bp size range, showing that the range of sizes across samples was relatively consistent. FIG. 1D shows the frequency of inferred nucleosome midpoints in genome traces across chromosome 11, and zoomed in twice at 100× to eventually show a single locus (TSS of the ATM gene) and the resulting nucleosome distribution map (FIG. 1D). The sequence capture oligos used to capture the 2 kb surrounding the TSS are shown in this view, along with the data corresponding to the targeted regions, which in every case made up over 90% of the total sequencing reads (see Table 3).

TABLE 3

| Sample | Raw | Aligned to genome | On-Target (reads aligned to seqcap oligos) | Off-Target (reads aligned to seqcap oligos) | % On-Target | % Off-Target |
|---|---|---|---|---|---|---|
| 4137N | 46,300,390 | 37,216,362 | 33,674,285 | 3,542,077 | 0.90 | 0.10 |
| 4137I | 38,324,430 | 29,778,407 | 26,702,281 | 3,126,126 | 0.90 | 0.10 |
| 1357N | 9,026,754 | 8,101,614 | 7,332,706 | 768,908 | 0.91 | 0.09 |
| 1357T | 6,790,830 | 5,653,261 | 5,104,155 | 549,106 | 0.90 | 0.10 |
| 873N | 14,454,359 | 12,675,104 | 11,661,232 | 1,013,872 | 0.92 | 0.08 |
| 8731 | 19,465,767 | 17,205,831 | 15,856,972 | 1,348,859 | 0.97 | 0.08 |
| 386N | 24,910,145 | 22,121,267 | 20,416,785 | 1,704,482 | 0.92 | 0.08 |
| 386T | 25,054,967 | 22,300,403 | 20,623,027 | 1,677,376 | 0.92 | 0.08 |

Figure 2A:
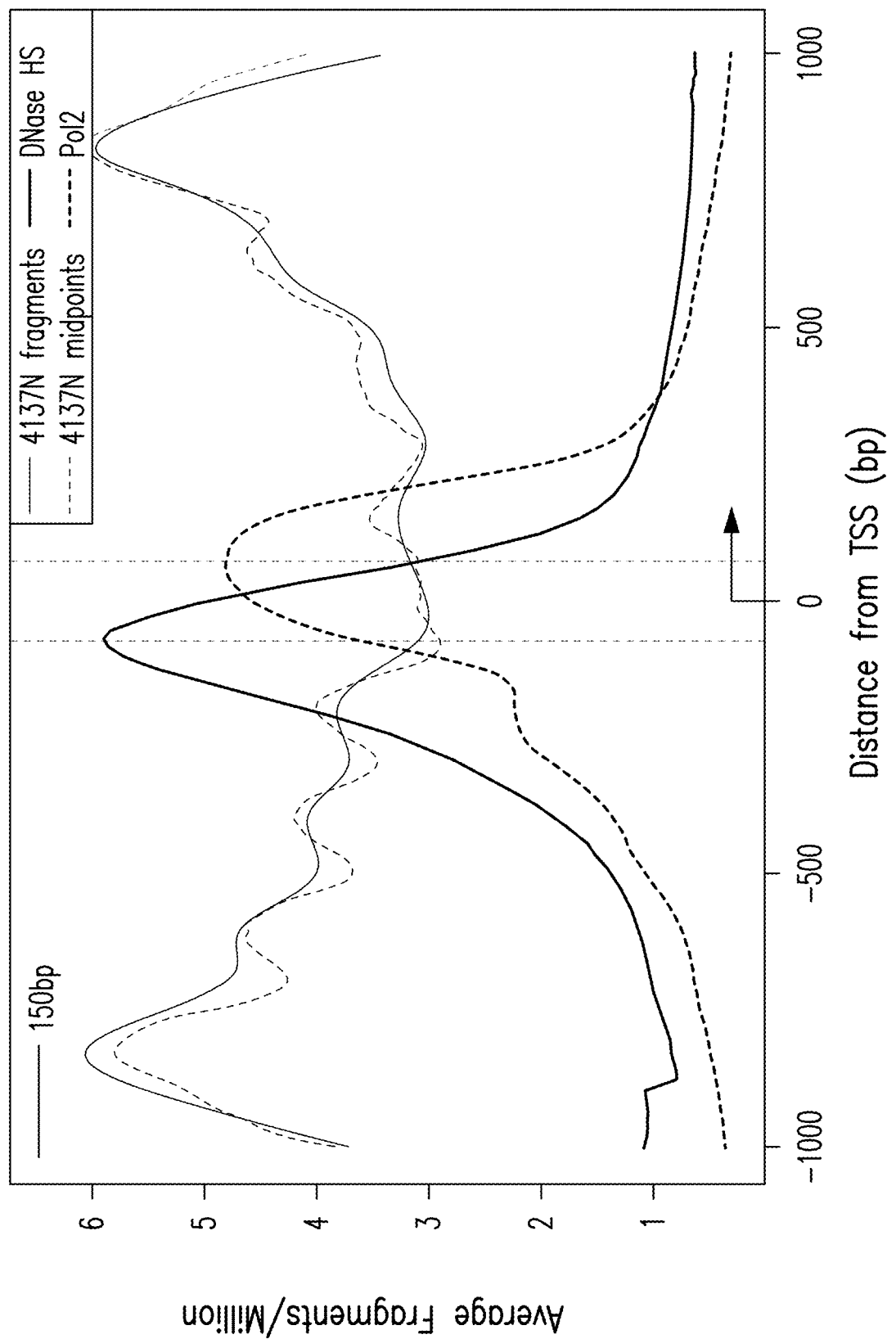
FIGS. 2A-2D are graphical illustrations showing that nucleosome mapping by mTSS-seq identifies bona fide nucleosome characteristics, and is concordant with other human nucleosome mapping studies.

Paired-End Reads Generated by mTSS-Seq Yield Typical Nucleosome Characteristics, and are Concordant with Previous Reports in the Literature To validate the use of mTSS-seq to accurately map nucleosome distribution, typical nucleosome characteristics were identified in the current data, and the current data was compared to other published human nucleosome mapping studies. To determine whether the current data contained typical nucleosome properties, the average nucleosome distribution for all TSSs in the genome was plotted, and the dinucleotide frequencies were determined. Nucleosome organization averaged around the TSS of human genes shows a canonical structure with phased nucleosomes centered on a nucleosome depleted region [Valouev, A. et al. Determinants of nucleosome organization in primary human cells. Nature 474, 516-520 (2011)]. The average nucleosome organization at the TSS was determined for the data by aligning all TSSs and plotting the corresponding sequence fragment midpoints for the 2 kb surrounding the TSS (FIG. 2A). The mTSS-seq data recapitulate the pattern of other studies that plotted average nucleosome occupancy at the TSS in humans, where there is a NDR (nucleosome-depleted region) surrounding and immediately downstream of the TSS, with well-positioned nucleosomes flanking the NDR [Id.]. Additionally, it was demonstrated that the NDR directly upstream of the TSS overlaps with a peak in genomic DNase I hypersensitivity, and a ChIP peak for RNA polymerase II is seen just downstream of the TSS within the gene body, as anticipated [Id.: Boyle, A. P. et al. High-resolution mapping and characterization of open chromatin across the genome. Cell 132, 311-322 (2008); Fenouil, R. et al. CpG islands and GC content dictate nucleosome depletion in a transcription-independent manner at mammalian promoters. Genome Res 22, 2399-2408 (2012); Kundaje, A. et al. Ubiquitous heterogeneity and asymmetry of the chromatin environment at regulatory elements. Genome Res 22, 1735-1747 (2012); Zhang, Y., Shin, H., Song, J. S., Lei, Y. & Liu, X. S. Identifying positioned nucleosomes with epigenetic marks in human from ChIP-Seq. BMC Genomics 9, 537 (2008)]. The current technology was further validated with a sequence analysis of the nucleosome-sized fragments generated by mTSS-seq.

Figure 2B:
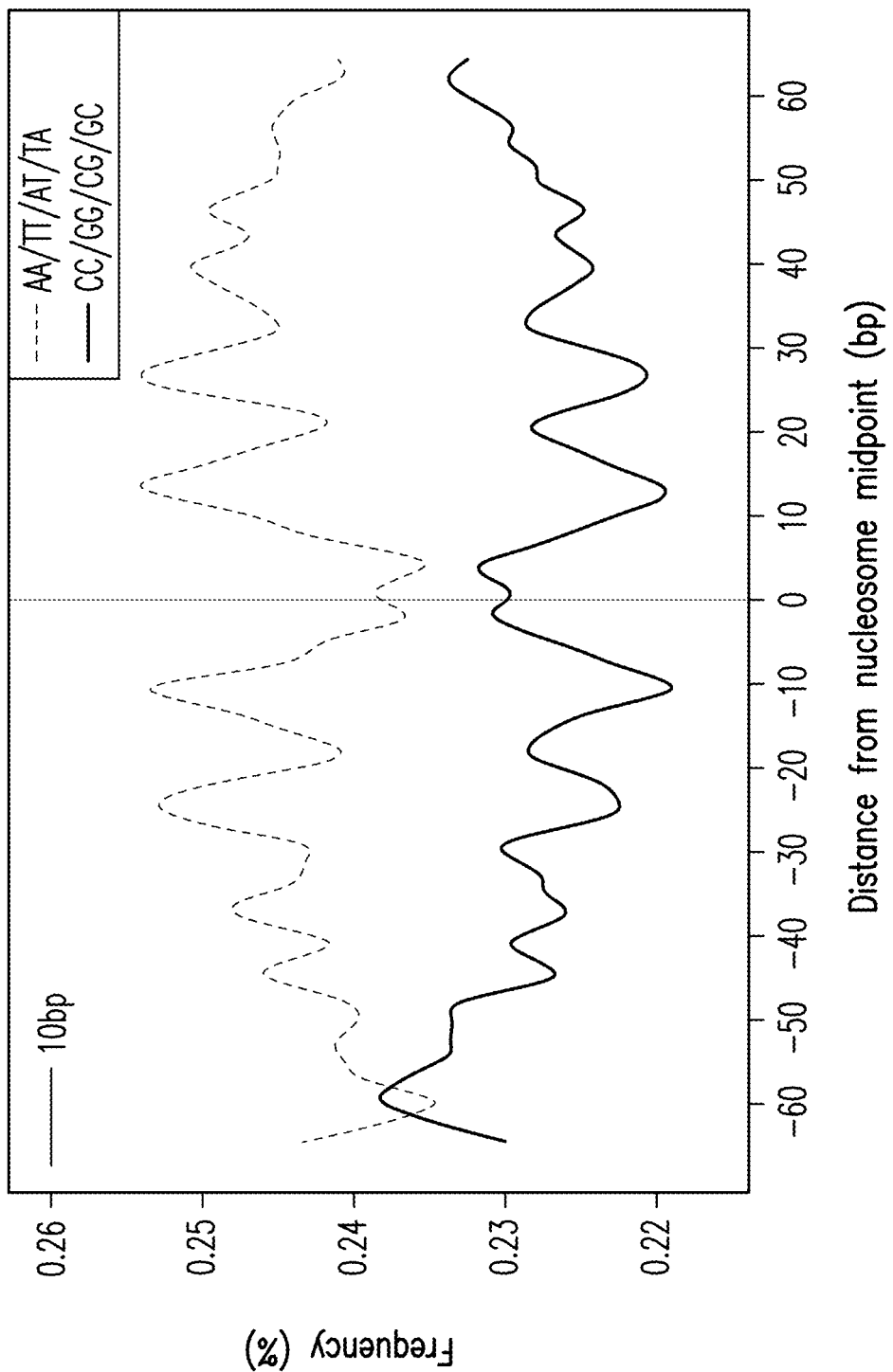

A major determinant of the ability of DNA to conform to the histone octamer into a nucleosome is the specific patterns of dinucleotides [Fincher, J. A. & Dennis, J. H. in Epigenetics: a reference manual (ed Craig J, W. N.) 133-142 (Horizon Scientific Press, Norwich, U K, 2011)]. Specifically, periodic AA distributions occur in sequences higher than expected, and are thought to be responsible for genome organization into nucleosomes [Bolshoy, A., McNamara, P., Harrington, R. E. & Trifonov, E. N. Curved DNA without A-A: experimental estimation of all 16 DNA wedge angles. Proc Natl Acad Sci USA 88, 2312-2316 (1991); Schellman, J. A. Flexibility of DNA. Biopolymers 13, 217-226 (1974); Trifonov, E. N. & Sussman, J. L. The pitch of chromatin DNA is reflected in its nucleotide sequence. Proc Natl Acad Sci USA 77, 3816-3820 (1980); Zhurkin, V. B., Lysov, Y. P. & Ivanov, V. I. Anisotropic flexibility of DNA and the nucleosomal structure. Nucleic Acids Res 6, 1081-1096 (1979)]. The periodic occurrence of A/T containing dinucleotides at ~10 bp intervals was calculated from first principles and verified in several subsequent studies [Drew, H. R. & Travers, A. A. DNA bending and its relation to nucleosome positioning. J Mol Biol 186, 773-790 (1985); Drew, H. R. & Travers, A. A. Structural junctions in DNA: the influence of flanking sequence on nuclease digestion specificities. Nucleic Acids Res 13, 4445-4467 (1985); Kaplan, N. et al. The DNA-encoded nucleosome organization of a eukaryotic genome. Nature 458, 362-366 (2009); Segal, E. et al. A genomic code for nucleosome positioning. Nature 442, 772-778 (2006)]. When the dinucleotide frequency of 150 bp fragments was examined, it was found the acknowledged 10 bp periodicity for A/T containing dinucleotides, comparable to the frequency patterns identified in other human studies (FIG. 2B) [Gaffney, D. J. et al. Controls of nucleosome positioning in the human genome. PLoS Genet 8, e1003036 (2012); Segal, E. et al. A genomic code for nucleosome positioning. Nature 442, 772-778 (2006); Yigit, E. et al. High-resolution nucleosome mapping of targeted regions using BAC-based enrichment. Nucleic Acids Res 41, e87 (2013)]. These results affirm that the high resolution maps provided by mTSS-seq are consistent with the major qualitative features of nucleosome distribution at the TSS, and with the sequence composition of bona fide nucleosomal particles.

Figure 2C:
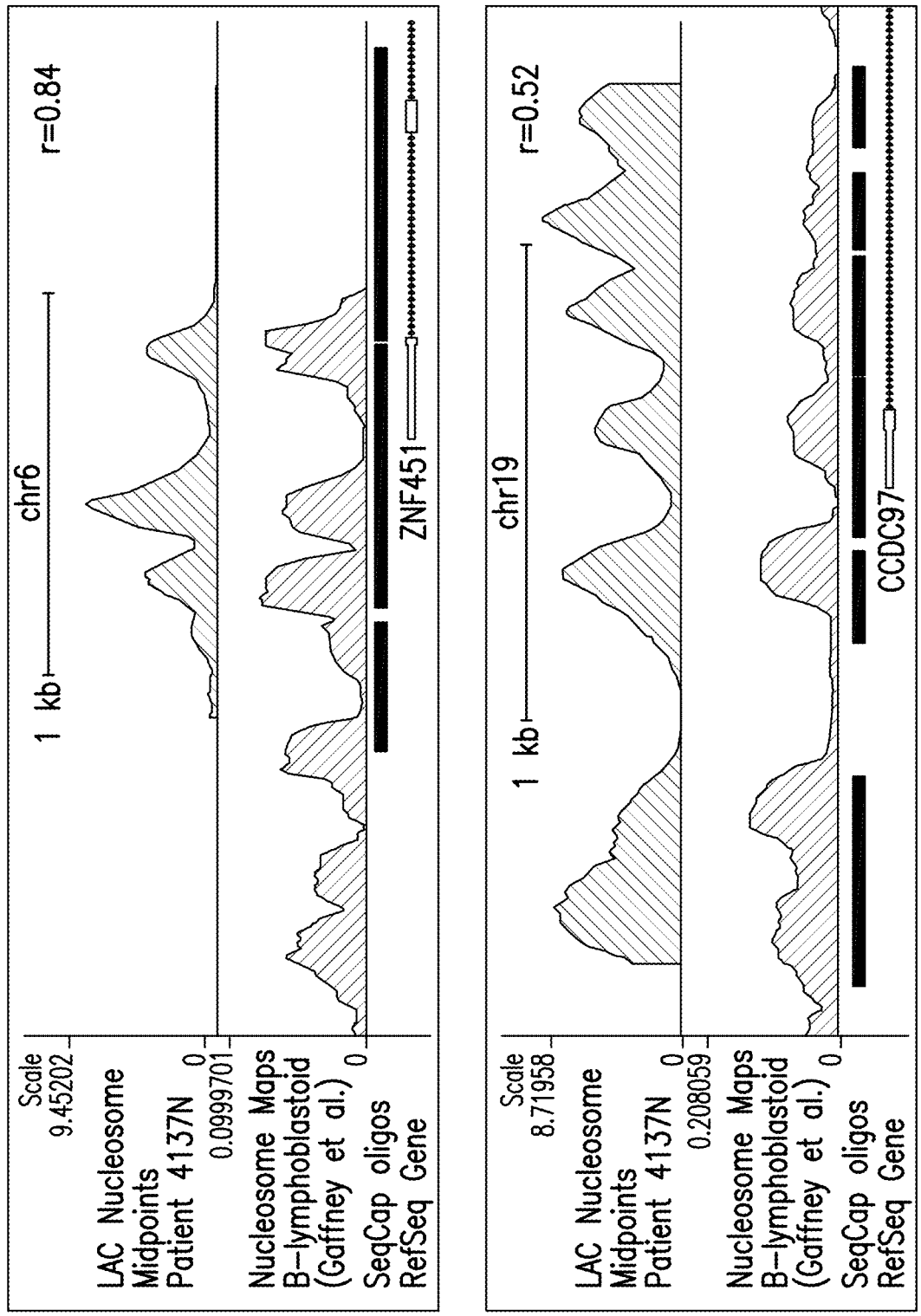
Figure 2D:
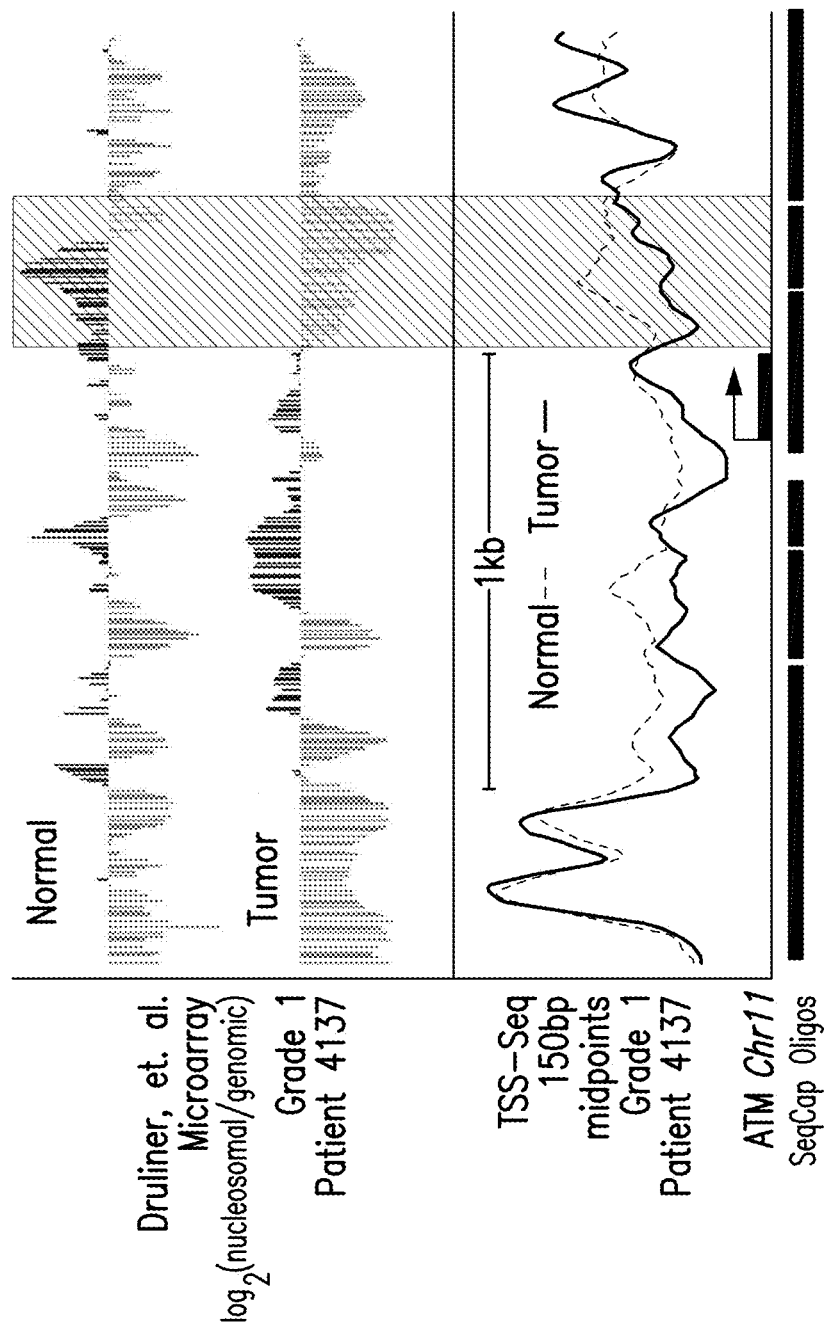
Figure 3A:
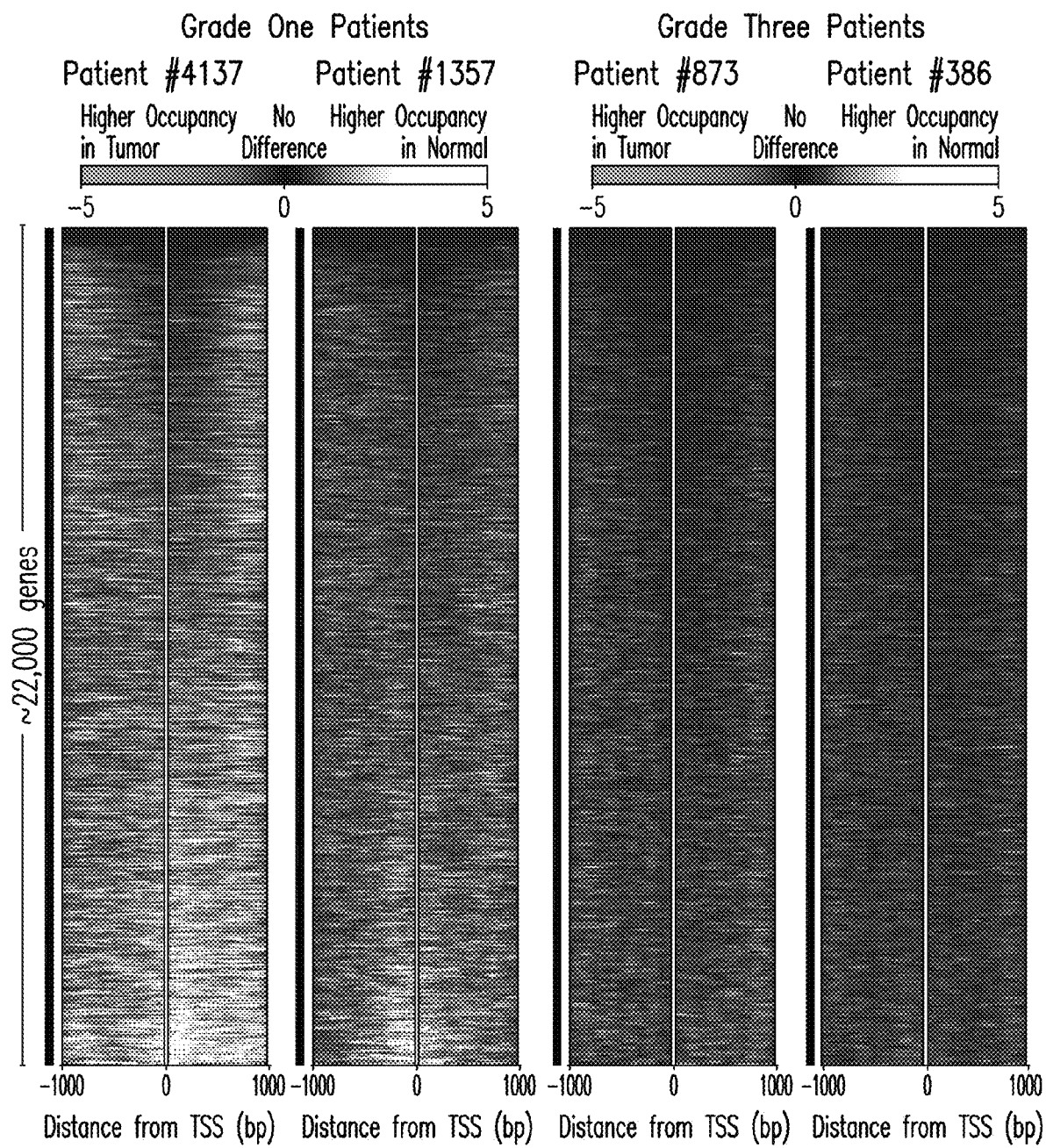

A subsequent step in the study was to verify that the current mTSS-seq data agreed with precedent human nucleosome mapping studies at specific loci. This comparison can be particularly important, as averages and qualitative measures of general nucleosome distributions are not necessarily sufficient to make claims about nucleosome organizations at specific loci. The nucleosome distribution data of normal lung epithelial patient tissue from the current study (patient #4137N) was compared to data from a human lymphoblastoid cell line [Gaffney, D. J. et al. Controls of nucleosome positioning in the human genome. PLoS Genet 8, e1003036 (2012)]. A positive global correlation of 0.37 was found. Two representative examples are shown at the loci ZNF451 (r=0.84) and CCDC197 (r=0.52), demonstrating the similarity between the current mTSS-seq derived data and the lymphoblastoid cell line data (FIG. 2C). The mTSS-seq data was next validated by comparison to the current applicant's previously published microarray-based study [Druliner, B. R. et al. Chromatin patterns associated with lung adenocarcinoma progression. Cell Cycle 12, 1536-1543 (2013)]. Changes were detected in nucleosome distribution between normal and tumor tissue in the early LAC patients; these changes are consistent with those observed by microarray (FIG. 2D). The comprehensive mTSS-seq approach, therefore, allows the generation of nucleosome distribution maps and measurement of changes between samples with similar accuracy to previously published studies, however with an increased breadth, querying all TSSs of the human genome.

mTSS-Seq Identifies Specific Nucleosome Architectures and Genome-Wide Nucleosome Distribution Alterations in the Progression of LAC A previous study conducted by the applicant herein demonstrated that nucleosome redistributions occurred at 50% of the ~900 TSS studied. It can be important to determine whether the widespread nature of these changes was limited to the loci studied in the previous investigation, or whether these changes were part of a larger genome wide nucleosomal reorganization. To investigate genome-wide changes in nucleosome distribution at the TSS, the difference between the normal and tumor datasets was calculated for each patient. Sorted difference maps of these data show that the grade one nucleosome distribution differences are widespread and dispersed throughout the genome, while these differences are greatly diminished in both grade three patients (FIG. 3A). Additionally, the difference maps show that the widespread changes observed exclusively in the grade one patients are associated with a lower occupancy in the tumor as compared to normal. These results demonstrate that the nucleosome distribution changes exclusive to the grade one tumors are widespread and shows lower occupancy at the TSS across the entire human genome.

Figure 3B:
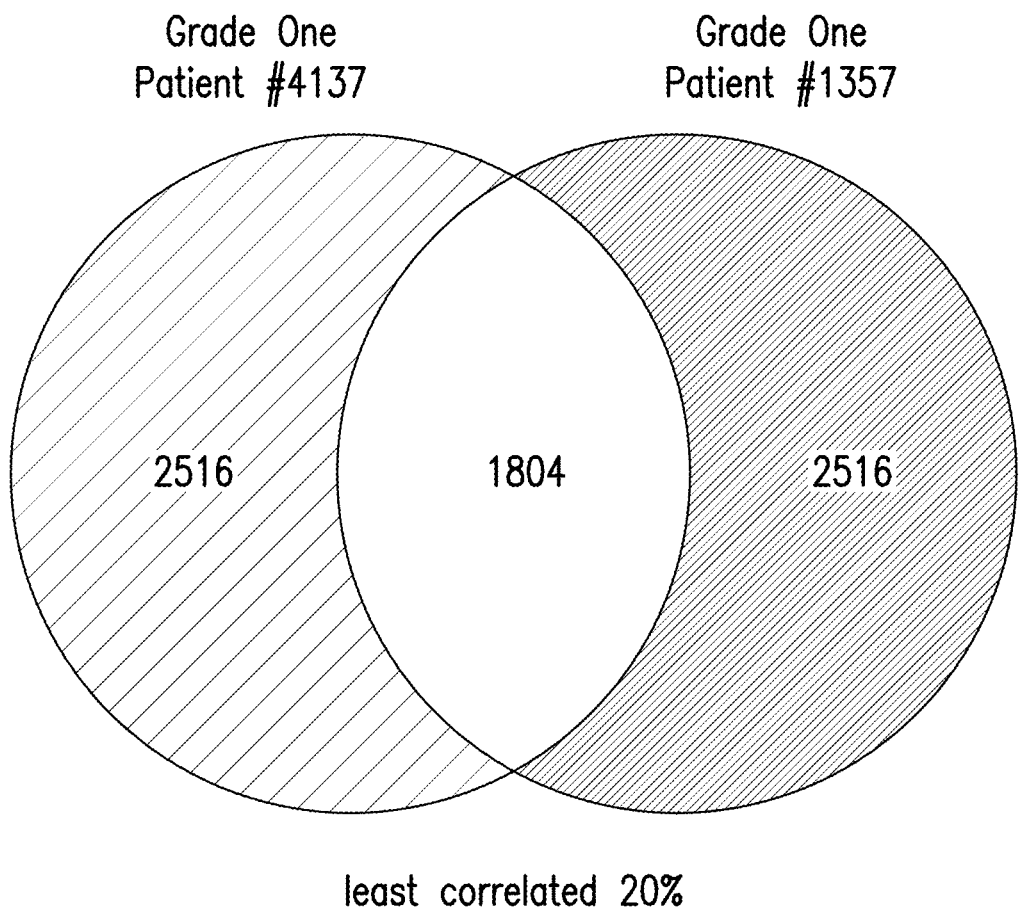
Figure 3C:
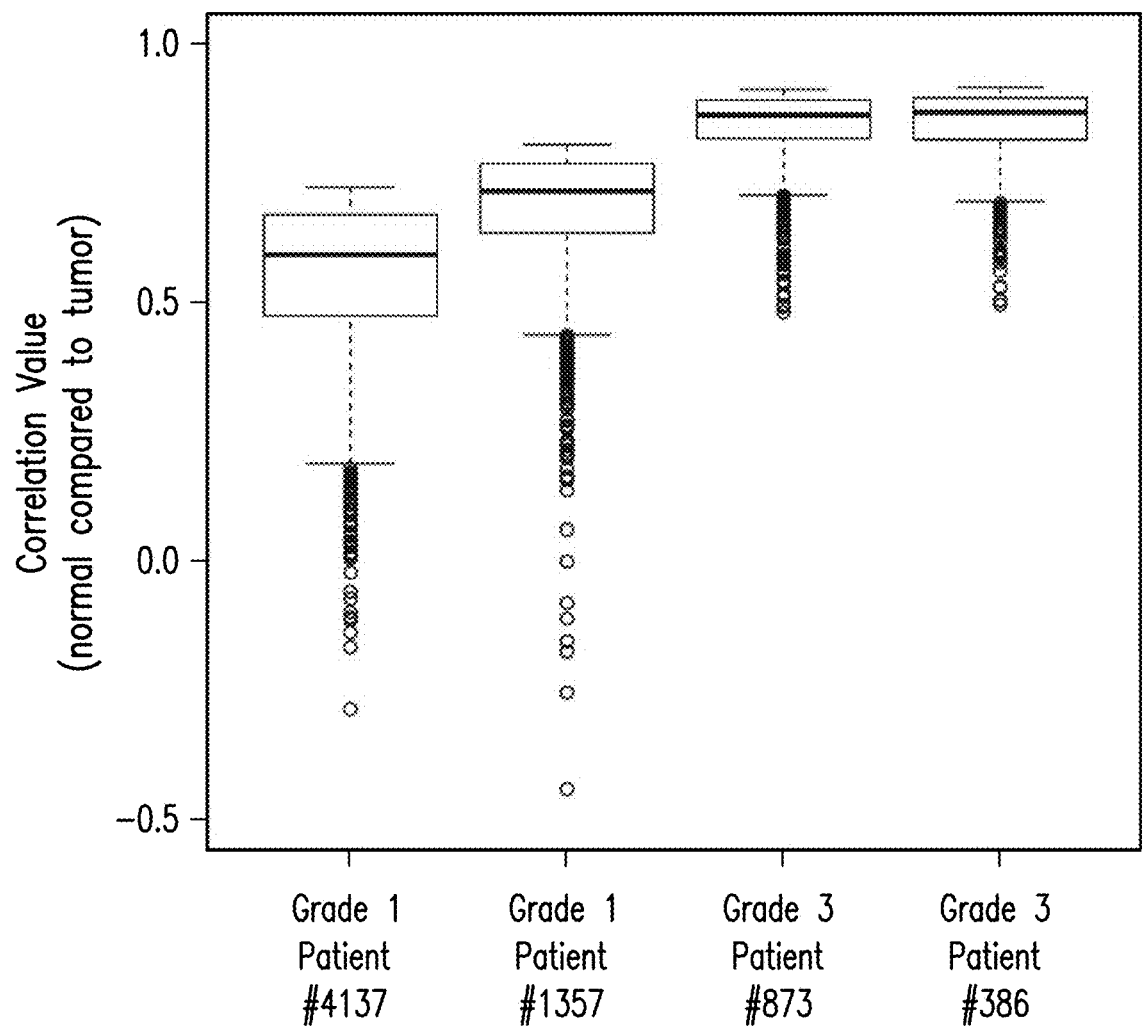

In order to determine if the genome wide nucleosome distribution changes in grade one tumors were similar between patients, the overlap was quantified in genes with nucleosome distribution alterations between the grade one patients. The correlation between normal and tumor for each grade one patient was first calculated for every gene, and then overlapping genes were identified in the least correlated 20% (~4,300 genes). It was found that 1,804 genes with the greatest degree of change between normal and tumor overlapped between the grade one patients (FIG. 3B). Additionally, the grade one patients showed a broad range of low correlation values (ranging from −0.5-0.8), whereas the grade three patients had a smaller range of values (ranging from 0.5-0.9) (FIG. 3C). The significant degree of overlap in nucleosome distribution changes suggests a concerted set of nucleosome distribution changes for these loci in early adenocarcinoma.

Figure 3D:
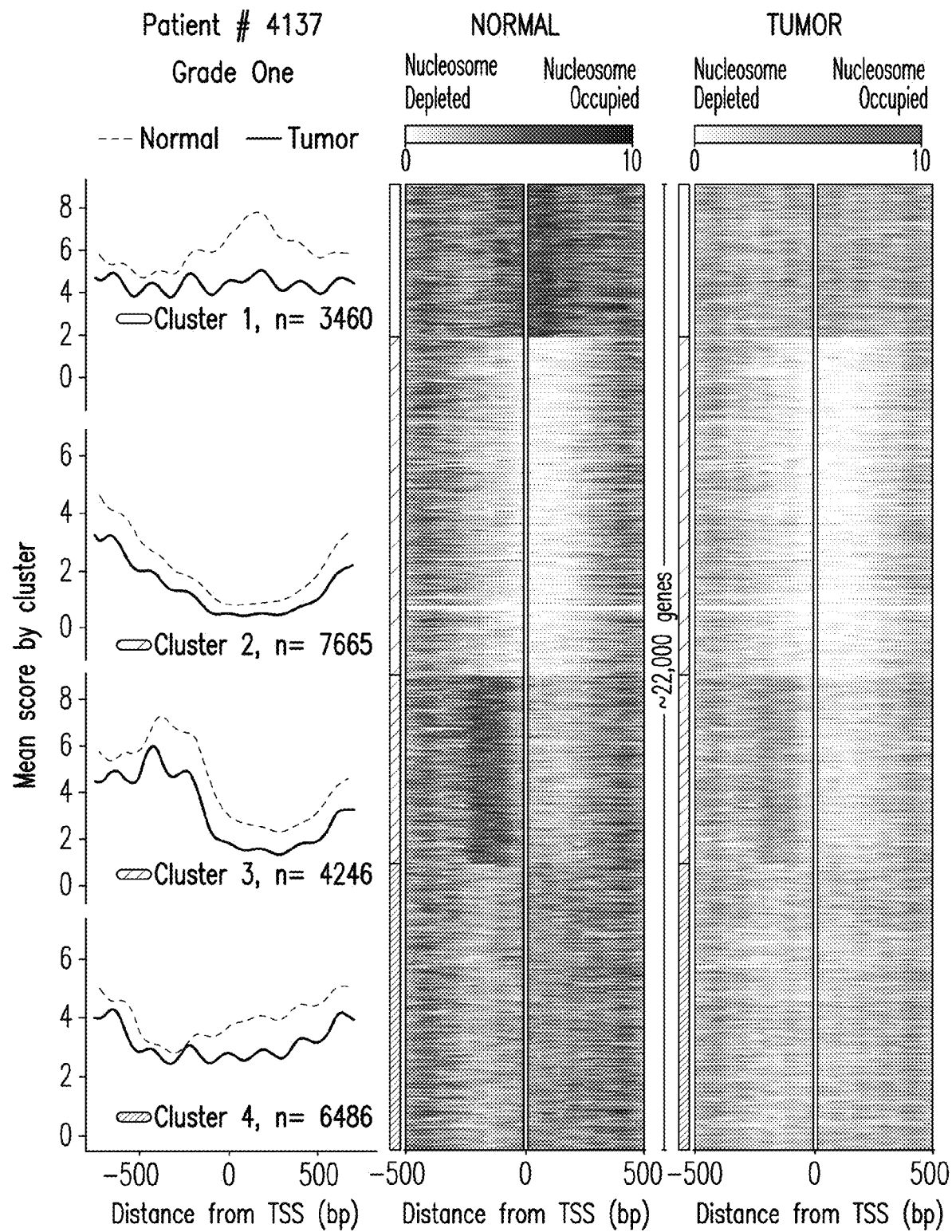

To test for nucleosome distribution organizations in the early tumors that might indicate shared chromatin structural events in early LAC, nucleosome profiles surrounding each TSS in the genome were categorized. k-means was used to align and cluster all genes based on nucleosome occupancy for a patient tumor and matched normal tissue (FIG. 3D). Since it was previously determined that four significantly distinct clusters defined nucleosome architectures, k=4 was used for k-means clustering of the data, and the profiles were grouped in a window of 1000 bp surrounding the TSS of the entire genome [Lee, W. et al. A high-resolution atlas of nucleosome occupancy in yeast. Nat Genet 39, 1235-1244 (2007)]. It was found that decreasing the number of clusters combined clusters 1 and 4, whereas increasing the number of clusters separated cluster 3 into two separate clusters (each new cluster emphasizing the −1 and −2 nucleosomes, respectively, which are shown together in the current cluster 3). Therefore, it was determined that four clusters showed the most distinct nucleosome architectures for primary LAC patient samples. It was observed that across the genome there are differences between the normal and tumor patient samples, with the most pronounced changes occurring in clusters 1 and 4. Both a global loss of nucleosome occupancy and increased nucleosome phasing in the tumor sample were shown. Clusters 1 and 4 display an impressive loss of nucleosomal occupancy upstream of the −1 nucleosome. These clusters indicate that changes in nucleosome occupancy in the grade one patients may play a role in the concerted gene regulation associated with transformation.

The next determination to be made was whether the 1,804 TSSs with altered nucleosomal structure shared in common between low-grade patients grouped into any particular cluster. It was found that the majority (76%) of the 1804 shared genes were located in clusters 1 (32%) and 4 (44%) (582 and 799, respectively). Upon testing whether genes in each cluster were enriched for any particular gene ontology (GO) process, it was found that each cluster had statistically significant GO enrichment (FIG. 3E) [Eden, E., et al. Discovering motifs in ranked lists of DNA sequences. PLoS Comput Biol 3, e39 (2007)]. Interestingly, genes in clusters 1 and 4 were each enriched for GO processes including chromatin and cancer-associated processes, such as nucleosome assembly, mRNA process, and mitotic G2 DNA damage checkpoint. Additionally, the genes in clusters 1 and 4 shared identical GO function for G-protein coupled receptor activity (P-value=$1.51\times10^{-19}$). Clusters 2 and 3 were enriched for genes with conventional cell and molecular processes.

Figure 4A:
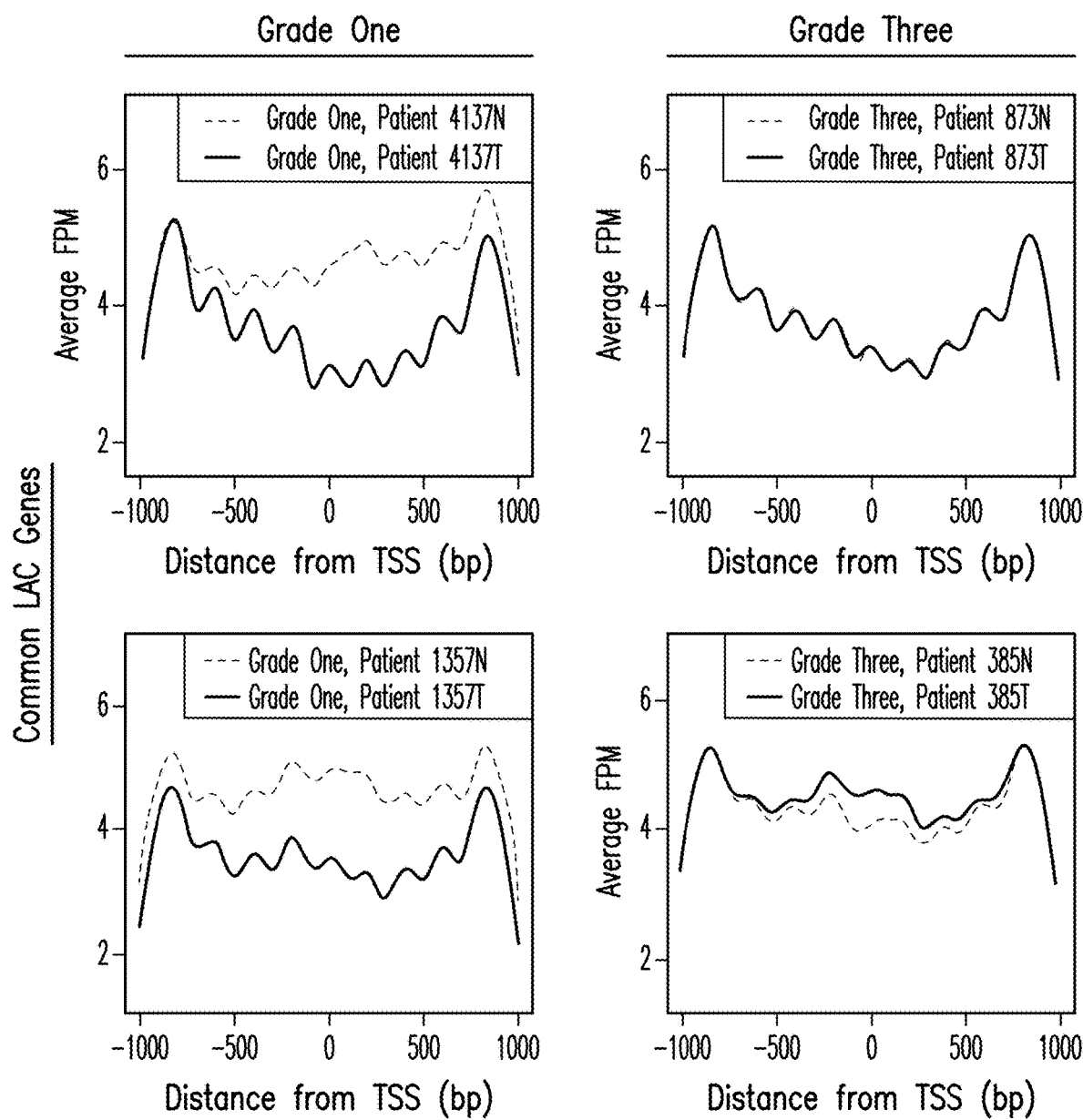
FIGS. 4A-4F are average and gene-specific plots showing many nucleosome distribution changes being consistent between patients in low-grade tumors and minimal changes in high-grade tumors.
Figure 4B:
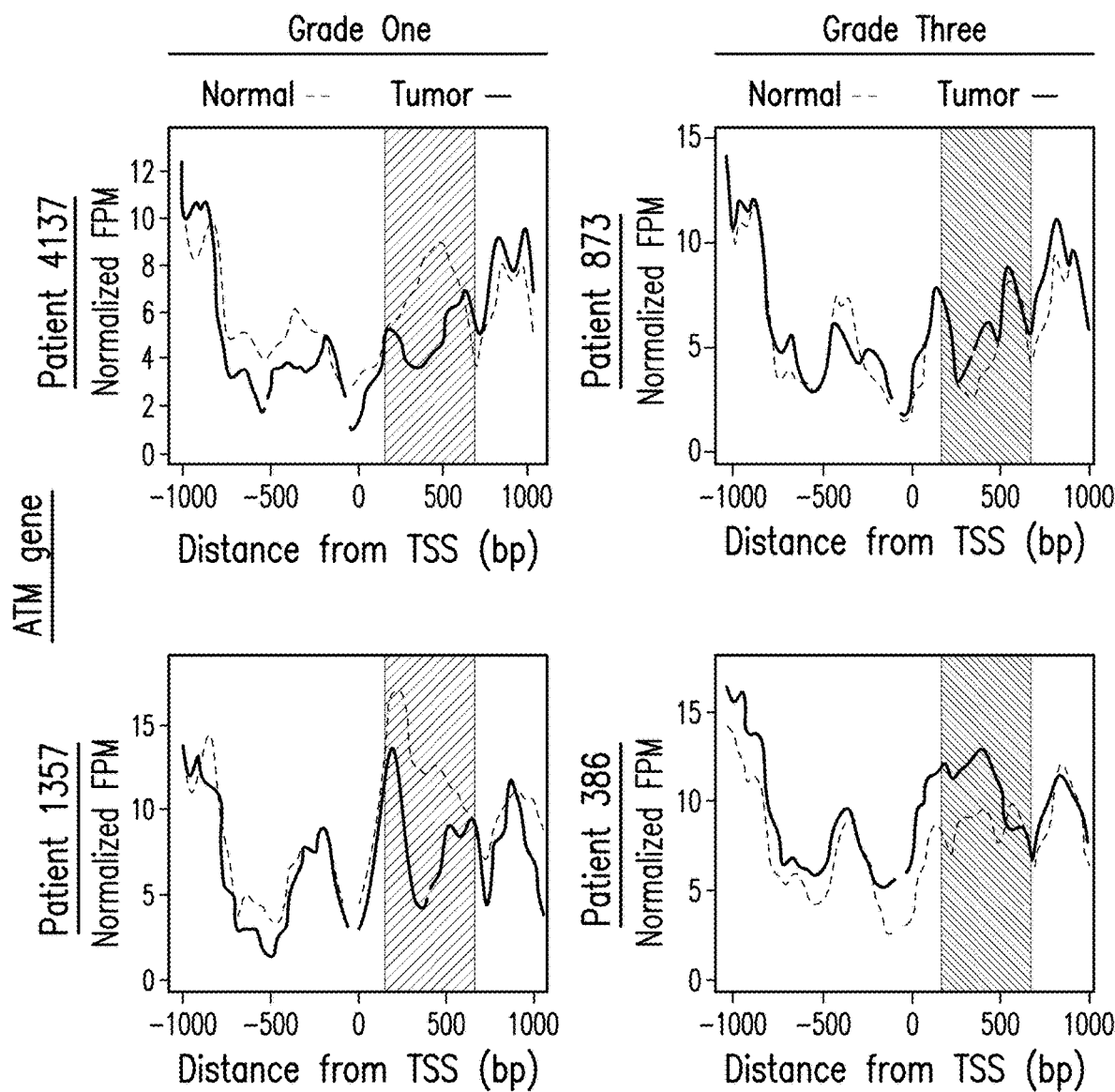
Figure 4C:
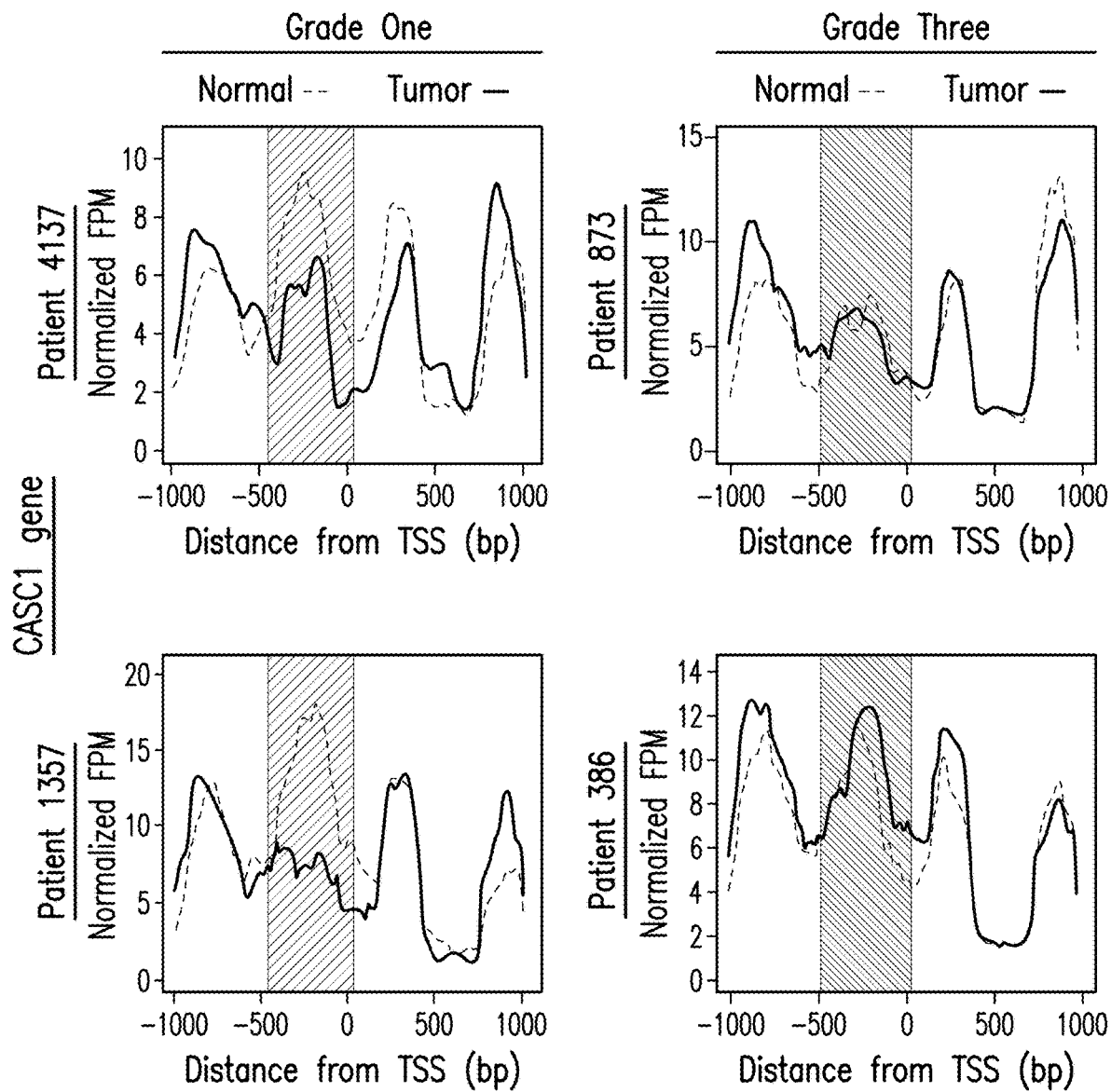
Figure 4D:
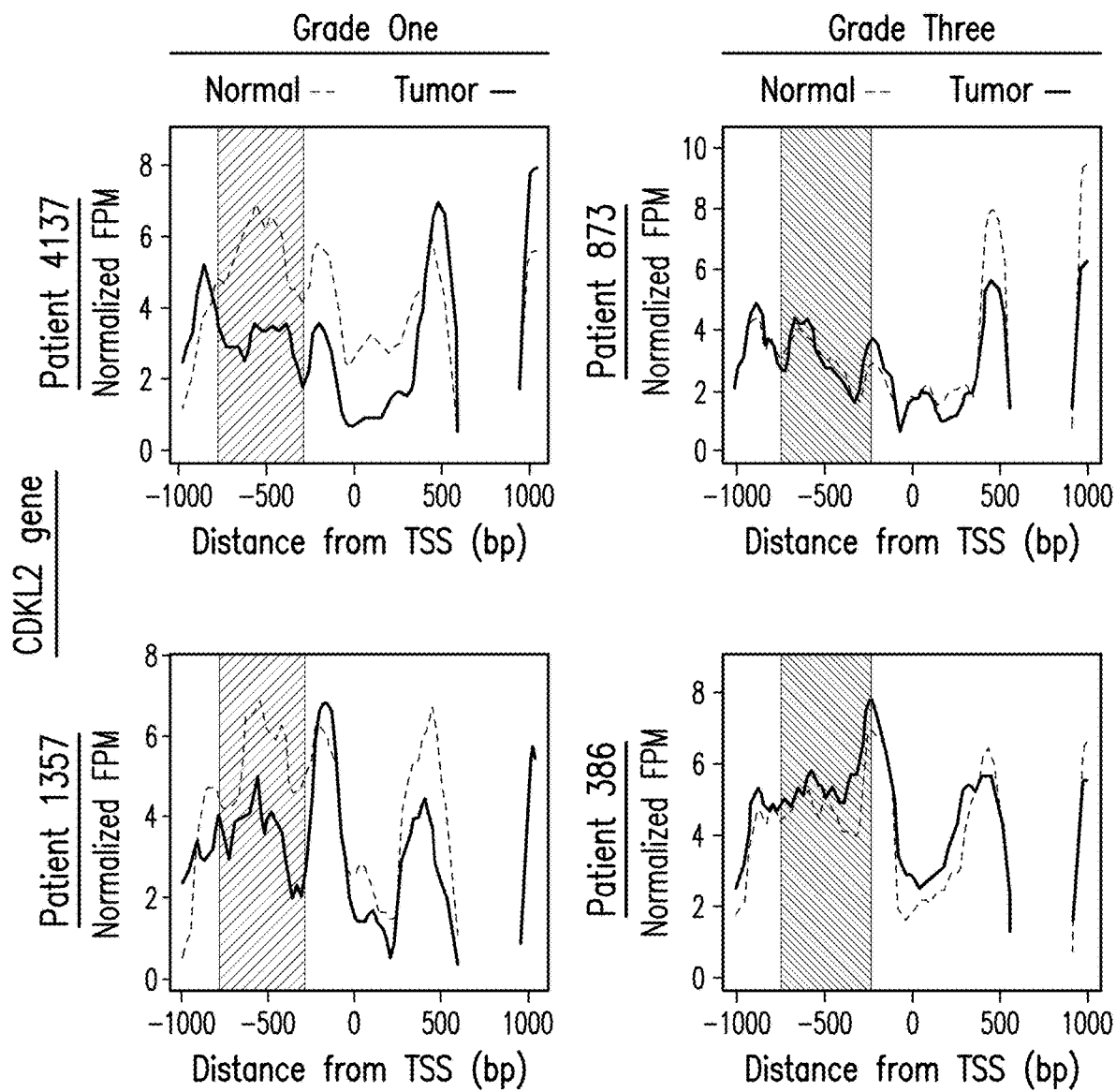
Figure 4E:
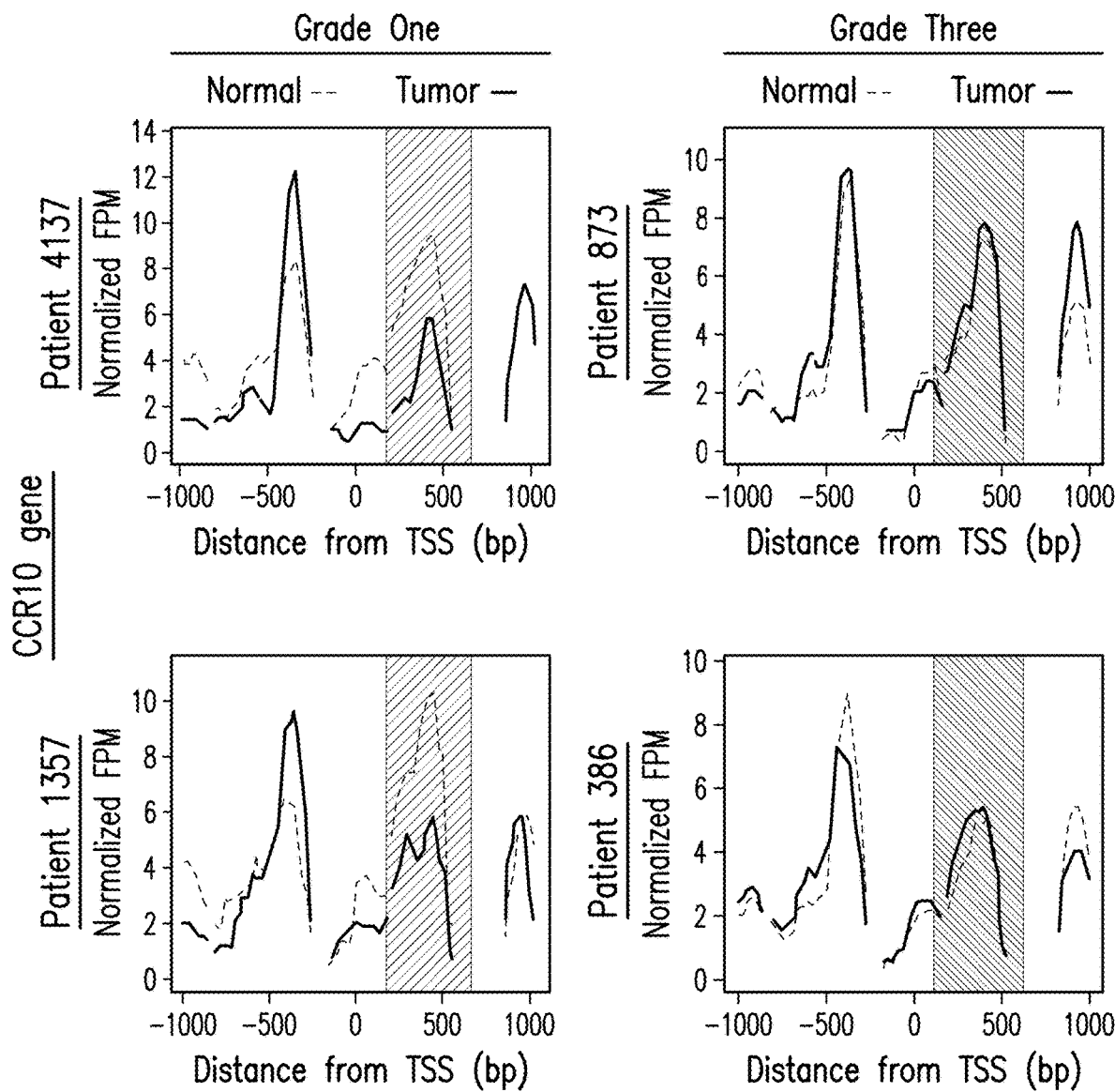
Figure 4F:
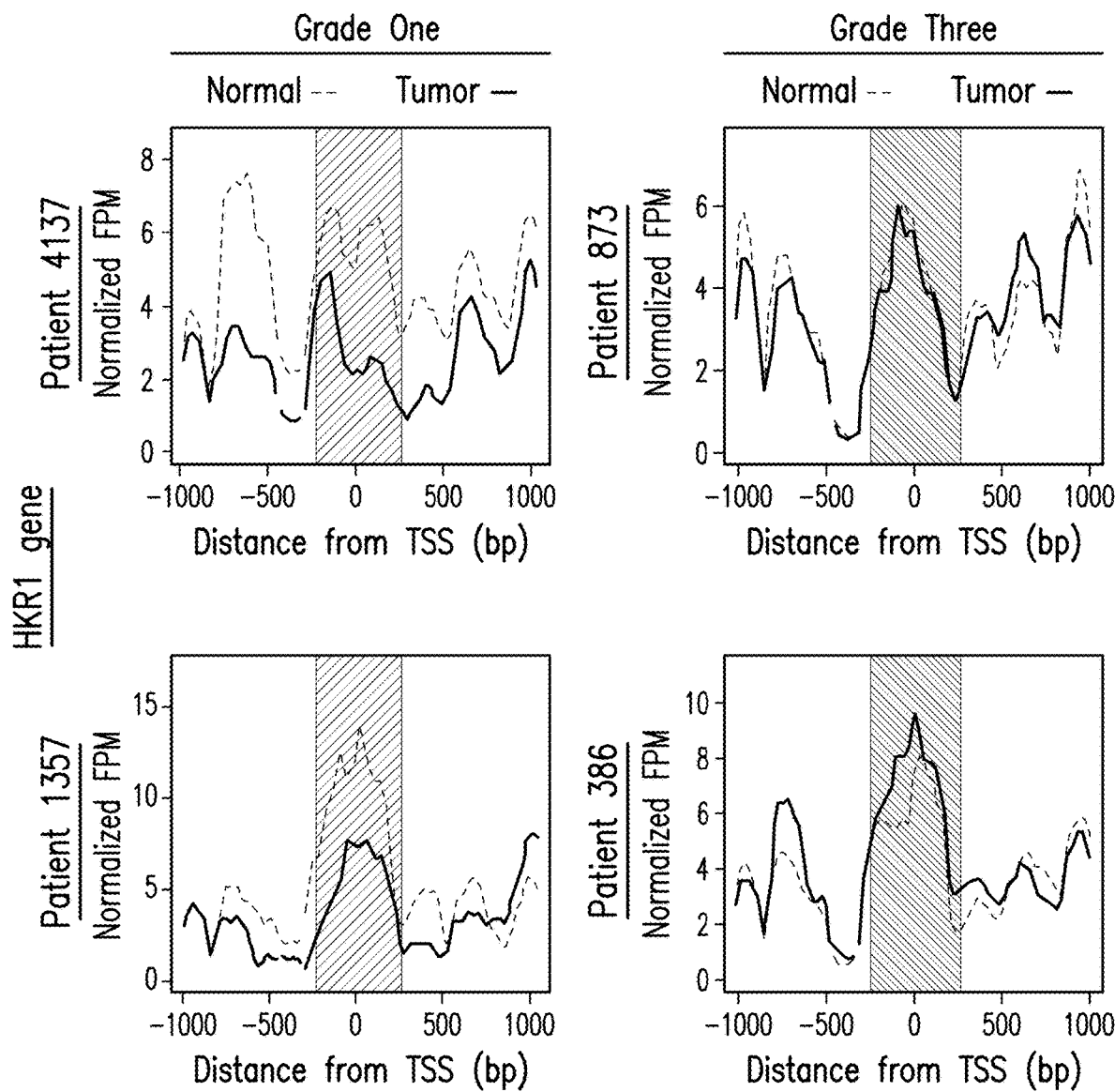

Nucleosome Distribution Alterations are Consistent Among Patients with Early LAC The similarity in the degree of difference between normal and tumor tissue for the grade one patients, the high overlap between patients for loci with altered nucleosome distribution, and the enrichment of those loci in related ontological categories indicated consistency between patients. Next, the nucleosome redistributions were visually inspected at specific loci to see whether the nucleosome distribution patterns at individual loci were similar between patients. The average nucleosome distribution plots for the 1,804 shared grade one genes showed many changes in nucleosome distribution among the grade one patients, and few changes among the grade three patients (FIG. 4A). The loss of occupancy in the grade one tumor is particularly clear in these average plots, with a majority of this loss occurring downstream of the TSS. FIG. 4 shows five representative genes that are misregulated in adenocarcinoma: ATM, CASC1, CDKL2, CCR10, and HKR1 (FIGS. 4B-4F) [Bakhoum, S. F., Thompson, S. L., Manning, A. L. & Compton, D. A. Genome stability is ensured by temporal control of kinetochore-microtubule dynamics. Nat Cell Biol 11, 27-35 (2009); Ding, L. et al. Somatic mutations affect key pathways in lung adenocarcinoma. Nature 455, 1069-1075 (2008); Goldberg, A. D., Allis, C. D. & Bernstein, E. Epigenetics: a landscape takes shape. Cell 128, 635-638 (2007); Hill, V. K. et al. Genome-wide DNA methylation profiling of CpG islands in breast cancer identifies novel genes associated with tumorigenicity. Cancer Res 71, 2988-2999 (2011); Kim, T. M. et al. Genome-wide screening of genomic alterations and their clinicopathologic implications in non-small cell lung cancers. Clin Cancer Res 11, 8235-8242 (2005); Kohno, T. et al. Association of KRAS polymorphisms with risk for lung adenocarcinoma accompanied by atypical adenomatous hyperplasias. Carcinogenesis 29, 957-963 (2008); Kundel, D. W. et al. Molecular characterizations of Nop16 in murine mammary tumors with varying levels of c-Myc. Transgenic Res 21, 393-406 (2012); Liu, P. et al. Candidate lung tumor susceptibility genes identified through whole-genome association analyses in inbred mice. Nat Genet 38, 888-895 (2006); Sarvaiya, P. J., Guo, D., Ulasov, I., Gabikian, P. & Lesniak, M. S. Chemokines in tumor progression and metastasis. Oncotarget 4, 2171-2185 (2013): Webb, E. L. et al. Search for low penetrance alleles for colorectal cancer through a scan of 1467 non-synonymous SNPs in 2575 cases and 2707 controls with validation by kin-cohort analysis of 14 704 first-degree relatives. Hum Mol Genet 15, 3263-3271 (2006); Yang, H. et al. ATM sequence variants associate with susceptibility to non-small cell lung cancer. Int J Cancer 121, 2254-2259 (2007)]. In each case, the locus showed substantial differences between the grade-one patient normal and tumor samples. In a majority of cases, it was found that specific nucleosome distribution changes were consistent between and unique to the grade-one tumors (FIGS. 4B-4F, "Grade One" column, highlighted). Grade-three tumor samples rarely deviated from the nucleosome distribution pattern seen in normal tissue (FIGS. 4B-4F, "Grade Three" column, gray shaded). These results confirm a common mechanism driving the nucleosome distribution changes in the grade one tumors.

Nucleosome Distribution Changes are Driven by DNA Sequence

Given the commonalities between the nucleosome distribution changes between the patients, the influences driving the nucleosome distribution changes in the grade one samples should be understood. Nucleosome distributions are governed by the interplay between regulatory complexes, such as transcription factors and chromatin remodelers, and features intrinsic to the DNA sequence. The extent to which DNA sequence contributed to the grade-one changes should be determined. The experimentally determined nucleosome distributions were compared to computationally predicted nucleosome occupancy scores based solely upon primary sequence [Gupta, S. et al. Predicting human nucleosome occupancy from primary sequence. PLoS Comput Biol 4, e1000134 (2008); Sexton, B. S. et al. The spring-loaded genome: nucleosome redistributions are widespread, transient, and DNA-directed. Genome Res 24, 251-259 (2014)]. It was reasoned that if DNA sequence played a role in in these distributions, then the predictions based upon the computational model would match the measured nucleosome distributions in the grade-one samples.

Figure 5A:
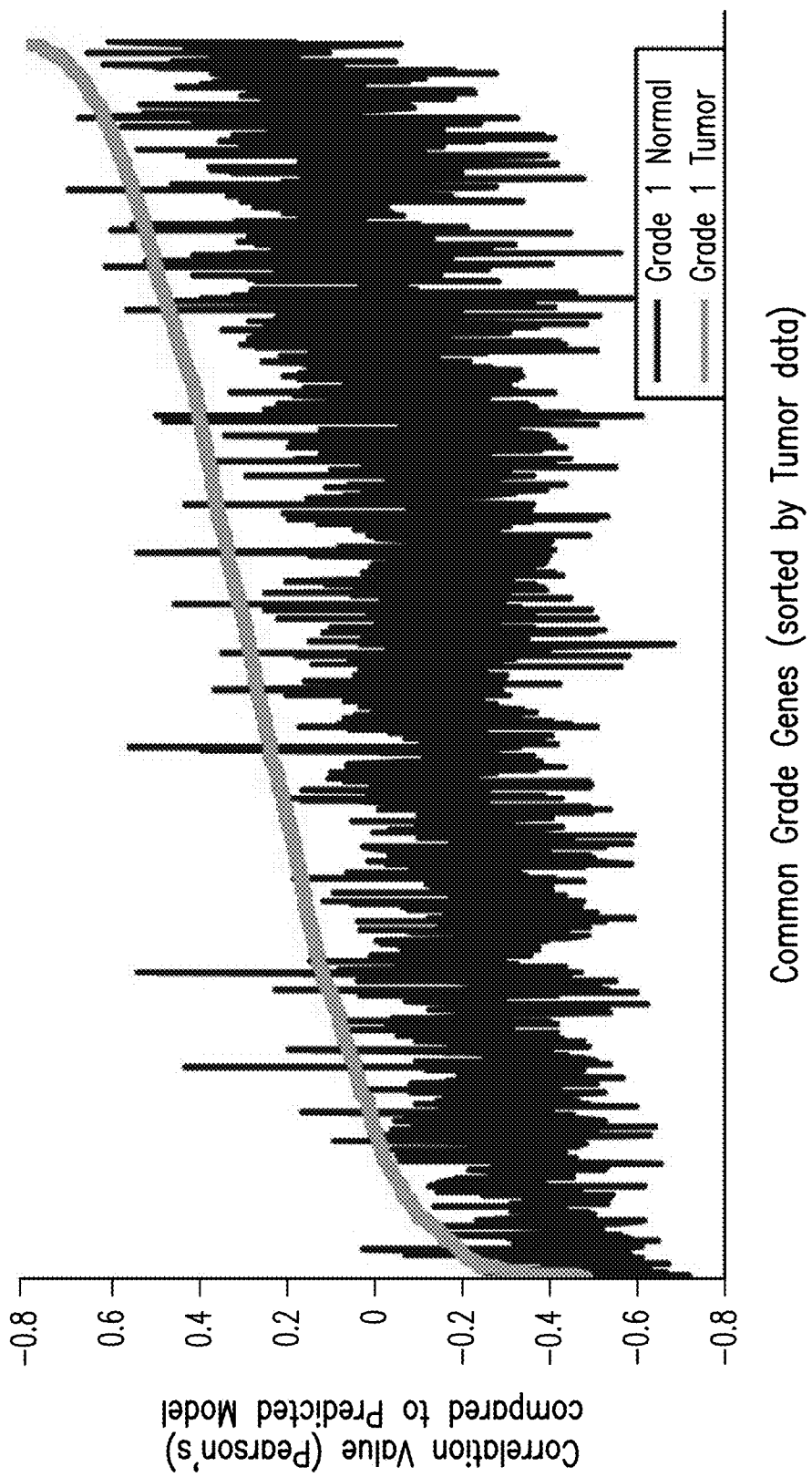
FIGS. 5A-5F show nucleosome distribution changes driven by DNA sequence.
Figure 5B:
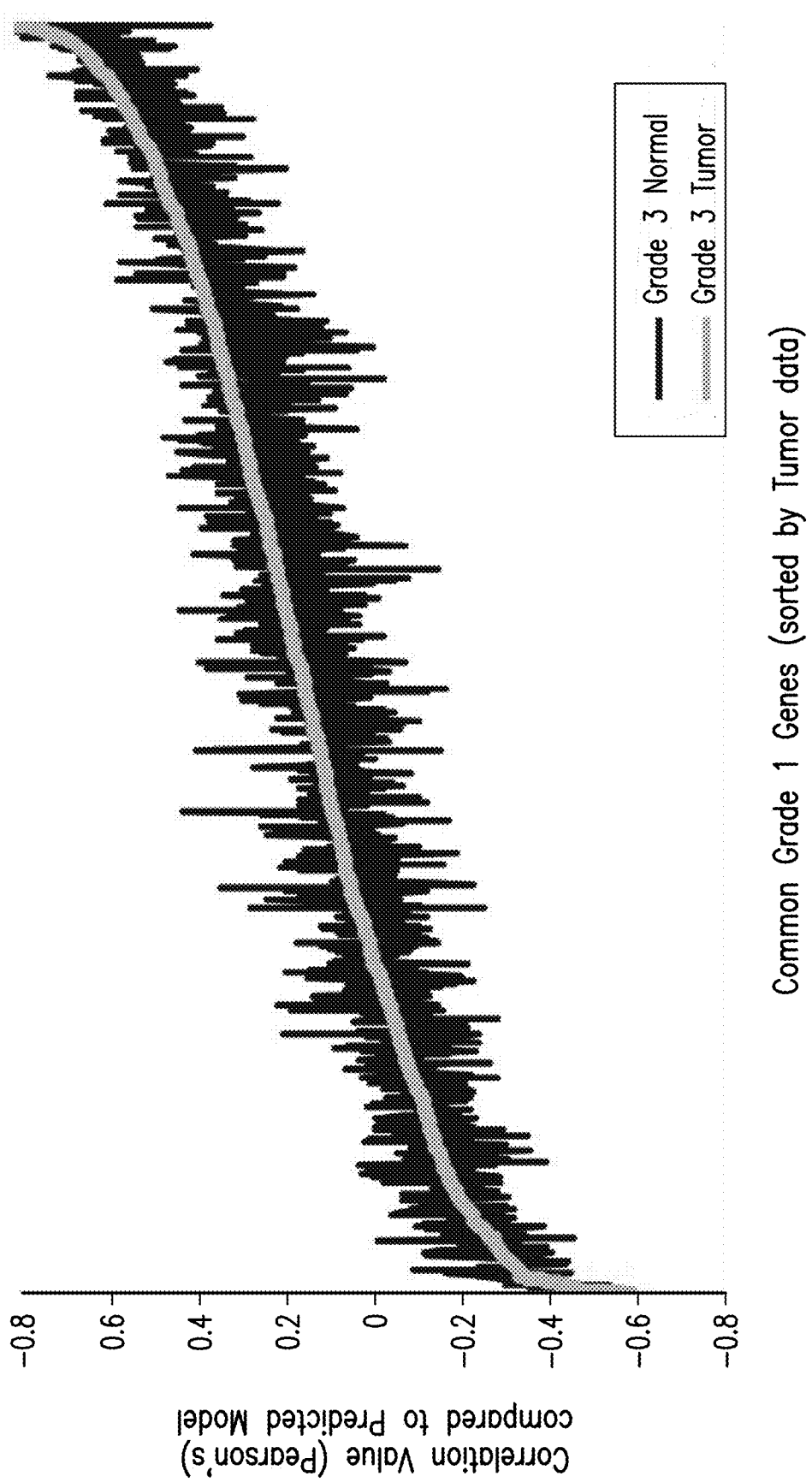
Figure 5C:
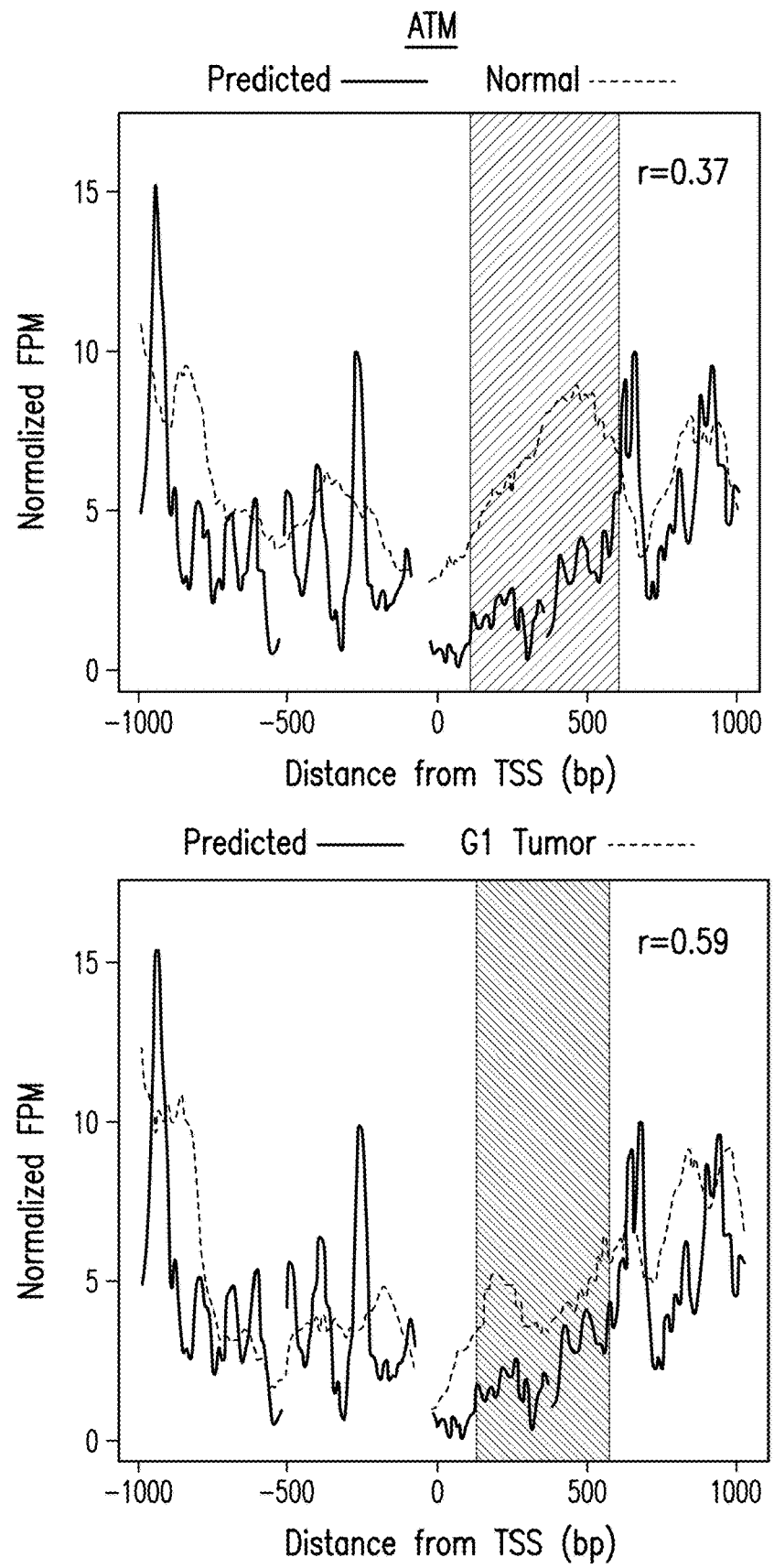
Figure 5D:
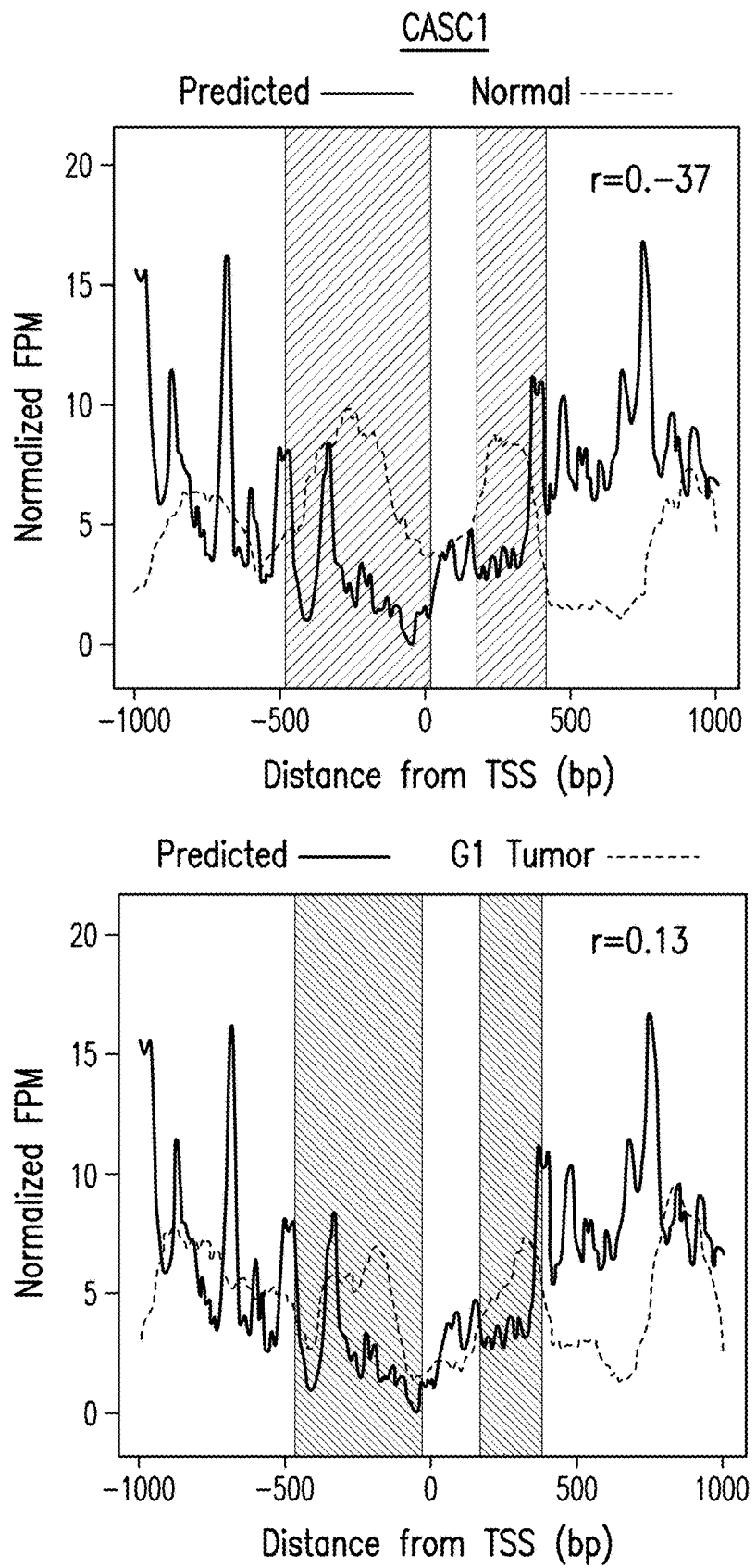
Figure 5E:
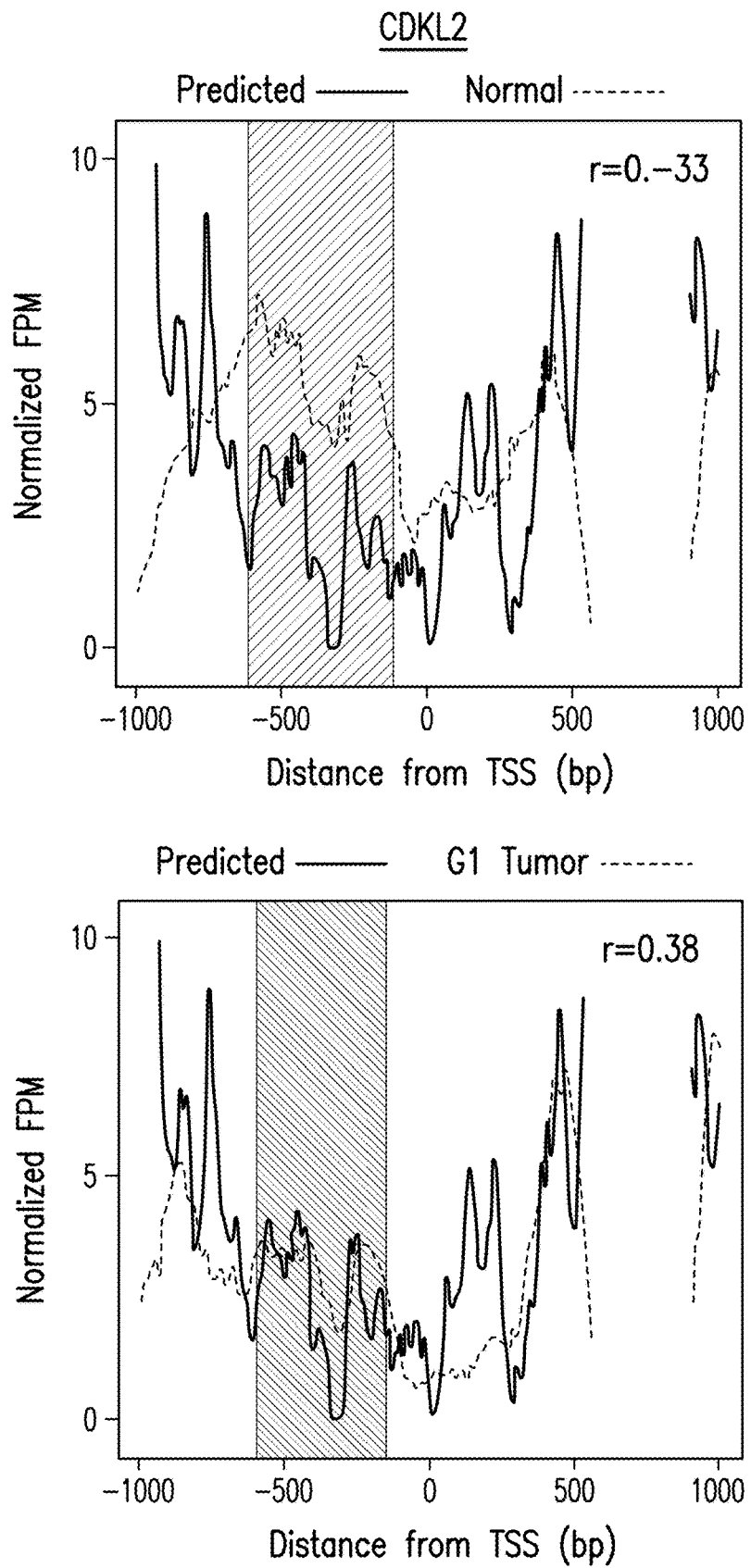
Figure 5F:
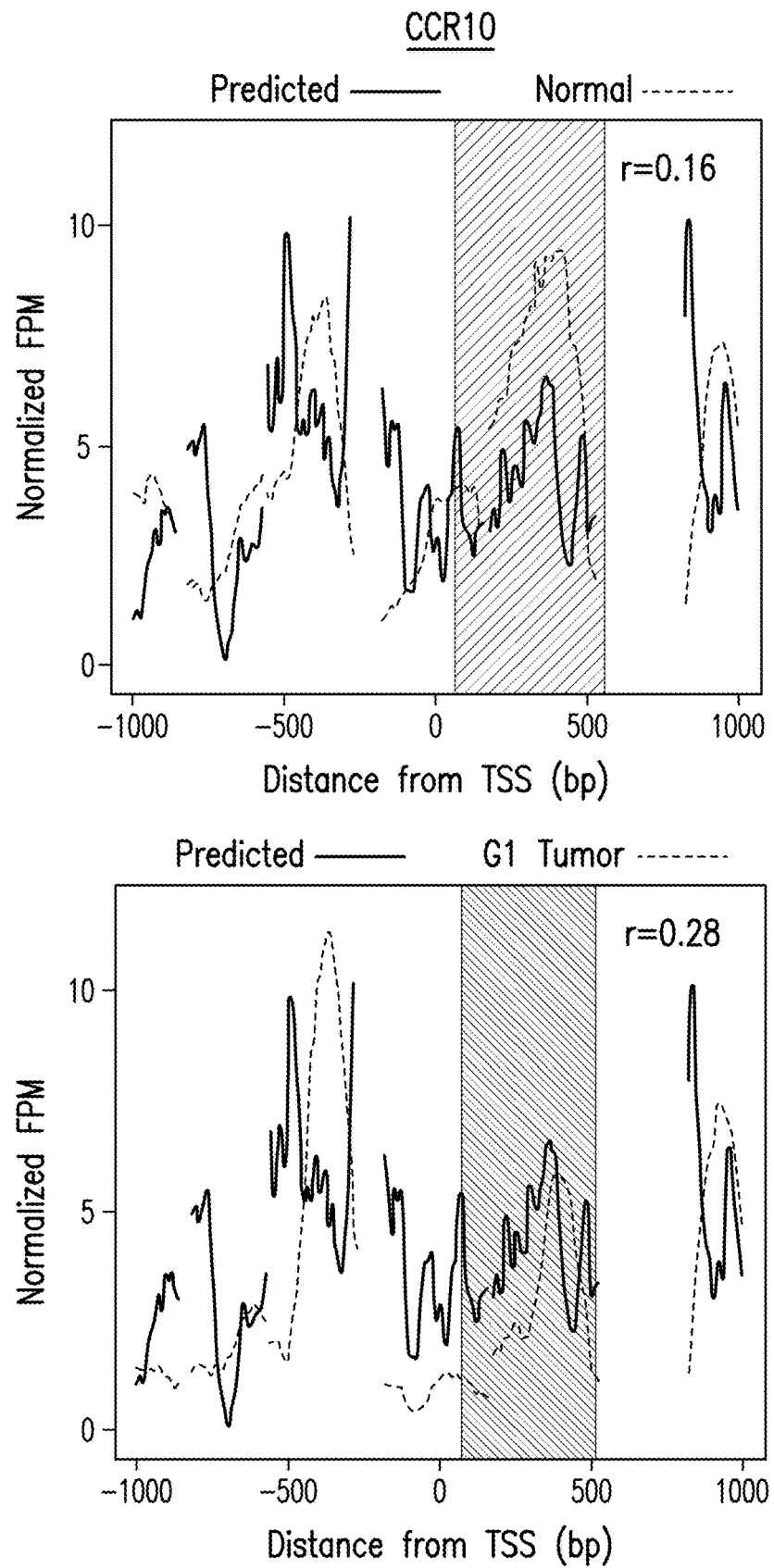

Of the 1,804 loci with nucleosome distribution changes shared between the grade-one patients, an average of ~1,500 genes (85%) had a higher correlation with the DNA-encoded nucleosome positions than the matched normal sample, indicating that those loci are moving to positions favored by the underlying DNA sequence (FIG. 5A). In contrast, the same loci in the grade three tumors did not show increased agreement with the DNA-encoded positions; rather, the correlations between the grade three tumor and model based on DNA sequence were similar to those between the matched normal and model. Overall, the loci for the average grade one tumor data showed an average 215% increase in correlation with the computational model, as compared with the average normal data. The grade three tumors showed a 17% decrease in correlation to the computational model compared to normal.

The DNA-directed nature of grade one tumor nucleosome distribution changes were then determined at individual loci. The nucleosome distribution data were co-plotted with the DNA-based model of nucleosome occupancy at the representative loci analyzed earlier. The agreement between the grade one nucleosome redistributions and the positions directed by the underlying DNA sequence was evident when the measured and predicted nucleosome distributions were plotted at specific loci (FIGS. 5C-5F). The correlation coefficient was always highest in the predicted versus grade-one data. These results suggest that DNA-encoded signals direct nucleosomes to default positions upon transformation in early LAC.

Altered Nucleosome Distribution in LAC Potentiates Transcription Factor Binding

To investigate whether the nucleosome distribution changes in the grade one tumors exposed DNA at loci for genomic licensing, the proportion of subnucleosomal MNase protected fragments at regulatory factor binding sites was measured. It has been shown that subnucleosomal fragments (<100±20 bp) derived from MNase digestion of DNA may act as a proxy for protection by DNA-binding proteins, such as transcription factors [Kent, N. A., et al. Chromatin particle spectrum analysis: a method for comparative chromatin structure analysis using paired-end mode next-generation DNA sequencing. Nucleic Acids Res 39, e26 (2011); Henikoff, J. G., et al. Epigenome characterization at single base-pair resolution. Proc Natl Acad Sci USA 108, 18318-18323 (2011)]. In order to determine whether transcription factor binding occurred in the context of nucleosome redistributions in LAC, regions of difference between normal and tumor were first calculated throughout all TSSs for grade one and grade three patients. About 18,000 regions of difference in the grade one and about 6,000 regions of difference in the grade three samples were found by this method (FIG. 6A) w.

Figure 9A:
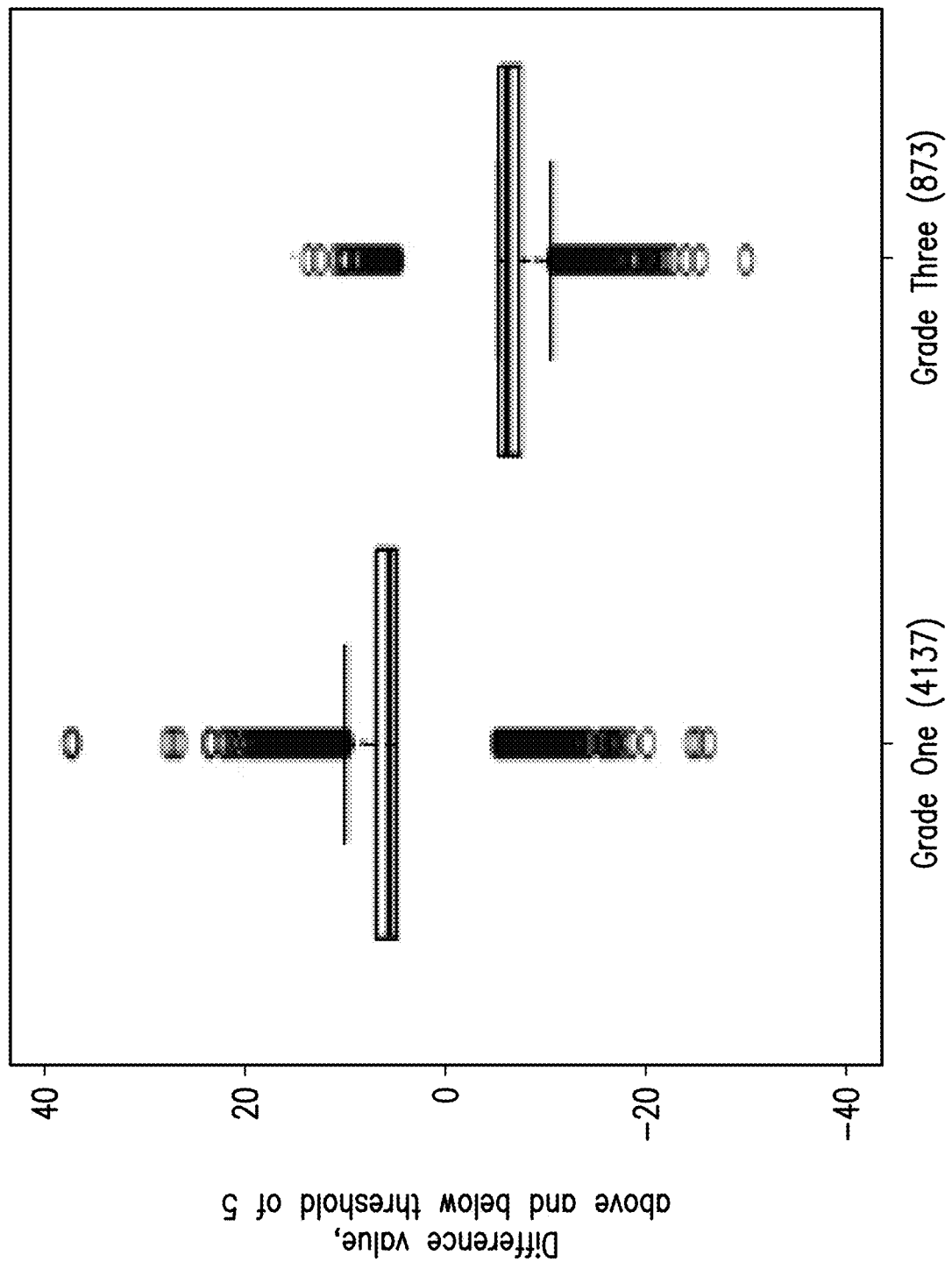
FIGS. 9A-9D are graphical illustrations indicating that low grade patients show a greater degree of difference than the grade three patients.
Figure 9B:
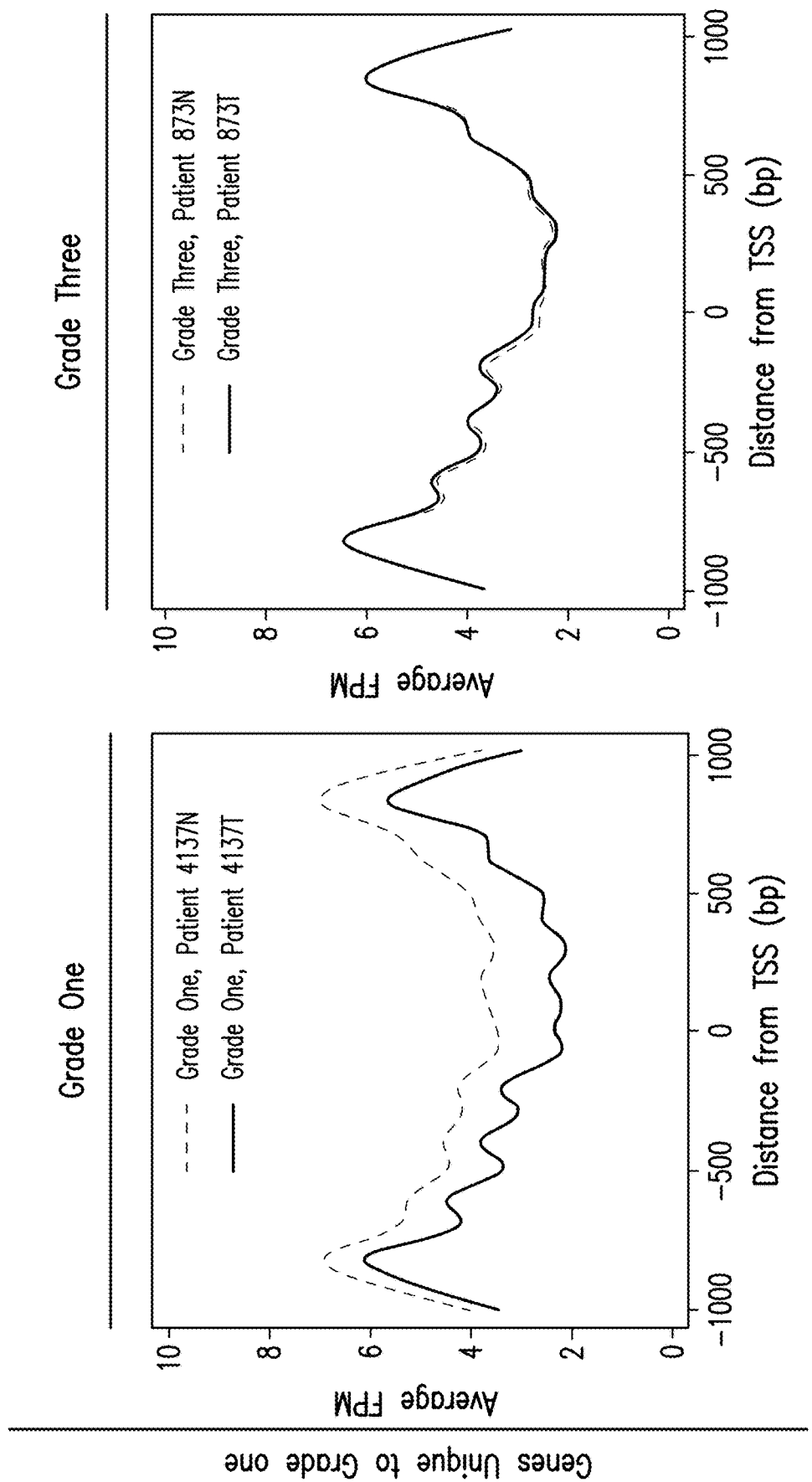
Figure 9C:
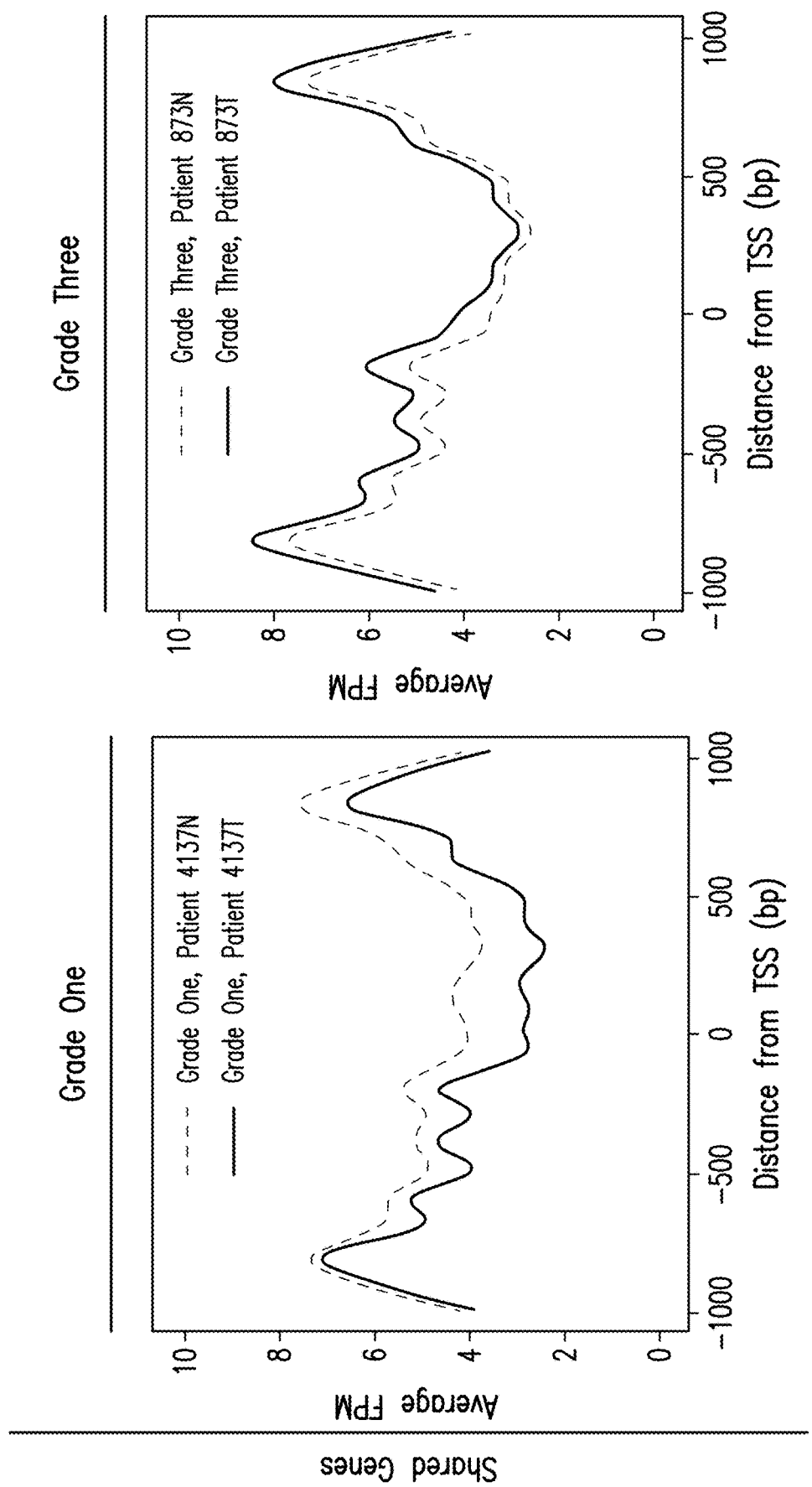
Figure 9D:
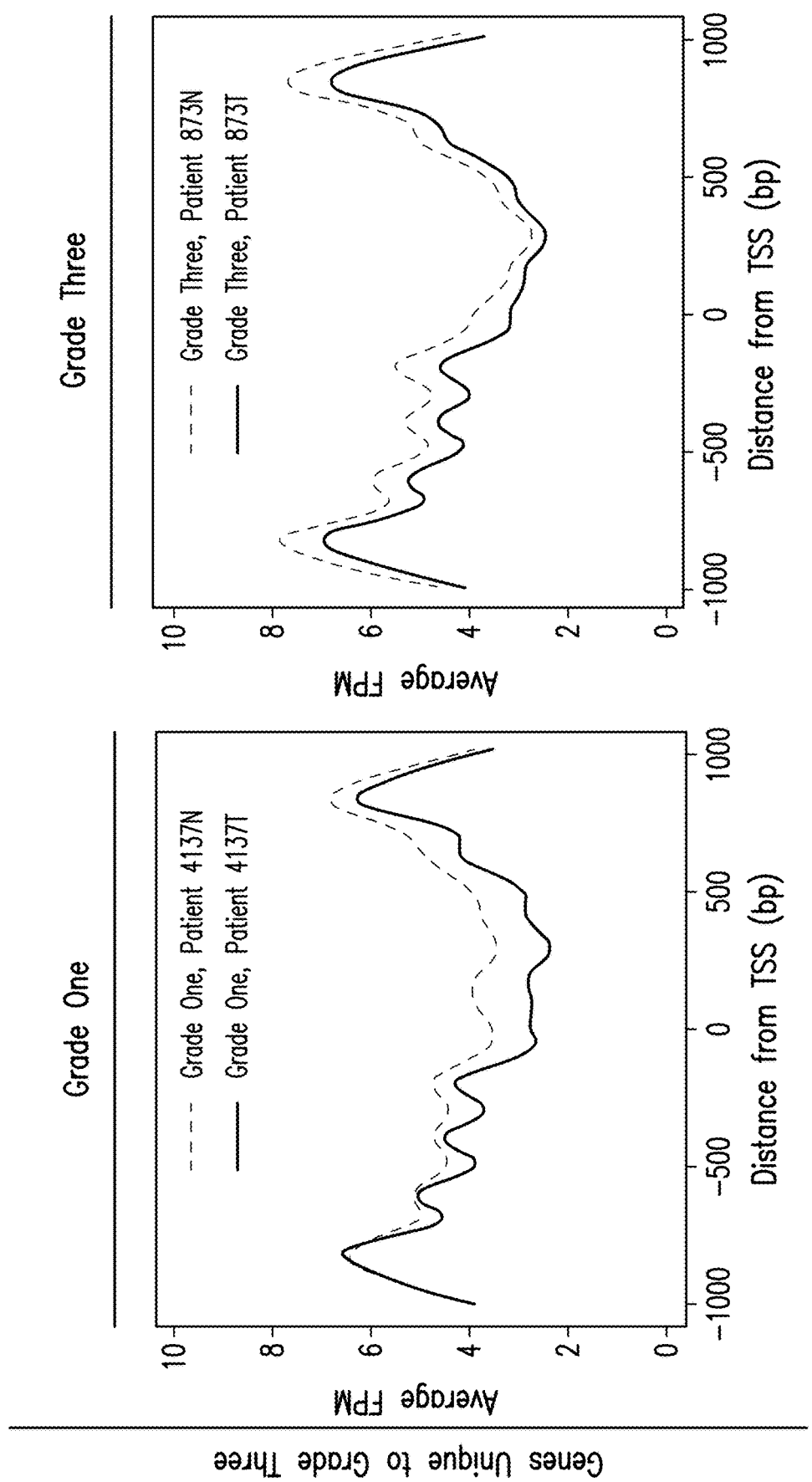

The threshold applied to determine regions of difference was the most stringent cut-off that discriminated between the samples, while revealing a substantial enough number of regions to perform downstream analyses in the grade three patients since there were far fewer regions of difference than in the grade one patients. Overall, the total difference values for the grade one patients have a much higher range than the values for grade three patients. Therefore, although a region was determined above a threshold, the difference value was reliably lower in the grade three compared to the grade one patients, agreeing with earlier observations that changes in nucleosome distribution occur early in the progression of cancer (FIG. 9A).

Figure 6A:
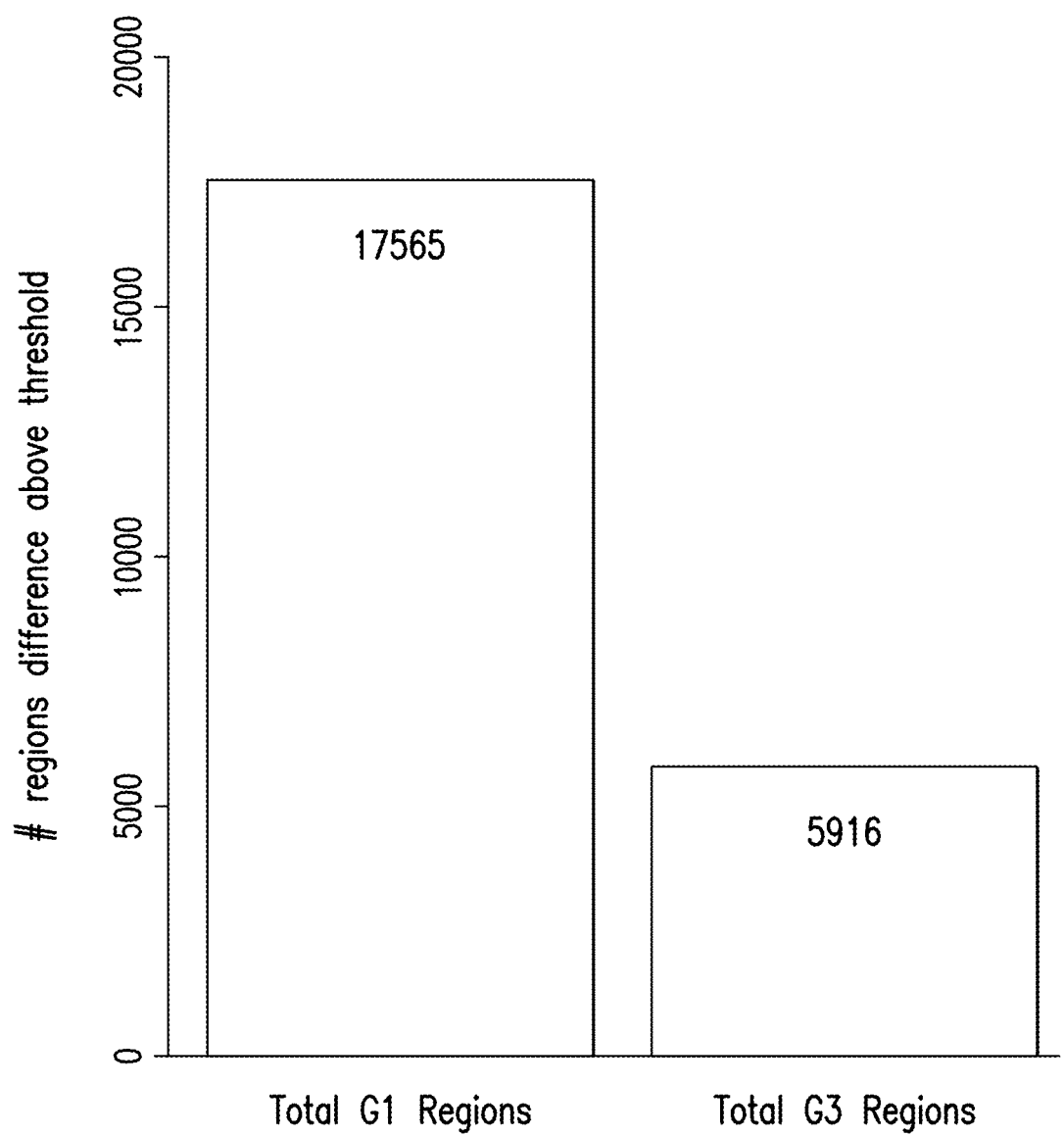
FIGS. 6A-6F depict altered nucleosome distribution in LAC potentiates transcription factor binding.
Figure 6B:
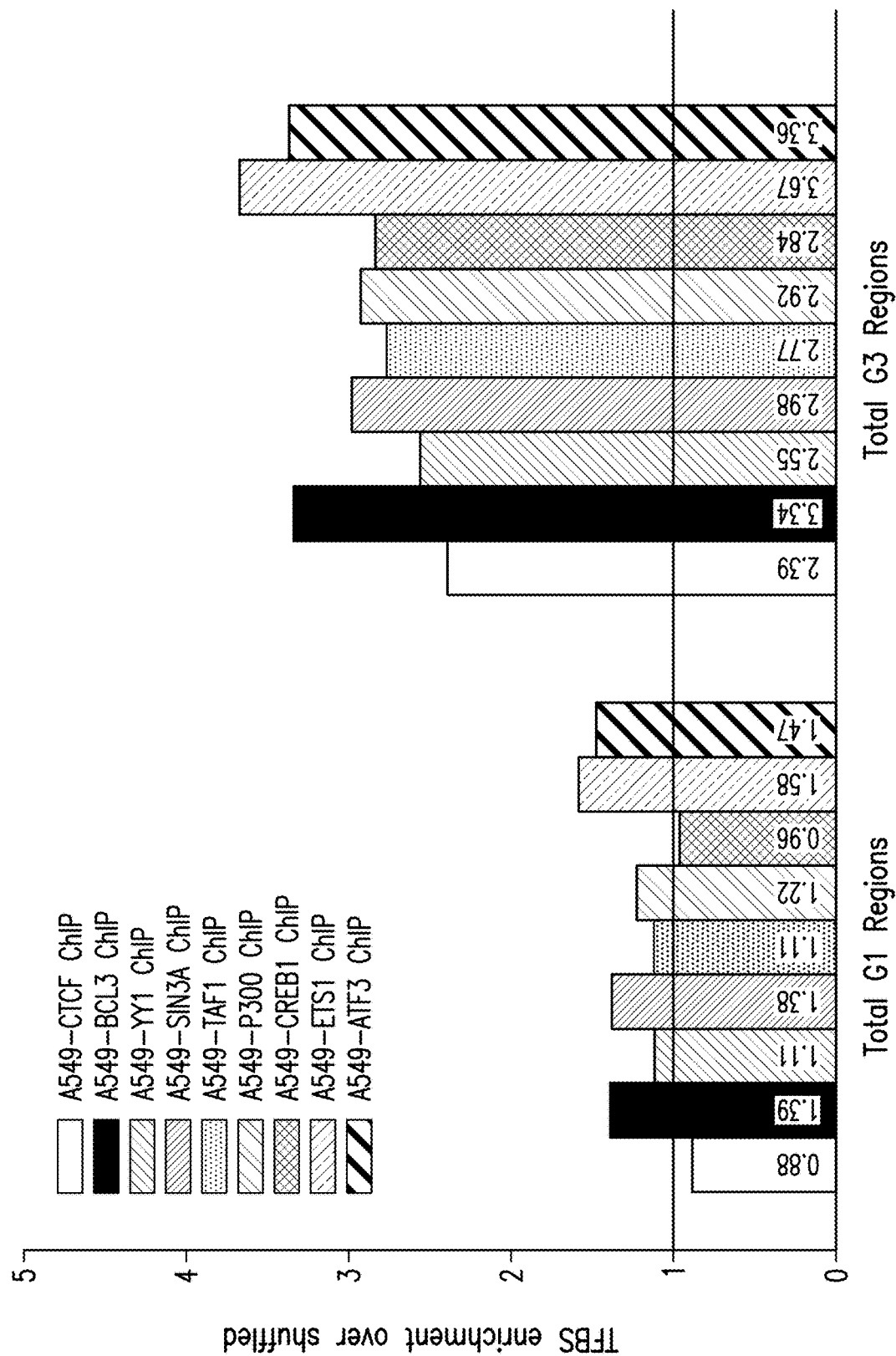
Figure 6C:
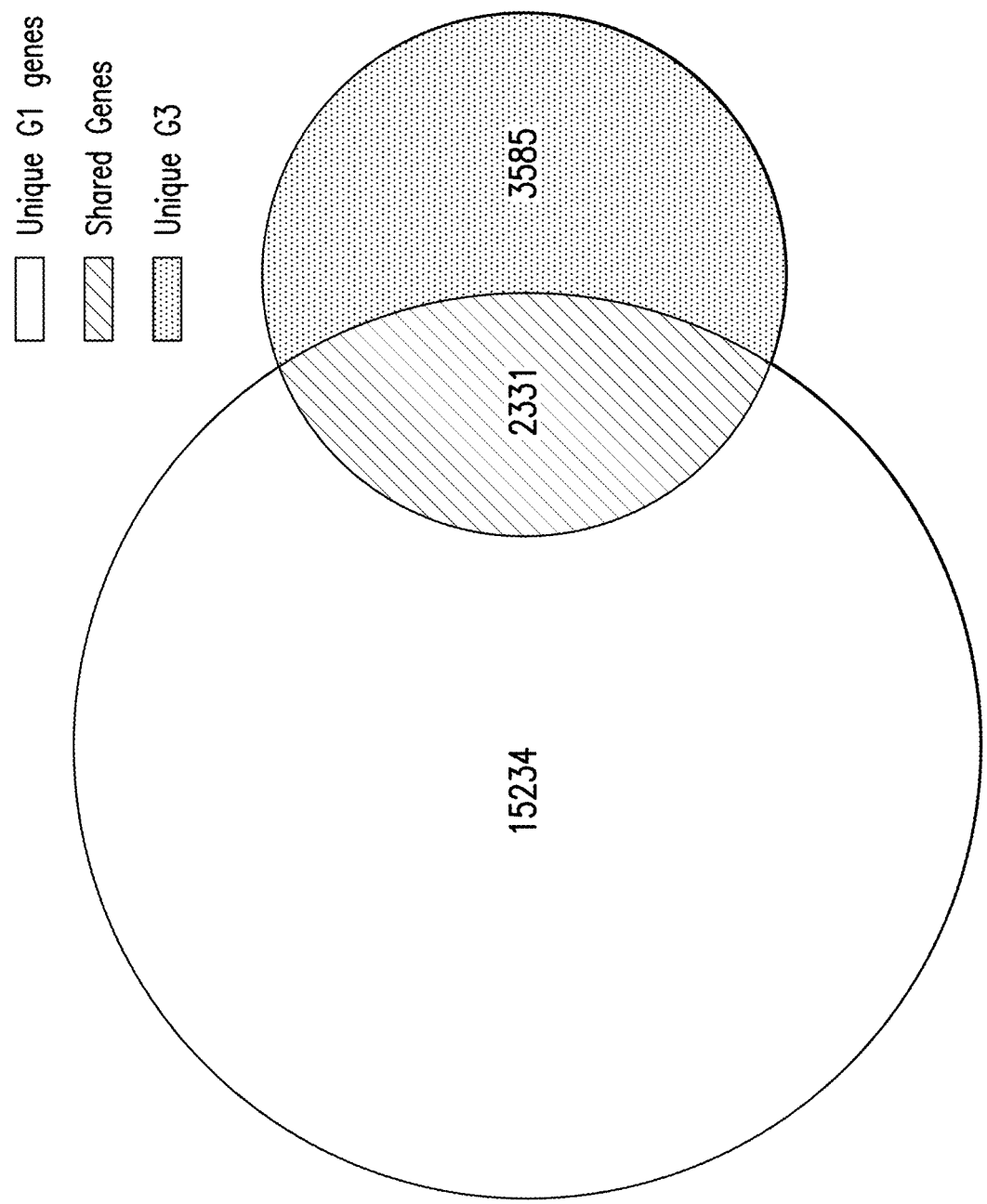

Using transcription factor binding site (TFBS) data identified by ChIP-seq in a lung adenocarcinoma cell line (A549), binding sites were quantified for nine transcription factors Ctcf (GSM803456), Bcl3 (GSM1010775), Yy1 (GSM1010794), Sin3a (GSM1010882), Taf1 (GSM1010812), P300 (GSM1010827), Creb1 (GSM1010719), Ets1 (GSM1010829) and Atf3 (GSM1010789) at the regions of difference in grade one and grade three patients 42. In order to determine enrichment, the TFBSs identified in the A549 study were shuffled, and then a ratio of the number of binding events was calculated in the regions of difference to that shuffled control (a value of one indicates no significant enrichment or depletion compared to the shuffled data). Significant enrichment over shuffled TFBSs tested was found at regions of difference in the grade three patients, and depletion of TFBSs in the grade one patients (FIG. 6B).

Figure 6D:
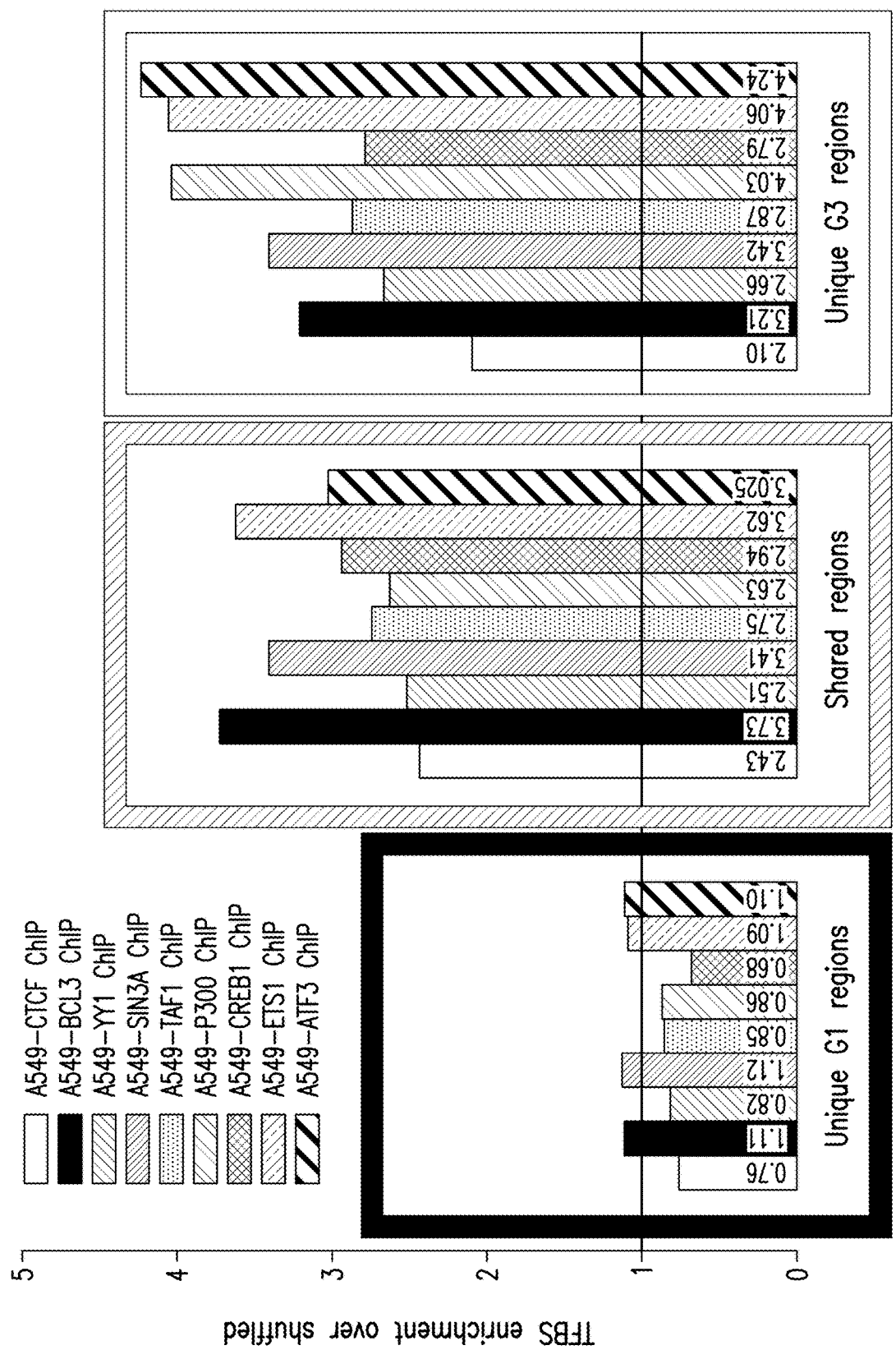
Figure 6E:
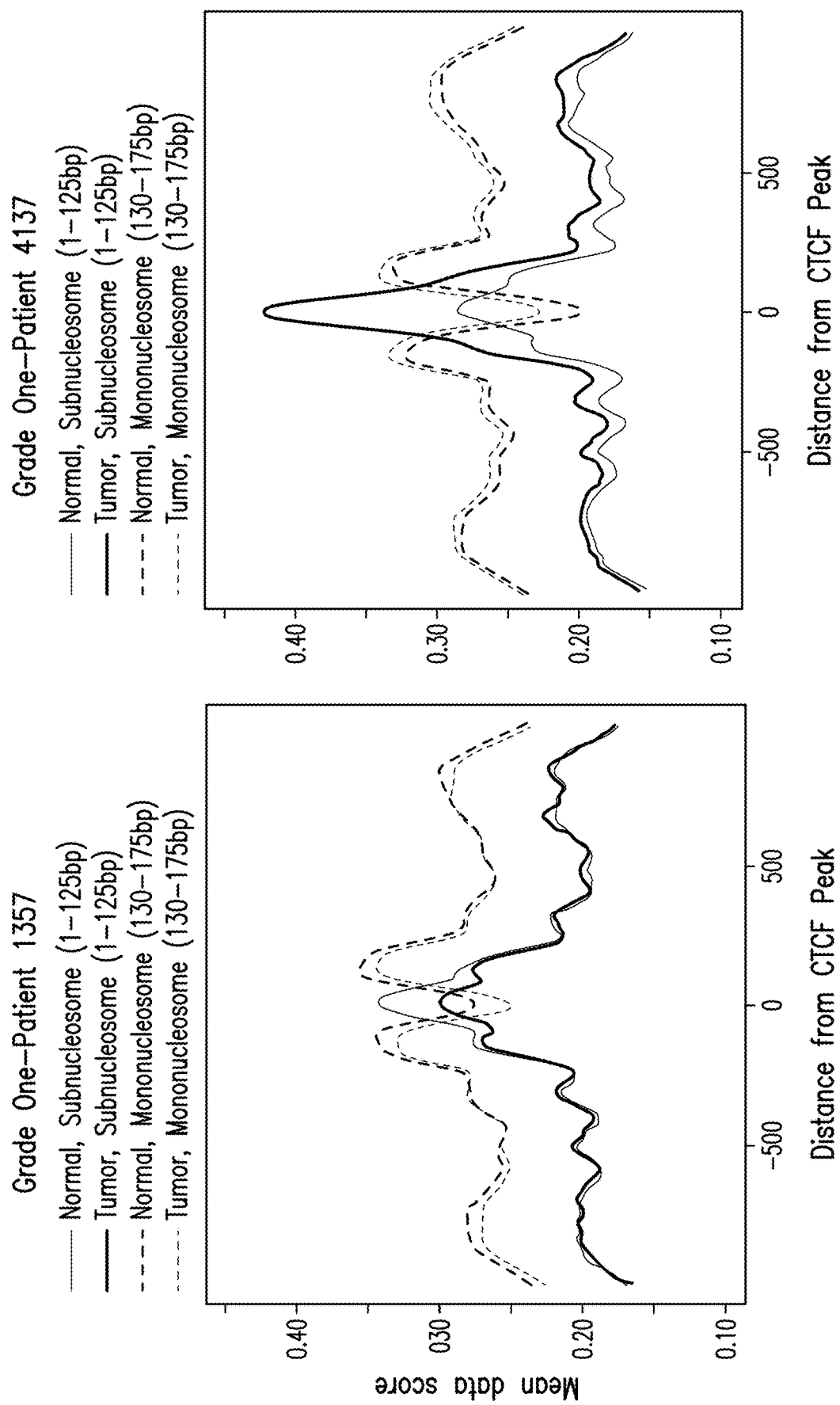

In order to verify that the TFBS depletion in the regions of difference was a feature exclusive to the grade one patients, the overlap of regions of difference between the grade one and grade three patients was first determined, and it was found that 2,331 regions were shared in common (FIG. 6C, FIGS. 9B-9D). When each of these categories was compared to TFBSs, it was found that the regions unique to grade one patients were depleted of TFBSs, whereas the shared genes and the genes unique to grade three patients were highly enriched for TFBSs (FIG. 6D). These results suggest that changes in nucleosome distribution in the grade one tumors broadly alter access to the genome, and the changes that persist in the grade three patients are likely the result of differential transcription factor binding.

Figure 6F:
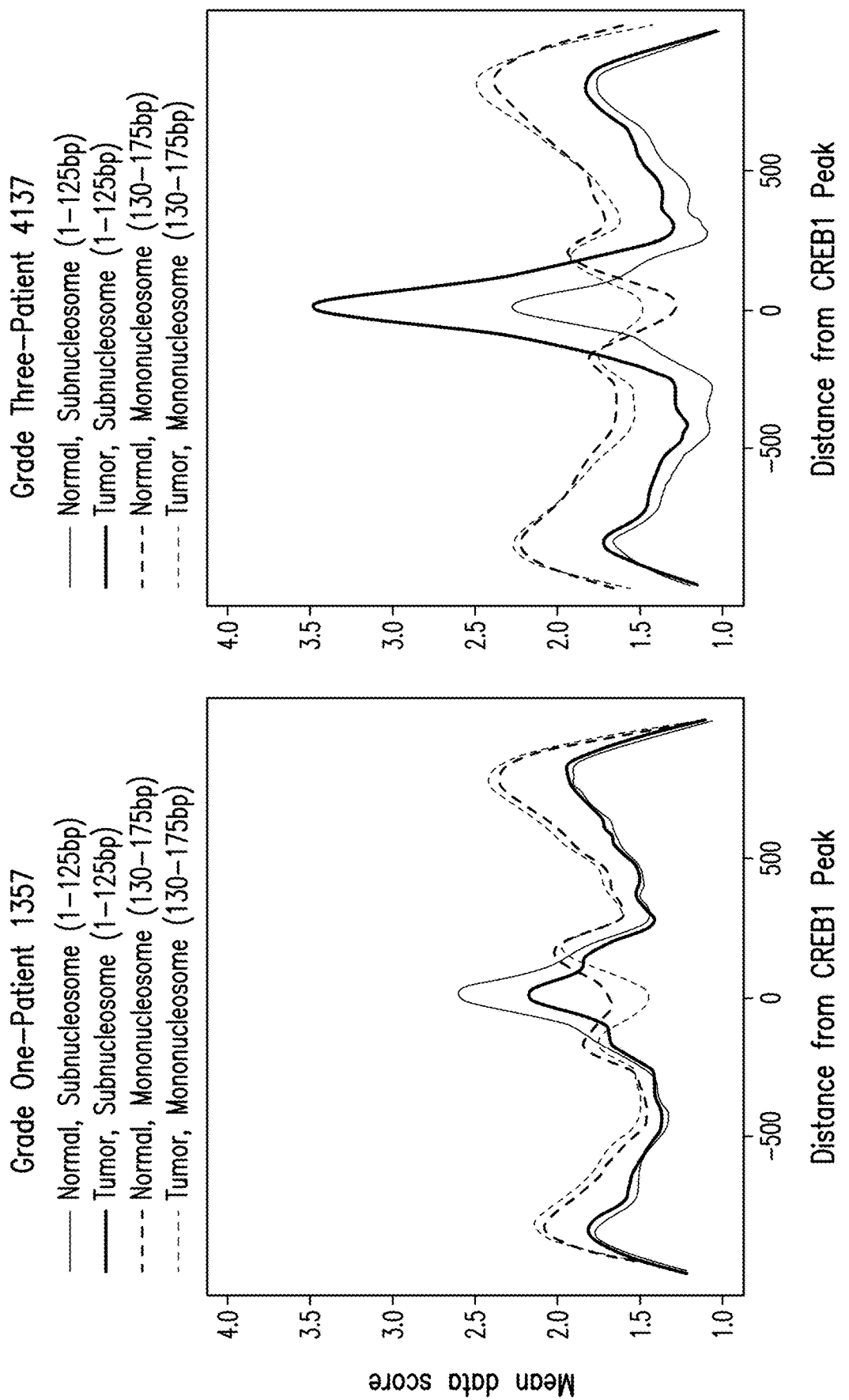

To test this hypothesis, binding alterations were examined at specific transcription factor binding sites. Using subnucleosomal fragment data for all fragments less than 125 bp from grade one and grade three patients, all reads were plotted and centered on the binding sites for Ctcf (FIG. 6E) and Creb1 (FIG. 6F). It was found that when normal and tumor tissue were compared, there is a 13% decrease in binding of Ctcf and a 19% decrease of Creb1 binding in the grade one patients, while for the grade three patients there was a 47% increase in binding of Ctcf and a 31% increase of Creb1 binding. The nucleosome size fragments were also plotted with a size range of 130-175 bp for each patient and transcription factor, and it was confirmed that these inferred transcription factor binding events were associated with nucleosome free regions, typical of regulatory factor binding sites [Id.]. Taken together, these results suggest that nucleosome redistribution, which provides the opportunity for transcription factors to bind with a greater probability, is a potentiating event in the progression of cancer.

Nucleosome Distribution Changes are Widespread in the Progression of CRC, Consistent with LAC, Driven by DNA Sequence and Potentiate Transcription Factor Binding To determine whether the widespread nucleosome redistributions were a feature unique to LAC or if nucleosome alterations are a common characteristic of adenocarcinoma types, the nucleosome distribution was mapped in CRC patients. mTSS-seq was performed on matched normal tissue and tumors of stage two (S2), stage three (S3) and stage four (S4). The correlation between normal and tumor nucleosome distribution was calculated for each patient. Widespread changes were found in patients with early-CRC (S2 and S3). There were 2,133 genes shared in common between these early CRC patients. These 2,133 common CRC genes were compared with the 1,804 common LAC genes, and 709 genes with altered nucleosome distribution were found shared between LAC and CRC. The nucleosome distribution at the ATM, HKR1, NOP16, and KIF2B genes for early LAC, and all CRC patients showed that the nucleosome redistributions identified are consistent between the early CRC patients and are absent in the advanced (S4) CRC patient (FIGS. 7A-7D). These plots also show that nucleosome redistributions in early CRC are consistent with changes in early LAC patients for ATM, HKR1, NOP16, and KIF2B genes (FIGS. 7A-7D) [Bakhoum, S. F., et al. Genome stability is ensured by temporal control of kinetochore-microtubule dynamics. Nat Cell Biol 11, 27-35 (2009), Kundel, D. W. et al. Molecular characterizations of Nop16 in murine mammary tumors with varying levels of c-Myc. Transgenic Res 21, 393-406 (2012); Webb, E. L. et al. Search for low penetrance alleles for colorectal cancer through a scan of 1467 non-synonymous SNPs in 2575 cases and 2707 controls with validation by kin-cohort analysis of 14 704 first-degree relatives. Hum Mol Genet 15, 3263-3271 (2006); Yang, H. et al. ATM sequence variants associate with susceptibility to non-small cell lung cancer. Int J Cancer 121, 2254-2259 (2007)]. This consistency between the two early adenocarcinomas is an important finding, indicating that nucleosome redistributions are a common genomic feature of early transformation.

Figure 7A:
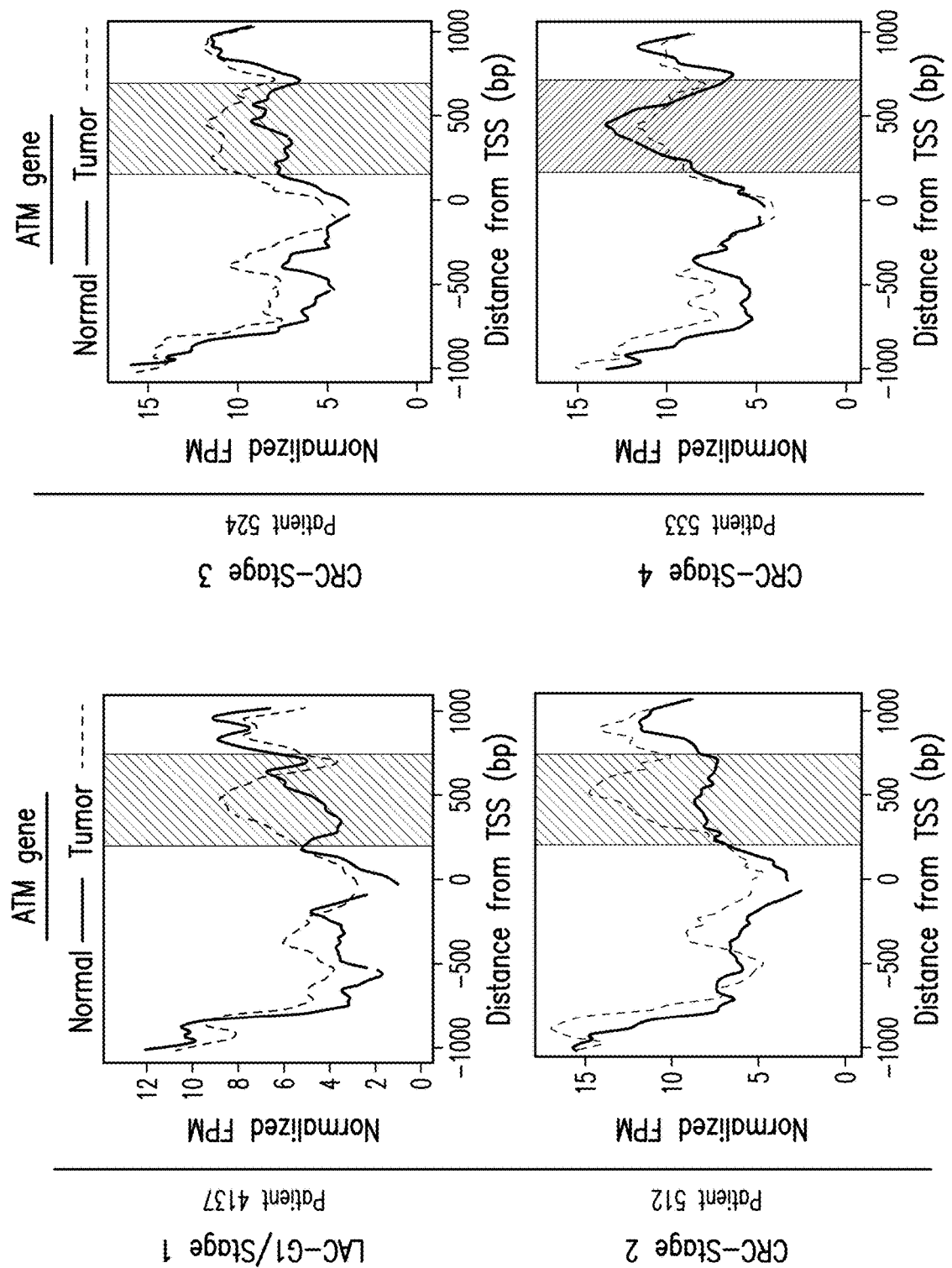
FIGS. 7A-7G depict nucleosome distribution changes in early-CRC are widespread, concordant with LAC changes, DNA-directed and potentiate transcription factor binding.
Figure 7B:
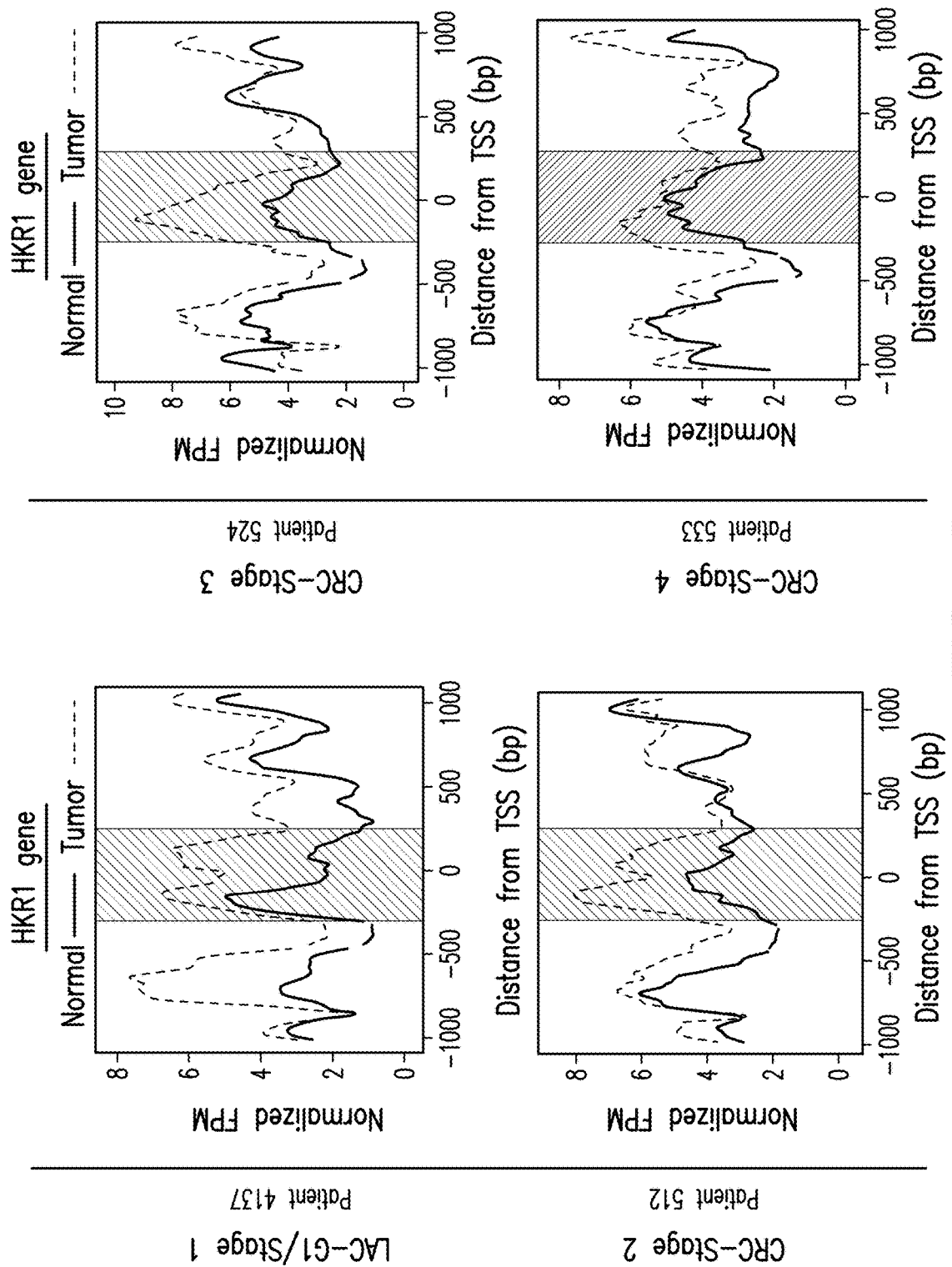
Figure 7C:
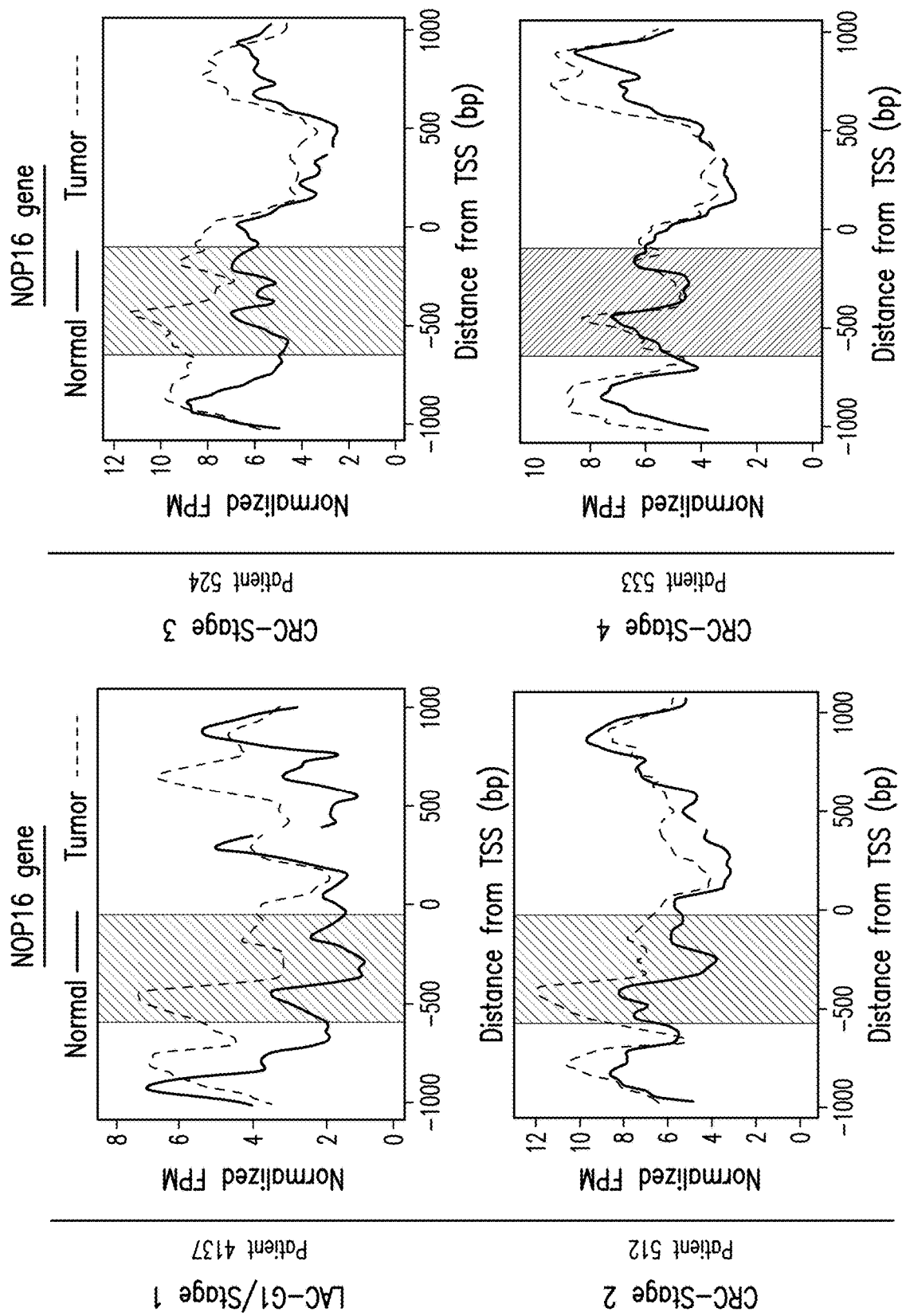
Figure 7D:
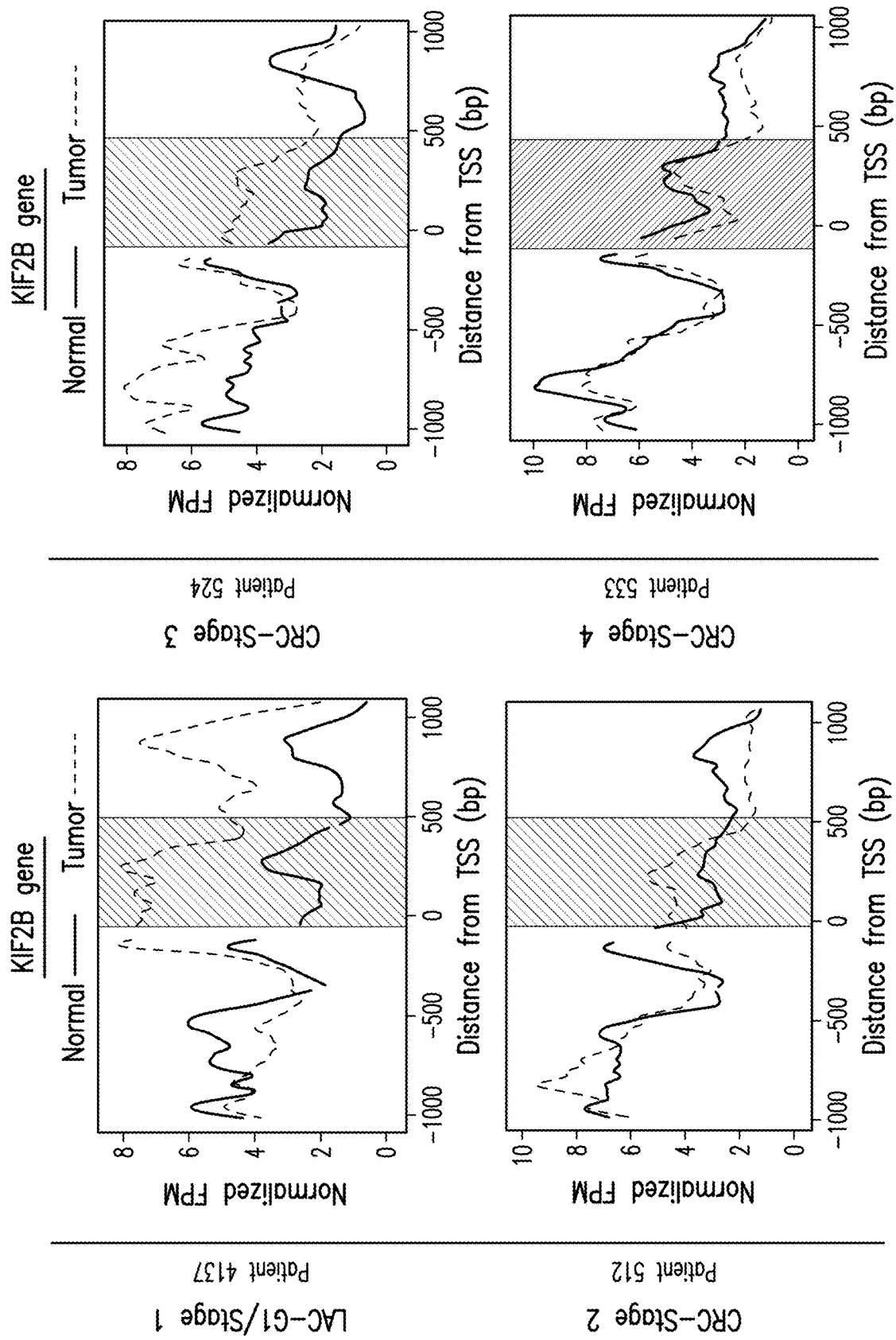
Figure 7E:
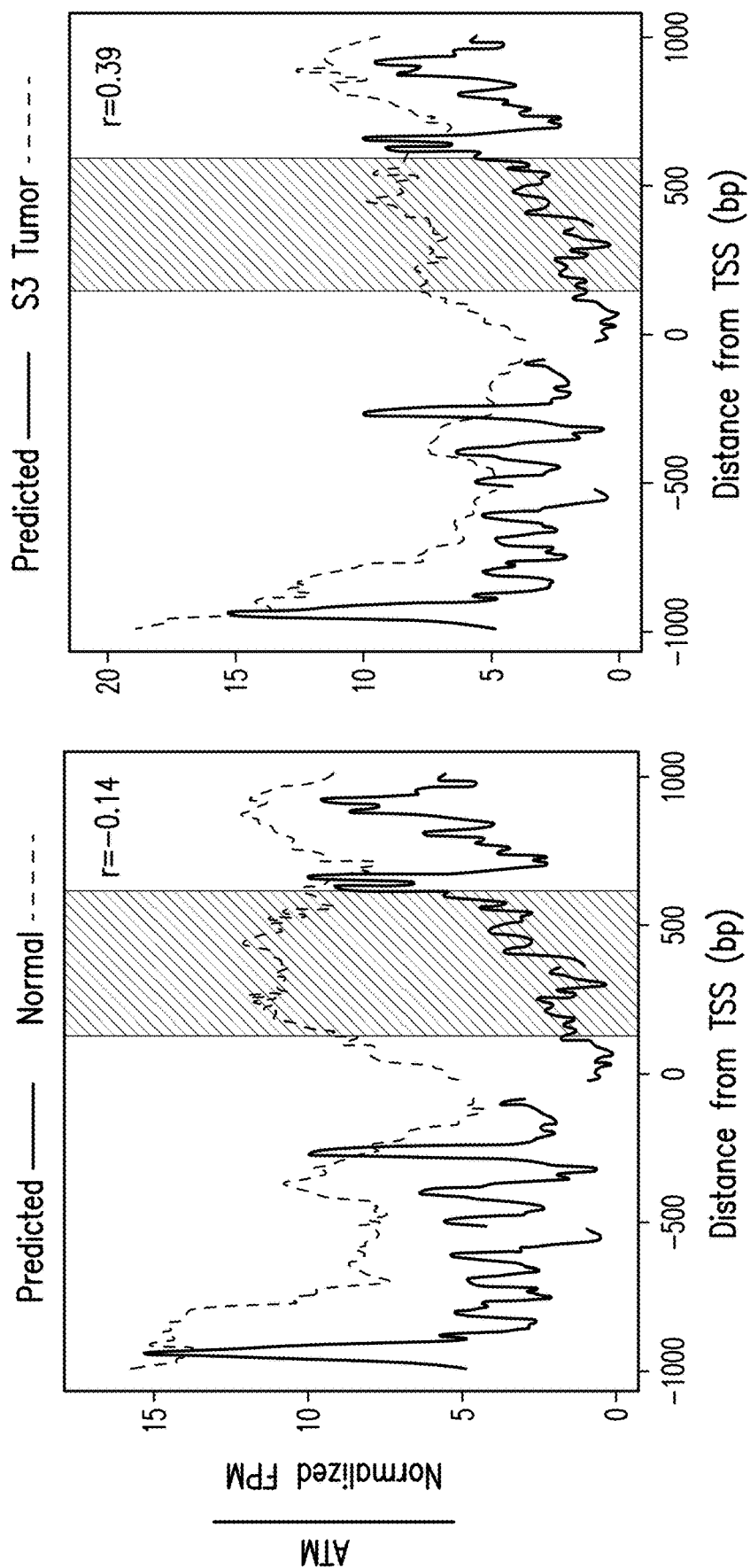
Figure 7F:
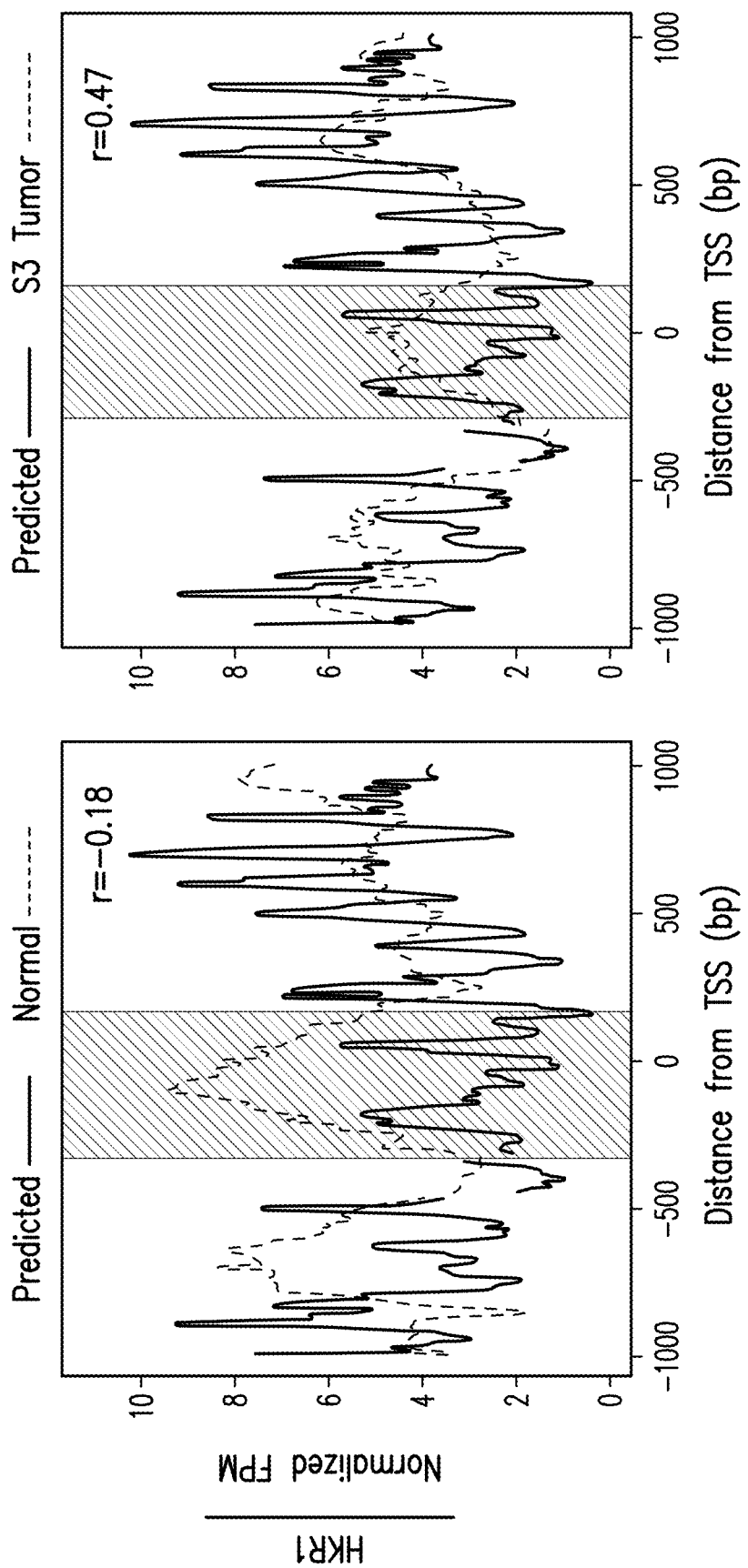
Figure 7G:
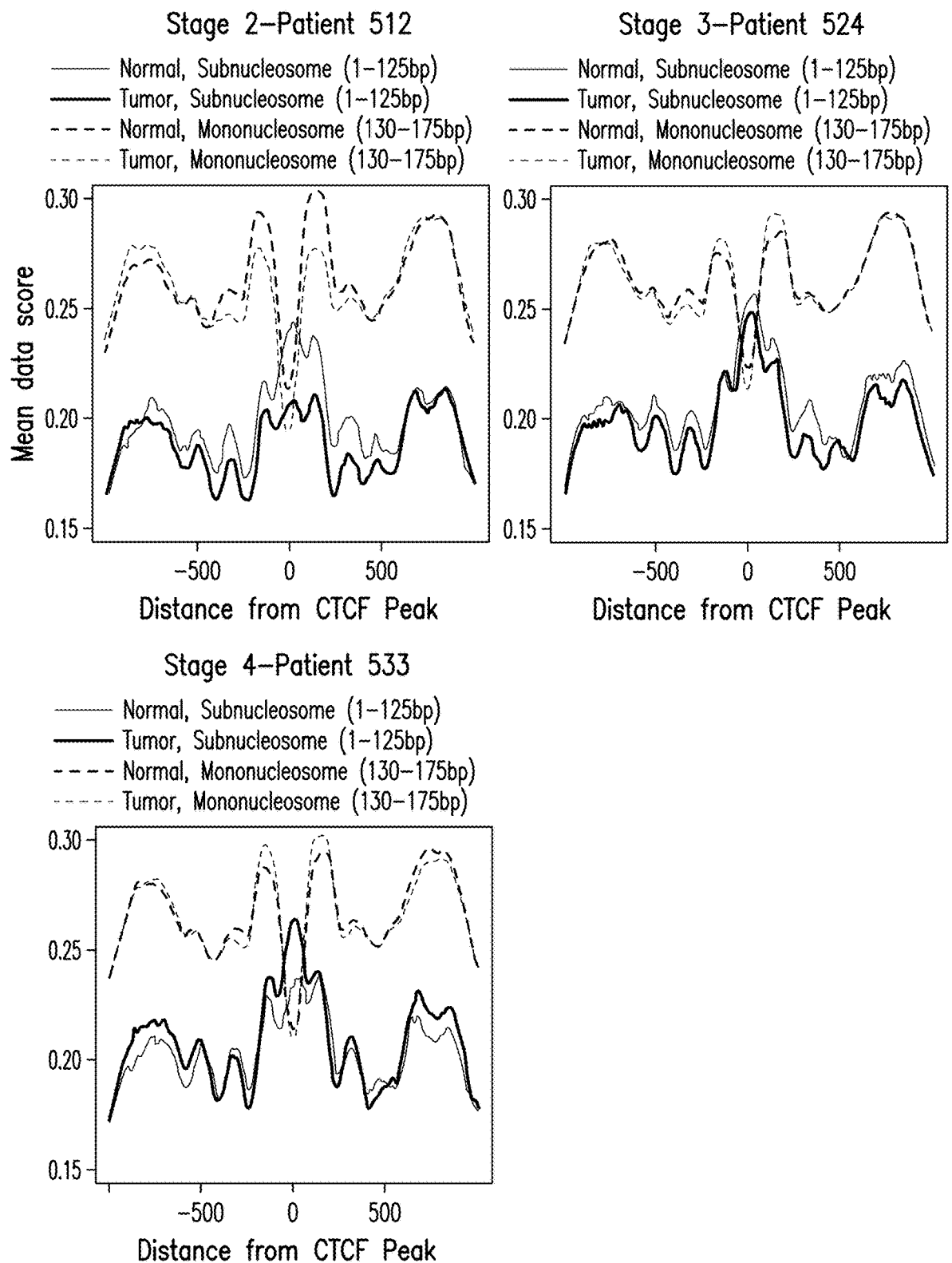

To assess the role of cis- and trans-acting factors governing nucleosome redistributions in the progression of CRC, the experimentally determined nucleosome distributions for the common CRC genes were first compared to the computationally predicted model. It was found that the early CRC tumors had a higher correlation than normal with the predicted model at over 58% of genes. The S3 CRC tumor and matched normal data compared to the predicted model at ATM and HKR1 genes showed a greater agreement between the predicted model and the tumor than between predicted model and the normal data (FIGS. 7E-7F). Finally, centering subnucleosomal fragments on CTCF binding peaks showed a decrease in binding in the early CRC patients and an increase in binding in the more advanced CRC patients (FIG. 7G). These results confirm that nucleosome distribution changes are widespread and consistent in both early LAC and CRC, are directed by the underlying DNA sequence, and likely potentiate an increase in transcription factor binding in advanced cancer.

Taken together, these results clarify structure-function relationships in the human genome, and support a hierarchical mechanism for chromatin mediated genomic regulation [Sexton, B. S. et al. The spring-loaded genome: nucleosome redistributions are widespread, transient, and DNA-directed. Genome Res 24, 251-259 (2014)]. This study demonstrates that widespread, DNA-directed nucleosome redistributions are limited to early tumors in LAC and CRC, though applicable to other carcinogens and diseases. This hierarchical model describes the interpretation that these nucleosome redistributions likely allow for inappropriate regulatory licensing in cancer (FIG. 8A). Indeed, inappropriate genomic licensing is frequently cited as a characteristic of transformed phenotype [Feinberg, A. P. Epigenetic stochasticity, nuclear structure and cancer: the implications for medicine. J Intern Med (2014); Timp, W. & Feinberg, A. P. Cancer as a dysregulated epigenome allowing cellular growth advantage at the expense of the host. Nat Rev Cancer 13, 497-510 (2013)]. It can be interpreted that in the later stage and grade tumors when nucleosomes return to their basal positions, the regulatory machinery is altered, and contributes to the progression of the disease (FIG. 8B). This comprehensive and integrated analysis of the relationship between chromatin structure and the progression of cancer has allowed one to define nucleosome alterations as generally exploited sites of concerted dysregulation in cancer.

Glossary of Claim Terms

ATM gene: This term is used herein to refer to a gene that is involved in DNA replication and implicated in cancer. An exemplary sequence of the ATM gene can be seen in SEQ ID NO.15.

Chromatin structure: This term is used herein to refer to the presence of chromatin around the transcription start site.

Control level: This term is used herein to refer to measurement of nucleosome distribution in a control group.

Control: This term is used herein to refer to a group or subject against which the suspected-carcinogenic tissue is compared to determine differences in levels of nucleosome distribution between the tissue and the control.

Entirety of genome: This term is used herein to refer to a complete set of genes of a human being or within a sample thereof.

Flanking: This term is used herein to refer to base pairs on each side of the transcription start site along the sequence.

Grade one subject: This term is used herein to refer to an individual potentially having a well-differentiated, early, or low grade tumor/cancer.

Not suspected of being carcinogenic: This term is used herein to refer to a normal tissue mass, i.e., one that is not suspected or being tested for carcinogenic properties.

Nucleosome distribution: This term is used herein to refer to an amount of nucleosome present within a range of base pairs flanking the transcription start site.

Patient: This term is used herein to refer to a human being suffering from a disease or disorder, such as cancer, or a symptom thereof, such as a grade one tumor.

Primer: This term is used herein to refer to a short strand of RNA or DNA that functions as a starting point for DNA synthesis by flanking a gene to be replicated. Examples of primers may be found in SEQ ID NO:3, SEQ ID NO:4, SEQ ID NO:5, and SEQ ID NO:6. These primers are used to amplify the base pairs flanking the transcription start sites, allowing for a quantitative measurement of the targeted region.

Quantitative measurement: The term is used herein to refer to a quantification of an amount of a measured component (e.g., nucleosome distribution surrounding a transcription start site) that is performed after identifying and capturing a target region.

Suspected of being carcinogenic: This term is used herein to refer to a tumor, neoplasm, or other tissue mass being tested for carcinogenic properties.

All referenced publications are incorporated herein by reference in their entirety. Furthermore, where a definition or use of a term in a reference, which is incorporated by reference herein, is inconsistent or contrary to the definition of that term provided herein, the definition of that term provided herein applies and the definition of that term in the reference does not apply.

The advantages set forth above, and those made apparent from the foregoing description, are efficiently attained. Since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention that, as a matter of language, might be said to fall therebetween.

What is claimed is:

1. A method of early detection of a grade one tumor in a patient via analysis of chromatin structure, and dysregulation thereof, in a genome of said patient, comprising the steps of:
collecting a first sample from a first tissue of said patient, said first sample of said patient not being carcinogenic;
collecting a second sample from a second tissue of said patient, said second sample of said patient being carcinogenic;
targeting and capturing less than a 5% region of said genome in each of said first and second samples of said stage one subject, said captured region containing transcription start sites in said genome;
quantitatively measuring nucleosome distribution in said first sample within a first predetermined range of base pairs flanking a transcription start site in said first sample, wherein said quantitative measurement is performed after capturing said first predetermined range of base pairs in an Ataxia-Telangiesctasia Mutated (ATM) gene in said first sample;
quantitatively measuring nucleosome distribution in said second sample within a second predetermined range of base pairs flanking a transcription start site in said first sample, wherein said quantitative measurement is performed after capturing said second predetermined range of base pairs in an ATM gene in said second sample;
evaluating levels of nucleosome distribution between said first sample and said second sample, wherein a difference of nucleosome distribution between said levels of nucleosome distribution of 10% or higher indicates said second sample being carcinogenic, whereby said difference is not prevalent in later grade subjects.

2. A method as in claim 1, further comprising: said grade one tumor indicating a cancer selected from the group consisting of lung adenocarcinoma and colorectal cancer.

3. A method as in claim 1, further comprising: said first predetermined range of base pairs flanking said transcription start site in said first sample being 2,000 base pairs; and said second predetermined range of base pairs flanking said transcription start site in said second sample being 2,000 base pairs.

4. A method as in claim 1, wherein the less than 5% region of said genome of can be obtained from across an entirety of said genome of said first and second samples.

5. A method as in claim 1, further comprising: said first tissue and said second tissue corresponding to one another.

6. A method as in claim 1, further comprising: the step of capturing said region performed via micrococcal nuclease digestion.

7. A method as in claim 1, wherein: the step of capturing said first predetermined range of base pairs in said ATM gene in said first sample is performed by using SEQ ID NO:3 as an on-target forward primer, SEQ ID NO:4 as an on-target reverse primer, SEQ ID NO:5 as an off-target forward primer, and SEQ ID NO:6 as an off-target reverse primer, and the step of capturing said second predetermined range of base pairs in said ATM gene in said second sample is performed by using SEQ ID NO:3 as an on-target forward primer, SEQ ID NO:4 as an on-target reverse primer, SEQ ID N0:5 as an off-target forward primer, and SEQ ID N0:6 as an off-target reverse primer; wherein the primers are used to amplify the first and second predetermined ranges of base pairs, such that nucleosome distribution proximate to the transcription start sites can be quantitatively measured.

8. A method of early detection of a grade one tumor in a patient, comprising the steps of:
    collecting a sample from a tissue of said patient, said sample of said patient being carcinogenic, said sample including a genome of said patient;
    targeting and capturing less than a 5% region of said genome in said sample of said patient, said captured region containing transcription start sites in said genome;
    quantitatively measuring nucleosome distribution in said sample within a predetermined range of base pairs flanking a transcription start site in said sample, wherein said quantitative measurement is performed after capturing said predetermined range of base pairs in an Ataxia-Telangiesctasia Mutated (ATM) gene in said sample;
    evaluating a measured level of nucleosome distribution to a control level in a control, wherein a difference of nucleosome distribution between said measured level and said control level of 10% or higher indicates said sample being carcinogenic, whereby said difference is not prevalent in later grade subjects.

9. A method as in claim 8, further comprising: said grade one tumor indicating a cancer selected from the group consisting of lung adenocarcinoma and colorectal cancer.

10. A method as in claim 8, further comprising: said predetermined range of base pairs flanking said transcription start site in said sample being 2,000 base pairs.

11. A method as in claim 8, further comprising: prior to evaluating said measured level of nucleosome distribution to said control level, quantitatively measuring nucleosome distribution in said control within a predetermined range of base pairs flanking a transcription start site in said control, wherein said control is a sample from an additional tissue of said patient, said additional tissue of said patient not being carcinogenic.

12. A method as in claim 8, further comprising wherein the less than 5% region of said genome of can be obtained from across an entirety of said genome of said sample.

13. A method as in claim 8, further comprising: said tissue and said control corresponding to one another.

14. A method as in claim 13, further comprising: the step of capturing said region performed via micrococcal nuclease digestion.

15. A method as in claim 8, wherein the step of capturing said predetermined range of base pairs in said ATM gene in said sample is performed by using SEQ ID NO:3 as an on-target forward primer, SEQ ID N0:4 as an on-target reverse primer, SEQ ID NO:5 as an off-target forward primer, and SEQ ID N0:6 as an off-target reverse primer, wherein the primers are used to amplify the first and second predetermined ranges of base pairs, such that nucleosome distribution proximate to the transcription start sites can be quantitatively measured.

16. A method of early detection of a grade one tumor associated with lung adenocarcinoma or colorectal cancer in a patient via analysis of chromatin structure, and dysregulation thereof, in a genome of said patient, comprising the steps of:
    collecting a first sample from a first tissue of said patient, said first sample of said patient not being carcinogenic;
    collecting a second sample from a second tissue of said patient, said second sample of said patient being carcinogenic;
    targeting and capturing less than a 5% region of said genome in each of said first and second samples of said stage one subject, said captured region containing transcription start sites in said genome, wherein the step of capturing said region is performed via micrococcal nuclease digestion;
    quantitatively measuring nucleosome distribution in said first sample within a first predetermined range of base pairs flanking a transcription start site in said first sample, said first predetermined range of base pairs flanking said transcription start site in said first sample being 2,000 base pairs, wherein the quantitative measurement of said nucleosome distribution in said first sample is taken across an entirety of said genome of said first sample, wherein said quantitative measurement is performed by capturing said first predetermined range of base pairs in an ATM gene in said first sample using SEQ ID NO:3 as an on-target forward primer, SEQ ID NO:4 as an on-target reverse primer, SEQ ID NO:5 as an off-target forward primer, and SEQ ID NO:6 as an off-target reverse primer, wherein the primers are used to amplify the first predetermined range of base pairs, such that nucleosome distribution proximate to the transcription start sites can be quantitatively measured;
    quantitatively measuring nucleosome distribution in said second sample within a second predetermined range of base pairs flanking a transcription start site in said second sample, said second predetermined range of base pairs flanking said transcription start site in said second sample being 2,000 base pairs, wherein the quantitative measurement of said nucleosome distribution in said second sample is taken across an entirety of said genome of said second sample, wherein said quantitative measurement is performed by capturing said second predetermined range of base pairs in an Ataxia-Telangiesctasia Mutated (ATM) gene in said second sample using SEQ ID NO:3 as an on-target forward primer, SEQ ID NO:4 as an on-target reverse primer, SEQ ID NO:5 as an off-target forward primer, and SEQ ID NO:6 as an off-target reverse primer, wherein the primers are used to amplify the second predetermined range of base pairs, such that nucleosome distribution proximate to the transcription start sites can be quantitatively measured, said first tissue and said second tissue corresponding to one another;

evaluating levels of nucleosome distribution between said first sample and said second sample, wherein a difference of nucleosome distribution between said levels of nucleosome distribution of 10% or higher indicates said second sample being carcinogenic, whereby said difference is not prevalent in later grade subjects.

* * * * *